US008945359B2

(12) United States Patent
Honda et al.

(10) Patent No.: US 8,945,359 B2
(45) Date of Patent: Feb. 3, 2015

(54) FLAVIN-BINDING GLUCOSE DEHYDROGENASE

(71) Applicant: Ikeda Food Research Co., Ltd., Fukuyama-shi (JP)

(72) Inventors: Michinari Honda, Fukuyama (JP); Sayaka Taki, Onomichi (JP); Ryo Takenaka, Fukuyama (JP)

(73) Assignee: Ikeda Food Research Co., Ltd., Fukuyama-shi (JP)

( * ) Notice: Subject to any disclaimer, the term of this patent is extended or adjusted under 35 U.S.C. 154(b) by 0 days.

(21) Appl. No.: 13/777,827

(22) Filed: Feb. 26, 2013

(65) Prior Publication Data

US 2013/0203093 A1 Aug. 8, 2013

Related U.S. Application Data

(63) Continuation of application No. PCT/JP2012/071380, filed on Aug. 24, 2012.

(30) Foreign Application Priority Data

Aug. 26, 2011 (JP) ................................ 2011-184764
Oct. 7, 2011 (JP) ................................ 2011-222390

(51) Int. Cl.
*C12N 9/04* (2006.01)
*C12Q 1/32* (2006.01)
*G01N 27/327* (2006.01)
*C12Q 1/00* (2006.01)

(52) U.S. Cl.
CPC .............. *C12N 9/0006* (2013.01); *C12Q 1/006* (2013.01); *C12Q 1/32* (2013.01); *C12Y 101/9901* (2013.01); *C12Y 101/01047* (2013.01)
USPC ........... 204/403.04; 435/14; 435/26; 435/190

(58) Field of Classification Search
None
See application file for complete search history.

(56) References Cited

U.S. PATENT DOCUMENTS

| | | | | |
|---|---|---|---|---|
| 2006/0063217 | A1 | 3/2006 | Omura et al. | |
| 2008/0003628 | A1 | 1/2008 | Kitabayashi et al. | |
| 2008/0014611 | A1 | 1/2008 | Kitabayashi et al. | |
| 2008/0014612 | A1 | 1/2008 | Tsuji et al. | |
| 2008/0020426 | A1 | 1/2008 | Aiba et al. | |
| 2008/0090278 | A1 | 4/2008 | Kitabayashi et al. | |
| 2009/0155848 | A1 | 6/2009 | Aiba et al. | |
| 2009/0176262 | A1 | 7/2009 | Omura et al. | |
| 2009/0181408 | A1 | 7/2009 | Tanaka et al. | |
| 2009/0259024 | A1 | 10/2009 | Tsuji et al. | |
| 2010/0297743 | A1 | 11/2010 | Omura et al. | |
| 2011/0033880 | A1 | 2/2011 | Yada et al. | |
| 2011/0318810 | A1 | 12/2011 | Tajima et al. | |
| 2012/0122130 | A1 | 5/2012 | Omura et al. | |
| 2012/0171708 | A1 | 7/2012 | Kawaminami et al. | |
| 2013/0168263 | A1* | 7/2013 | Sode et al. | 205/777.5 |

FOREIGN PATENT DOCUMENTS

| | | | |
|---|---|---|---|
| JP | 2007/289148 | A | 11/2007 |
| JP | 2010/057427 | | 3/2010 |
| WO | 2004/058958 | A1 | 7/2004 |
| WO | 2007/139013 | A1 | 12/2007 |
| WO | 2008/001903 | A1 | 1/2008 |
| WO | 2010/140431 | A1 | 12/2010 |
| WO | 2011/034108 | A1 | 3/2011 |
| WO | 2012/001976 | A1 | 1/2012 |

OTHER PUBLICATIONS

Kent, Total chemical synthesis of proteins, Chem. Soc. Rev., 2009, 38, 338-51.*
UniProt, Accession No. A7F9L2, Mar. 2011, www.uniprot.org.*
Uzuhashi et al., Dumontinia root rot of liver leaf caused by *Dumontinia tuberosa*, J. Gen. Plant Pathol., 2010, 76, 183-87.*
Punt et al., Filamentous fungi as cell factories for heterologous protein production, Trends Biotechnol., 2002, 20, 200-06.*
International Search Report issued in PCT/JP2012/071380 filed on Aug. 24, 2012.
Written Opinion issued in PCT/JP2012/071380 filed on Aug. 24, 2012 (w/English translation).
Rolke et al.—"Functional analysis of H2O2—generating systems in *Botryris cinerea*: the major Cu—Zn—superoxide dismutase (BCSOD1) contributes to virulence on French bean, whereas a glucose oxidase (BCGOD1) is dispensable", Molecular Plant Pathology (2004) vol. 5, No. 1, pp. 17-27.
Database GenBank-Accessin No. ED000423, Aug. 3, 2007, hypothetical protein SS1G_14293.
Database GenBank Accessin No. AJ555871, Jan. 5, 2004, Biotryotinia fuckeliana god1 gene for glucose oxidase, specimen voucher SAS 56.

* cited by examiner

*Primary Examiner* — Robert Mondesi
*Assistant Examiner* — Todd M Epstein
(74) *Attorney, Agent, or Firm* — Oblon, Spivak, McClelland, Maier & Neustadt, L.L.P.

(57) ABSTRACT

The invention provides a flavin-binding glucose dehydrogenase exhibiting reduced fluctuation of activity depending on temperature environment, and a method for measuring glucose concentration using the flavin-binding glucose dehydrogenase. The flavin-binding glucose dehydrogenase has the following properties (1) to (3): (1) activity: which exhibits glucose dehydrogenase activity in the presence of an electron acceptor; (2) substrate specificity: which exhibits an activity of 10% or less against maltose, D-galactose, D-fructose, sorbitol, lactose and sucrose when the activity against D-glucose is defined as 100%; and (3) temperature characteristics: which exhibits lower fluctuation of activity in a wide temperature range of 10 to 50° C.

4 Claims, 7 Drawing Sheets

FLAVIN-BINDING GLUCOSE DEHYDROGENASE

FIELD OF THE INVENTION

The present invention relates to a flavin-binding glucose dehydrogenase useful for measurement of glucose concentration and a method for measuring glucose concentration by using the flavin-binding glucose dehydrogenase.

BACKGROUND OF THE INVENTION

Rapid and accurate measurement of the concentration of blood glucose is important for the diagnosis of diabetes. As examples of a method for measuring glucose concentration, a chemical method and an enzymatic method are known; among them the enzymatic method is preferable from the viewpoints of specificity and safety. Among the enzymatic methods, an electrochemical biosensor is advantageous from the viewpoints of reduction of the amount of a specimen, reduction of measuring time, and reduction of the size of a device.

Glucose oxidase is known as an enzyme usable for such a biosensor. However, because glucose oxidase gives rise to the problem, for example, oxygen dissolved in blood causes measurement errors, therefore, some glucose dehydrogenases have been developed. Among glucose dehydrogenases, much attention is focused on flavin-binding glucose dehydrogenases as the enzyme for glucose biosensors because they need no addition of a coenzyme and are unaffected by dissolved oxygen (Patent Documents 1 to 7). These flavin-binding dehydrogenases include those which are superior in substrate specificity (Patent Document 5), those which exhibit an activity of 15% or more at 10° C., an activity of 30% or more at 20° C., and an activity of 70% or more at 60° C., when the activity at 50° C. is defined as 100% (Patent Document 6), and modified enzymes which are cell homogenates of recombinant *Escherichia coli* transformed by a gene encoding a FAD-dependent glucose dehydrogenase derived from *Aspergillus oryzae* and which exhibits improved relative activity at 25° C. when the activity at 37° C. was defined as 100% (Patent Document 7).

CITATION LIST

Patent Documents

Patent Document 1: JP-A-2007-289148
Patent Document 2: WO2007/139013
Patent Document 3: WO2008/001903
Patent Document 4: WO2004/058958t
Patent Document 5: WO2010/140431
Patent Document 6: JP-A-2010-057427
Patent Document 7: WO2011/034108

SUMMARY OF THE INVENTION

Problem to be solved by the Invention

However, with regard to the activities of these glucose dehydrogenases currently used, there exist glucose dehydrogenases which are significantly deteriorated in reactivity at the high-temperature, and glucose dehydrogenases which are deteriorated in reactivity at the low-temperature while exhibiting high reactivity at the high-temperature, indicating that their activity are largely fluctuated depending on a temperature range, and it is therefore desired to develop an enzyme exhibiting lower fluctuation of activity in a wide temperature range.

Accordingly, it is an object of the present invention to provide a flavin-binding glucose dehydrogenase exhibiting lower fluctuation of activity in a wide temperature range of 10 to 50° C., and to provide a method for measuring glucose concentration by using the same.

Means for Solving the Problem

In light of this, the inventors of the present invention have made a screening of glucose dehydrogenases derived from various organisms and, as a result, have found, among glucose dehydrogenases derived from filamentous fungi, a flavin-binding glucose dehydrogenase which exhibits high substrate specificity to glucose and exhibits reduced fluctuation of activity depending on temperature environment when measuring the activity, in which the activity at 10 to 50° C. is 20 to 150% when the activity at 30° C. is defined as 100%, and also found that the use of this flavin-binding glucose dehydrogenase enables glucose concentration to be measured with high reproducibility and high accuracy in various temperature environments. Also, the inventors of the present invention have succeeded in the cloning of these flavin glucose dehydrogenase genes and found that the enzyme can be efficiently produced.

Specifically, the present invention relates to the following [1] to [17].

[1] A flavin-binding glucose dehydrogenase having the following properties (1) to (3):
(1) activity: which exhibits glucose dehydrogenase activity in the presence of an electron acceptor;
(2) substrate specificity: which exhibits an activity of 10% or less against maltose, D-galactose, D-fructose, sorbitol, lactose and sucrose when the activity against D-glucose is defined as 100%; and
(3) temperature characteristics: which exhibits an activity range from 20 to 150% at 10 to 50° C. when the activity at 30° C. is defined as 100%.

[2] The glucose dehydrogenase according to the above [1], wherein the molecular weight of the polypeptide moiety of the enzyme is 60 to 70 kDa.

[3] The glucose dehydrogenase according to the above [1] or [2], wherein the glucose dehydrogenase has an optimum temperature of 40 to 45° C.

[4] The flavin-binding glucose dehydrogenase according to any one of the above [1] to [3], wherein the glucose dehydrogenase has the following properties (6) and (7):
(6) optimum pH: 6.0 to 7.5; and
(7) stable pH range: 4.5 to 7.0.

[5] The glucose dehydrogenase according to any one of the above [1] to [4], wherein the glucose dehydrogenase exhibits a residual activity of 70% or more after heat treatment at 40° C. for 15 minutes.

[6] The glucose dehydrogenase according to any one of the above [1] to [5], wherein the glucose dehydrogenase is derived from filamentous fungi.

[7] The glucose dehydrogenase according to any one of the above [1] to [6], wherein the glucose dehydrogenase is derived from filamentous fungi belonging to Sclerotiniaceae.

[8] A flavin-binding glucose dehydrogenase having amino acid sequences shown in the following (a), (b) or (c):
(a) an amino acid sequence represented by SEQ ID NO: 2, 4, 6, 8, 10, 12, 14 or 16;

(b) an amino acid sequence wherein one to several amino acids are substituted, deleted or added in an amino acid sequence represented by SEQ ID NO: 2, 4, 6, 8, 10, 12, 14 or 16, or (c) an amino acid sequence having at least 70% identity with that represented by SEQ ID NO: 2, 4, 6, 8, 10, 12, 14 or 16; and exhibiting glucose dehydrogenase activity.

[9] A purified flavin-binding glucose dehydrogenase, which has an amino acid sequence having at least 60% identity with that represented by SEQ ID NO: 10, 12, 14 or 16, and which has the following properties (i) to (v):

(i) which oxidizes the C-1 position of glucose;

(ii) which does not substantially use oxygen as an electron acceptor;

(iii) which has a stable pH range from 4.5 to 7.0;

(iv) which is a glycoprotein; and (v) the molecular weight of the polypeptide moiety of the enzyme is 60 to 70 kDa.

[10] A method for producing the glucose dehydrogenase according to any one of the above [1] to [9], which comprises culturing a microorganism belonging to eukaryotic cell having an ability of producing the glucose dehydrogenase and collecting the glucose dehydrogenase from the cultured product.

[11] A method for measuring glucose concentration in a test sample, wherein the method comprises a step of bringing the test sample into contact with the glucose dehydrogenase according to any one of the above [1] to [9].

[12] The method of measuring glucose according to the above [11], wherein the pH of the test sample is 5.0 to 9.0 when measured, and the measurement is not affected by dissolved oxygen.

[13] A reagent for measuring glucose concentration comprising the glucose dehydrogenase according to any one of the above [1] to [9].

[14] The reagent for measuring glucose concentration according to the above [13], wherein the pH of the reagent is 4.0 to 7.5.

[15] A biosensor for measuring glucose concentration comprising the glucose dehydrogenase according to any one of the above [1] to [9].

[16] The biosensor for measuring glucose concentration according to the above [15], wherein the pH of a reactive layer is 4.0 to 7.5, and the measurement is not affected by dissolved oxygen.

[17] A polynucleotide encoding the glucose dehydrogenase according to the above [8] or [9].

[18] A polynucleotide represented by the following (d), (e) or (f):

(d) a polynucleotide consisting of a base sequence represented by SEQ ID NO: 1, 3, 5, 7, 9, 11, 13 or 15;

(e) a polynucleotide capable of hybridizing to a polynucleotide consisting of a base sequence complementary to the base sequence of the polynucleotide of the (d) in a stringent condition and encoding a glucose dehydrogenase; or (f) a polynucleotide consisting of a base sequence having at least 70% identity with that represented by SEQ ID NO: 1, 3, 5, 7, 9, 11, 13 or 15 and encoding a glucose dehydrogenase.

[19] A polynucleotide which consists of a base sequence having at least 60% identity with that represented by SEQ ID NO: 9, 11, 13 or 15, which is a modified gene obtained by deleting all bases from A of the start codon to the 57th base in the amino acid sequence, and which encodes a glucose dehydrogenase.

[20] A vector comprising the polynucleotide according to the above [18] or [19].

[21] A transformed cell prepared by using the polynucleotide according to the above [18] or [19] or the vector according to the above [20].

[22] A method for producing a polynucleotide that encodes a glucose dehydrogenase, the method comprising a step of obtaining a polynucleotide encoding a part of a glucose dehydrogenase from a genome DNA or cDNA prepared from filamentous fungi by PCR using oligonucleotide represented by SEQ ID NO: 17 and SEQ ID NO: 18 as a primer.

Advantageous Effects of the Invention

If the flavin-binding glucose dehydrogenase of the present invention is used, blood glucose can be measured with high reproducibility with high accuracy, even if the temperature in the measuring circumstance varies between 10 to 50° C.

DETAILED DESCRIPTION OF THE INVENTION

Figure 1:
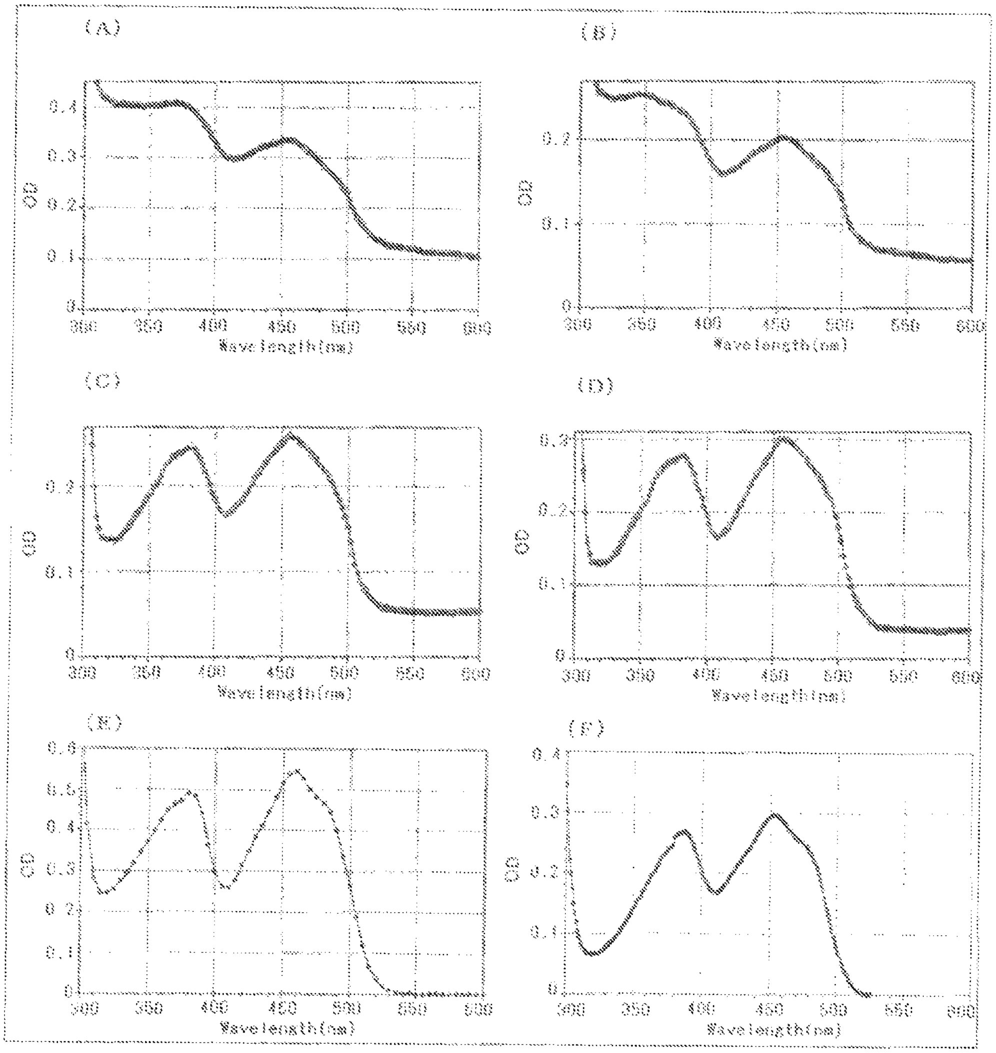
FIG. 1 shows the absorption spectrums of glucose dehydrogenases (A) to (F) according to the present invention.

The glucose dehydrogenase of the present invention is a flavin-binding glucose dehydrogenase and is an enzyme exhibiting activity when flavin is bound as a coenzyme. The glucose dehydrogenase of the present invention is an enzyme classified into EC1. 1. 99. 10 or EC1. 1. 99. 13, and preferably EC1. 1. 99. 10. Examples herein of the flavin include flavin adenine dinucleotide (FAD) and flavin mononucleotide (FMN).

The glucose dehydrogenase of the present invention has the following properties (1) to (3) and especially the following (3).

(1) Activity: which exhibits glucose dehydrogenase activity in the presence of an electron acceptor.

(2) Substrate specificity: which shows an activity of 10% or less against maltose, D-galactose, D-fructose, sorbitol, lactose and sucrose, when the activity against D-glucose is defined as 100%.

(3) Temperature characteristics: which has an activity range from 20 to 150% at 10 to 50° C., when the activity at 30° C. is defined as 100%.

First, the glucose dehydrogenase of the present invention exhibits (1) glucose dehydrogenase activity in the presence of an electron acceptor. Specifically, the glucose dehydrogenase of the present invention catalyzes a reaction for oxidizing a hydroxyl group of glucose in the presence of an electron acceptor to yield glucono-δ-lactone. When a FAD-binding glucose dehydrogenase reacts with glucose, a coenzyme FAD is converted into $FADH_2$. However, if a ferricyanide (for example, $[Fe(CN)_6]^{3-}$) is made to be present as the electron acceptor, $FADH_2$ converts the ferricyanide into a ferrocyanide ($[Fe(CN)_6]^{4-}$) in this case and is itself returned to FAD. When potential is applied to a ferrocyanide, the ferrocyanide delivers an electron to the electrode and returns to a ferricyanide. Therefore, when such an electron transport material is used as an electron acceptor, this enables electrochemical signal detection.

As to the substrate specificity of the glucose dehydrogenase of the present invention, the glucose dehydrogenase exhibits high specificity to D-glucose and is therefore suitable for measurement of glucose. The glucose dehydrogenase of the present invention exhibits (2) a reactivity as low as 10% or less against maltose, D-galactose, D-fructose, sorbitol, lactose and sucrose as compared with reactivity against D-glucose. More specifically, when the activity against D-glucose is defined as 100%, the glucose dehydrogenase of the present invention exhibits an activity of 10% or less, preferably 8% or less, and more preferably 5% or less against maltose, D-galactose, D-fructose, sorbitol, lactose and sucrose. The glucose dehydrogenase of the present invention exhibits an activity of more preferably 1% or less and even more preferably 0.5% or less against D-fructose, sorbitol, lactose and sucrose when the activity against D-glucose is defined as 100%.

When the activity of the glucose dehydrogenase of the present invention at 30° C. is defined as 100%, the glucose dehydrogenase of the present invention exhibits (3) an activity range from 20 to 150% at 10 to 50° C. The lower limit of the activity at 10 to 50° C. is preferably 30%, more preferably 40% and even more preferably 50%. Moreover, the upper limit of the activity at 10 to 50° C. is preferably 140%, more preferably 130%, even more preferably 120% and particularly preferably 110%.

Also, when the activity of the glucose dehydrogenase of the present invention at 30° C. is defined as 100%, the glucose dehydrogenase of the present invention preferably exhibits an activity range from 20 to 150% at 10 to 45° C., and the lower limit of the activity at 10 to 45° C. is more preferably 30%, even more preferably 40% and particularly preferably 50%. Moreover, the upper limit of the activity at 10 to 45° C. is more preferably 140%, even more preferably 130%, particularly preferably 120% and most preferably 110%.

Also, when the activity of the glucose dehydrogenase of the present invention at 45° C. is defined as 100%, the glucose dehydrogenase of the present invention preferably exhibits an activity range from 20 to 120% at 10 to 45° C., and the lower limit of the activity at 10 to 45° C. is more preferably 30%, even more preferably 40% and particularly preferably 50%. Moreover, the upper limit of the activity at 10 to 45° C. is more preferably 115%, even more preferably 110%, particularly preferably 105% and most preferably 100%.

Also, when the activity of the glucose dehydrogenase of the present invention at 50° C. is defined as 100%, the activity at 10° C. is preferably 25% or more, more preferably 30% or more, even more preferably 40% or more, and particularly preferably 50% or more. Moreover, the activity at 20° C. is preferably 40% or more, more preferably 50% or more, even more preferably 60% or more, and particularly preferably 70% or more.

The glucose dehydrogenase of the present invention preferably has the characteristics that (4) the molecular weight of the polypeptide moiety of the enzyme is 60 to 70 kDa and more preferably 60 to 65 kDa. The molecular weight of the polypeptide moiety of the enzyme is a molecular weight found when the protein moiety from which a sugar chain is removed is measured by SDS-polyacrylamide gel electrophoresis. The molecular weight of a whole enzyme found by SDS-polyacrylamide gel electrophoresis is easily varied by, for example, culture conditions and purification conditions. For example, variations in the amount of sugar chains to be added cause a difference in molecular weight, that is, in the case of a recombinant enzyme, a difference in the host has an influence on whether or not a sugar chain is present and on the amount of sugars to be added, leading to a difference in molecular weight.

The glucose dehydrogenase of the present invention preferably has (5) an optimum temperature of 40 to 45° C. More specifically, when the enzyme is measured at various temperatures by the method for measuring enzymatic activity which will be explained later, and the activity at the temperature at which the enzyme exhibits the maximum activity is defined as 100%, the enzyme preferably exhibits a relative activity of 80% or more at 40 to 45° C.

The glucose dehydrogenase of the present invention preferably has (6) an optimum pH of 6.0 to 7.5. More specifically, when the enzyme is measured at 25° C. by the method for measuring enzymatic activity using buffer solutions each having a different pH and the activity of the enzyme in the buffer solution having a pH at which the enzyme exhibits the maximum activity is defined as 100%, the enzyme preferably exhibits a relative activity of 80% or more at a pH of 6.0 to 7.5, or a relative activity of 40% or more at a pH of 5.0 to 9.0.

The glucose dehydrogenase of the present invention preferably has (7) a stable pH range from 4.5 to 7.0. More specifically, when, after the enzyme is treated at 25° C. for 16 hr in 100 mM buffer solutions each having a different pH, it is measured by the method for measuring enzymatic activity which will be explained later and the activity of the enzyme treated using the buffer solution having the most stable pH is defined as 100%, the enzyme preferably exhibits a residual activity of 70% or more at a pH of 4.5 to 7.0, or a residual activity of 40% or more at a pH of 4.0 to 7.5.

The glucose dehydrogenase of the present invention preferably exhibits (8) a residual activity of 70% or more after heat treatment at 40° C. for 15 minutes. More specifically, when, after the enzyme is treated at 4° C. for 15 minutes in a 100 mM potassium phosphate buffer solution (pH 6.0), it is measured by the method for measuring enzymatic activity which will be explained later and the activity measured at this time is defined as 100%, the residual activity measured by the method for measuring enzymatic activity which will be explained later is preferably 70% or more at 40° C., or 90% or more at 35° C. after the enzyme is treated at each temperature for 15 minutes.

Specific examples of the glucose dehydrogenase of the present invention include four types (A) to (D) as shown in the examples which will be explained later. Each glucose dehydrogenase will be explained.

The glucose dehydrogenase (A) is a flavin-binding glucose dehydrogenase having the following properties (1) to (3) and is particularly preferably one having any one of the following properties (4) to (8).

(1) Activity: it exhibits glucose dehydrogenase activity in the presence of an electron acceptor.

(2) Substrate specificity: it exhibits an activity of 10% or less against maltose, D-galactose, D-fructose, sorbitol, lactose and sucrose, when the activity against D-glucose is defined as 100%.

(3) Temperature characteristics: it exhibits an activity range from 20 to 150% at 10 to 50° C. when the activity at 30° C. is defined as 100%. The preferred range is preferably 30 to 140%, more preferably 40 to 130% and even more preferably 50 to 120% when the substrate concentration is 10 mM; and is preferably 30 to 140%, more preferably 40 to 130% and even more preferably 50 to 120% when the substrate concentration is 50 mM.

When the activity at 45° C. is defined as 100%, the preferable range of the activity at 10 to 45° C. is 20 to 120%. The range is preferably 30 to 120%, more preferably 40 to 120% and even more preferably 50 to 120% when the substrate concentration is 10 mM; and is preferably 30 to 120%, more preferably 30 to 110% and even more preferably 40 to 110% when the substrate concentration is 50 mM.

As to the preferable range of the activity when the activity at 50° C. is defined as 100%, the activity at 10° C. is preferably 25% or more, more preferably 40% or more, even more preferably 50% or more and particularly preferably 60% or more, and the activity at 20° C. is preferably 40% or more, more preferably 50% or more, even more preferably 60% or more and particularly preferably 80% or more when the substrate concentration is 10 mM; and the activity at 10° C. is preferably 25% or more, more preferably 30% or more, even more preferably 40% or more and particularly preferably 45% or more, and the activity at 20° C. is preferably 40% or more, more preferably 50% or more, even more preferably 55% or more and particularly preferably 60% or more when the substrate concentration is 50 mM.

(4) The molecular weight of a polypeptide of the enzyme protein is 60 to 70 kDa.
(5) The optimum temperature is 30 to 45° C.
(6) The optimum pH is 6.0 to 8.0.
(7) The stable pH range is 4.5 to 7.0.
(8) The residual activity after heat treatment at 40° C. for 15 minutes is 70% or more.

The Km value of the glucose dehydrogenase (A) against D-glucose is preferably about 100 to 200 mM. Also, the glucose dehydrogenase (A) is preferably derived from the genus *Dumontinia* and particularly preferably from *Dumontinia tuberosa.*

The glucose dehydrogenase (B) is a flavin-binding glucose dehydrogenase having the following properties (1) to (3) and is particularly preferably one having any one of the following properties (4) to (8).

(1) Activity: it exhibits glucose dehydrogenase activity in the presence of an electron acceptor.
(2) Substrate specificity: it exhibits an activity of 10% or less against maltose, D-galactose, D-fructose, sorbitol, lactose and sucrose, when the activity against D-glucose is defined as 100%.
(3) Temperature characteristics: it exhibits an activity range from 20 to 150% at 10 to 50° C. when the activity at 30° C. is defined as 100%. The preferred range is preferably 30 to 140%, more preferably 40 to 130% and even more preferably 40 to 120% when the substrate concentration is 10 mM; and is preferably 20 to 140%, more preferably 30 to 140% and even more preferably 30 to 130% when the substrate concentration is 50 mM.

When the activity at 45° C. is defined as 100%, the preferable range of the activity at 10 to 45° C. is 20 to 120%. The range is preferably 30 to 120%, more preferably 30 to 110% and even more preferably 40 to 110% when the substrate concentration is 10 mM; and is preferably 25 to 120%, more preferably 25 to 110% and even more preferably 30 to 110% when the substrate concentration is 50 mM.

As to the preferable range of the activity when the activity at 50° C. is defined as 100%, the activity at 10° C. is preferably 25% or more, more preferably 35% or more, even more preferably 40% or more and particularly preferably 45% or more, and the activity at 20° C. is preferably 40% or more, more preferably 50% or more, even more preferably 60% or more and particularly preferably 65% or more when the substrate concentration is 10 mM; and the activity at 10° C. is preferably 25% or more and more preferably 30% or more, and the activity at 20° C. is preferably 40% or more, more preferably 45% or more and even more preferably 50% or more when the substrate concentration is 50 mM.

(4) The molecular weight of a polypeptide of the enzyme protein is 60 to 70 kDa.
(5) The optimum temperature is 35 to 50° C.
(6) The optimum pH is 6.0 to 7.5.
(7) The stable pH range is 4.5 to 7.0.
(8) The residual activity after heat treatment at 40° C. for 15 minutes is 70% or more.

The Km value of the glucose dehydrogenase (B) against D-glucose is preferably about 10 to 40 mM. Also, the glucose dehydrogenase (B) is preferably derived from the genus *Ovulinia* and more preferably from *Ovulinia azaleae.*

The glucose dehydrogenase (C) is a flavin-binding glucose dehydrogenase having the following properties (1) to (3) and is particularly preferably one having any one of the following properties (4) to (8).

(1) Activity: it exhibits glucose dehydrogenase activity in the presence of an electron acceptor.
(2) Substrate specificity: it exhibits an activity of 10% or less against maltose, D-galactose, D-fructose, sorbitol, lactose and sucrose, when the activity against D-glucose is defined as 100%.
(3) Temperature characteristics: it exhibits an activity range from 20 to 150% at 10 to 50° C. when the activity at 30° C. is defined as 100%. The preferred range is preferably 20 to 140%, more preferably 30 to 140% and even more preferably 30 to 130% when the substrate concentration is 10 mM; and is preferably 25 to 150%, more preferably 30 to 150% and even more preferably 35 to 150% when the substrate concentration is 50 mM; the preferable range of the activity at 10 to 45° C. is preferably 35 to 145% when the substrate concentration is 50 mM.

When the activity at 45° C. is defined as 100%, the preferable range of the activity at 10 to 45° C. is 20 to 120%. The range is preferably 25 to 120%, more preferably 25 to 110% and even more preferably 30 to 110% when the substrate concentration is 10 mM; and is preferably 20 to 115%, more preferably 20 to 110% and even more preferably 25 to 110% when the substrate concentration is 50 mM.

As to the preferable range of the activity when the activity at 50° C. is defined as 100%, the activity at 10° C. is preferably 25% or more and more preferably 30% or more, and the activity at 20° C. is preferably 40% or more, more preferably 45% or more, even more preferably 50% or more and particularly preferably 55% or more when the substrate concentration is 10 mM; and the activity at 10° C. is preferably 25% or more, and the activity at 20° C. is preferably 40% or more when the substrate concentration is 50 mM.

(4) The molecular weight of a polypeptide of the enzyme protein is 60 to 70 kDa.
(5) The optimum temperature is 40 to 50° C.
(6) The optimum pH is 5.5 to 7.5.
(7) The stable pH range is 5.0 to 8.0.
(8) The residual activity after heat treatment at 40° C. for 15 minutes is 70% or more.

The Km value of the glucose dehydrogenase (C) against D-glucose is preferably about 10 to 30 mM. Also, the glucose dehydrogenase (C) is preferably derived from the genus *Sclerotinia* and more preferably from *Sclerotinia sclerotiorum.*

The glucose dehydrogenase (D) is a flavin-binding glucose dehydrogenase having the following properties (1) to (3) and is particularly preferably one having any one of the following properties (4) to (8).

(1) Activity: it exhibits glucose dehydrogenase activity in the presence of an electron acceptor.

(2) Substrate specificity: it exhibits an activity of 10% or less against maltose, D-galactose, D-fructose, sorbitol, lactose and sucrose, when the activity against D-glucose is defined as 100%.

(3) Temperature characteristics: it exhibits an activity range from 20 to 150% at 10 to 50° C. when the activity at 30° C. is defined as 100%. The preferred range is preferably 20 to 140%, more preferably 30 to 130% and even more preferably 30 to 120% when the substrate concentration is 10 mM; and is preferably 20 to 140%, more preferably 30 to 130% and even more preferably 40 to 120% when the substrate concentration is 50 mM; the preferable range of the activity at 10 to 45° C. is preferably 40 to 120% when the substrate concentration is 10 mM.

When the activity at 45° C. is defined as 100%, the preferable range of the activity at 10 to 45° C. is 20 to 120%. The range is preferably 30 to 120%, more preferably 40 to 120% and even more preferably 45 to 120% when the substrate concentration is 10 mM; and is preferably 30 to 120%, more preferably 35 to 120% and even more preferably 40 to 120% when the substrate concentration is 50 mM.

As to the preferable range of the activity when the activity at 50° C. is defined as 100%, the activity at 10° C. is preferably 25% or more, and the activity at 20° C. is preferably 40% or more when the substrate concentration is 10 mM; and the activity at 10° C. is preferably 25% or more, and the activity at 20° C. is preferably 40% or more when the substrate concentration is 50 mM.

(4) The molecular weight of a polypeptide of the enzyme protein is 60 to 70 kDa.

(5) The optimum temperature is 30 to 45° C.

(6) The optimum pH is 5.5 to 7.5.

(7) The stable pH range is 4.5 to 7.0.

(8) The residual activity after heat treatment at 40° C. for 15 minutes is 70% or more.

The Km value of the glucose dehydrogenase (D) against D-glucose is preferably about 20 to 50 mM. Also, the glucose dehydrogenase (D) is preferably derived from the genus *Botrytis* and more preferably from *Botrytis fabae.*

The origin from which the glucose dehydrogenase of the present invention is derived is not particularly limited, the origin is preferably filamentous fungi, more preferably filamentous fungi belonging to the order Helotiales, even more preferably filamentous fungi belonging to the family Sclerotiniaceae, particularly preferably filamentous fungi belonging to the genus *Dumontinia*, genus *Ovulinia*, genus *Sclerotinia*, genus *Botrytis* or genus *Ciborinia*, and most preferably *Dumontinia tuberosa, Ovulinia azaleae, Sclerotinia sclerotiorum, Botrytis fabae, Botrytis tulipae* or *Ciborinia camelliae.*

The glucose dehydrogenase of the present invention can be produced, for example, by culturing a microorganism belonging to eukaryotic cell (e.g. filamentous fungi or yeast) having ability of producing the glucose dehydrogenase and by collecting the glucose dehydrogenase from the cultured product.

A generally used microorganism culturing medium may be used for the culture of microorganisms of the present invention and any of synthetic mediums and natural mediums may be used as long as it properly contains carbon sources, nitrogen sources, inorganics and other trace nutrient required for culturing microorganisms. As the carbon source, glucose, sucrose, dextrin, starch, glycerin, syrup etc. may be used. As the nitrogen source, inorganic salts such as ammonium chloride, ammonium nitrate, ammonium sulfate, and ammonium phosphate, amino acids such as DL-alanine and L-glutamic acid, and nitrogen-containing natural products such as peptone, meat extracts, yeast extracts, maltose extracts, and corn steep liquor may be used. As the inorganic products, monosodium phosphate, disodium phosphate, monopotassium phosphate, dipotassium phosphate, magnesium sulfate, ferric chloride etc. may be used.

It is preferable that the culturing for obtaining the glucose dehydrogenase of the present invention be usually performed in an aerobic condition by a method such as shaking culture or aerobic stirring, and preferably performed under the conditions of 20° C. to 50° C. and pH range from 4 to 8. The culturing is preferably performed for a culture time range from 2 days to 10 days. The culture using such a method enables the production and accumulation of a glucose dehydrogenase in a cultured product and particularly, a culture solution. Or, the culture method enables the production and accumulation of a glucose dehydrogenase in cultured microorganisms. Then, as the method of obtaining a glucose dehydrogenase from the cultured product, a usual method for protein purification may be used. This method is, for example, a method in which after microorganisms are cultured, these microorganisms are removed by, for example, centrifugation to obtain the culture supernatant, or a method in which after microorganisms are cultured, the cultured solution is subjected to centrifugation to obtain cultured microorganisms, which are crushed by an appropriate method to obtain a supernatant fluid from the cell homogenate by centrifugation etc. Glucose dehydrogenase contained in the supernatant fluid can be purified by combining adequate operations for purification such as ultrafiltration, salting-out, solvent precipitation, dialysis, ion exchange chromatography, hydrophobic adsorption chromatography, gel filtration, affinity chromatography, and electrophoresis.

In the culturing for obtaining the glucose dehydrogenase of the present invention, the use of a solid medium is allowed. The culture method is not particularly limited, and the culturing may be carried out by static culture or by, for example, roller tube culture or fluidized bed culture in which a culture product is always mixed, the static culture is desirable as a culture unit reduced in capital expenditure. Then, as the method of obtaining a glucose dehydrogenase from the cultured product, a usual protein purification method may be used. Specifically, this purification method may be performed by adding an extracting agent such as water to the cultured product to stir, followed by removing a medium solid content such as bran by a separating method such as centrifugation or filtration to obtain an extraction liquid. On the other hand, the harvesting of accumulated intracellular glucose dehydrogenase may be performed, for example, by grinding the culture product residue obtained after the above extract is obtained, together with abrasives such as sea sand, and then by adding water etc. to extract a glucose dehydrogenase without cells. Or, in order to obtain total glucose dehydrogenase, a method may be performed, for example, in which the whole culture product is ground together with abrasives such as sea sand, water etc. is then added to extract both the cell-free glucose dehydrogenase and the glucose dehydrogenase secreted in the medium by one operation. Glucose dehydrogenase contained in these supernatant fluids can be purified by combining proper purification operations such as ultrafiltration, salting-out, solvent precipitation, dialysis, ion exchange chromatography, hydrophobic adsorption chromatography, gel filtration, affinity chromatography, and electrophoresis.

The inventors of the present invention have further succeeded in the cloning of glucose dehydrogenase genes derived from filamentous fungi belonging to the genus *Dumontinia* (i), genus *Botrytis* (ii), genus *Ovulinia* (iii) and genus *Ciborinia* (iv) among the above glucose dehydrogenases. Particularly, the inventors of the present invention have succeeded in the cloning of glucose dehydrogenase genes derived from *Dumontinia tuberosa, Botrytis tulipae, Ovulinia azaleae* and *Ciborinia camelliae.*

The base sequence of the glucose dehydrogenase gene derived from *Dumontinia* is SEQ ID NO: 1 and the amino acid sequence for which the gene encodes is SEQ ID NO: 2. Also, the amino acid sequence excluding the signal sequence of the glucose dehydrogenase derived from *Dumontinia* is SEQ ID NO: 10 and the base sequence corresponding to the same is SEQ ID NO: 9.

The base sequence of the glucose dehydrogenase gene derived from *Botrytis* is SEQ ID NO: 3 and the amino acid sequence for which the gene encodes is SEQ ID NO: 4. Also, the amino acid sequence excluding the signal sequence of the glucose dehydrogenase derived from *Botrytis* is SEQ ID NO: 12 and the base sequence corresponding to the same is SEQ ID NO: 11.

The base sequence of the glucose dehydrogenase gene derived from *Qvulinia* is SEQ ID NO: 5 and the amino acid sequence for which the gene encodes is SEQ ID NO: 6. Also, the amino acid sequence excluding the signal sequence of the glucose dehydrogenase derived from *Qvulinia* is SEQ ID NO: 14 and the base sequence corresponding to the same is SEQ ID NO: 13.

The base sequence of the glucose dehydrogenase gene derived from *Ciborinia* is SEQ ID NO: 7 and the amino acid sequence for which the gene encodes is SEQ ID NO: 8. Also, the amino acid sequence excluding the signal sequence of the glucose dehydrogenase derived from *Ciborinia* is SEQ ID NO: 16 and the base sequence corresponding to the same is SEQ ID NO: 15.

The glucose dehydrogenase of the present invention has the following amino acid sequence (a), (b) or (c), is a flavin-binding glucose dehydrogenase exhibiting glucose dehydrogenase activity, and is preferably a flavin-binding glucose dehydrogenase consisting of a glycoprotein.

(a) An amino acid sequences represented by SEQ ID NO: 2, 4, 6, 8, 10, 12, 14 or 16.

(b) An amino acid sequence obtained wherein one to several amino acids are substituted, deleted or added in an amino acid sequence represented by SEQ ID NO: 2, 4, 6, 8, 10, 12, 14 or 16.

(c) An amino acid sequence having at least 70%, preferably at least 75%, more preferably at least 80%, even more preferably at least 85%, particularly preferably at least 90% and most preferably at least 95% identity with that represented by SEQ ID NO: 2, 4, 6, 8, 10, 12, 14 or 16.

In this case, the term “several” means preferably 20, more preferably 15, even more preferably 10, even more preferably 5 or particularly preferably 3.

The amino-terminal (N-terminal) of glucose dehydrogenase of the present invention is preferably LSL, STL or VAL, and more preferably LSLT, STLT or VALT.

The glucose dehydrogenase of the present invention is a purified flavin-binding glucose dehydrogenase having an amino acid sequence having at least 60%, preferably at least 65%, more preferably at least 70%, even more preferably at least 75%, even more preferably at least 80%, even more preferably at least 85%, even more preferably at least 90% and particularly preferably at least 95% identity with that represented by SEQ ID NO: 10, 12, 14 or 16, and the following properties (i) to (v):

(i) which oxidizes the first position of the glucose;

(ii) oxygen does not substantially act as an electron acceptor for it;

(iii) stable pH: 4.5 to 7.0;

(iv) which is a glycoprotein; and (v) the molecular weight of the polypeptide moiety of the enzyme is 60 to 70 kDa.

The description “oxygen does not substantially act as an electron acceptor for it” means that the enzyme exhibits its reactivity to oxygen to the extent that no activity is observed by the glucose oxidizing method for measuring enzymatic activity which will be explained later: the reactivity obtained when oxygen is an electron acceptor is preferably 1% or less, more preferably 0.5% or less, even more preferably 0.1% or less, and particularly preferably 0.05% or less when the reactivity obtained in the case of using 2,6-dichlorophenol indophenol as an electron acceptor is 100%.

A polynucleotide in the present invention is one which encodes the glucose dehydrogenase having the above amino acid sequence (a), (b) or (c), and may be either a polynucleotide consisting of a base sequence containing intron or a polynucleotide consisting of a base sequence modified to codon usage corresponding to a host. Moreover, the polynucleotide in the present invention is one represented by the following (d), (e) or (f).

(d) A polynucleotide consisting of a base sequence represented by SEQ ID NO: 1, 3, 5, 7, 9, 11, 13 or 15.

(e) A polynucleotide that hybridizes to a polynucleotide consisting of a base sequence complementary to the base sequence of the polynucleotide of (d) in a stringent condition and encodes a glucose dehydrogenase.

(f) A polynucleotide which is consisting of a base sequence having at least 70%, preferably at least 75%, more preferably at least 80%, even more preferably at least 85%, particularly preferably at least 90% and most preferably 95% identity with that represented by SEQ ID NO: 1, 3, 5, 7, 9, 11, 13 or 15 and encodes a glucose dehydrogenase.

Moreover, (g) a polynucleotide in the present invention is one which is consisting of a base sequence having at least 60%, preferably at least 65%, more preferably at least 70%, even more preferably at least 75%, even more preferably at least 80%, even more preferably at least 85%, even more preferably at least 90% and particularly preferably at least 95% identity with that represented by SEQ ID NO: 9, 11, 13 or 15, is a modified gene obtained by deleting 57 bases from A of the start codon to the 57th base in full-length gene (e.g. SEQ ID NO:1, 3, 5 or 7), and encodes a glucose dehydrogenase. The use of the modified gene enables not only transgenic production using gram negative bacteria such as *E. coli* but also the addition of a signal sequence for preferable secretion.

The identity percentage of an amino acid sequence and base sequence can be calculated using a published or commercially available software including an algorithm that compares the amino acid sequence by using a standard sequence (SEQ ID NOs: 1 to 16 in the present invention) as a query sequence. For example, Maximum Matching of GeneDoc or GENETYX (manufactured by Software Development Co., Ltd.) may be used and they can be used by using default parameters.

As a specific condition described in the description “hybridizes . . . in a stringent condition”, such a condition may be exemplified that the enzyme is incubated at 42° C. in a medium containing 50% formamide, 5×SSC (150 mM sodium chloride, 15 mM trisodium citrate, 10 mM sodium phosphate, 1 mM ethylenediamine tetraacetic acid, pH 7.2), 5×Denhardt’s solution, 0.1% SDS, 10% dextran sulfate, and 100 μg/mL denatured salmon sperm DNA and then, the filter is washed with 0.2×SSC at 42° C.

A genome DNA or RNA can be prepared, for example, from filamentous fungi, preferably a microorganism belonging to the order Helotiales and more preferably a microorganism belonging to the family Sclerotiniaceae by a usual method. The probe and primer can be manufactured based on a known gene sequence of a flavin-binding glucose dehydrogenase besides a gene sequence of a flavin-binding glucose dehydrogenase derived from *Aspergillus terreus* described in WO2006/101239 and a gene sequence of a flavin-binding glucose dehydrogenase derived from *Aspergillus oryzae* described in Patent Document 3. Or, these probes and primers may be manufactured, for example, by cutting a cDNA which is the polynucleotide of the present invention by an adequate restriction enzyme.

The polynucleotide in the present invention can be obtained by using the manufactured plurality of oligonucleotide probes to carryout screening of the above genome DNA library by using a method such as hybridization known to a person skilled in the art. Though the labeling of the prove can be attained by a method known to a person skilled in the art, for example, the radio isotope (RI) method or non-RI method, the non-RI method being preferably used. Examples of the non-RI method may include a fluorescent labeling method, biotin labeling method, and chemiluminescence method, the fluorescent labeling method being preferably used. As the fluorescent material, a cyanine dye (for example, Cy3, Cy5, etc. of Cy Dye TM series), Rhodamine 6G reagent, N-acetoxy-N2-acetylaminofluorene (AAF), AAIF (iodine derivative of AAF) etc. may be used though a fluorescent material which can be bound with the base moiety of the oligonucleotide may be properly selected and used.

The polynucleotide in the present invention may be obtained by the PCR method using a genome DNA as a template. Moreover, the polynucleotide which is a cDNA represented by SEQ ID NO: 1, 3, 5, 7, 9, 11, 13 or 15 can be obtained, for example, by the RT-PCR method using a total RNA or mRNA as a template prepared from the above microorganism. Or, with regard to the coding region of the enzyme including an intron, a cDNA is determined using an analysis software such as GENETYX, thereby making it possible to obtain a polynucleotide from which an intron is deleted by the PCR method. In this case, when a primer is designed, a commercially available software for primer design, for example, Oligo™ [National Bioscience Inc. (manufactured in US)], GENETYX (manufactured by Software Development Co., Ltd.), etc. may be used.

The method of obtaining the polynucleotide in the present invention is not particularly limited, the polynucleotide can be obtained by the following method. A pair of primers represented by SEQ ID NOs: 17 and 18 is used to perform RT-PCR or PCR using the aforementioned RNA or genome DNA as a template to elucidate the internal sequence of a gene encoding for the glucose dehydrogenase of the present invention. A product obtained by the above PCR preferably has 1,100 to 1,300 bp and more preferably 1,150 to 1,200 bp when it contains no intron and 1,200 to 1,250 bp when it contains an intron. Next, using a primer designed from the elucidated internal sequence, the 5'-RACE method and 3'-RACE method are carried out to elucidate sequences near to the start codon and near to stop codon of a gene encoding for the glucose dehydrogenase of the present invention. Subsequently, a primer is designed which can amplify a full-length gene between the start codon and stop codon encoding for the glucose dehydrogenase of the present invention, whereby the polynucleotide in the present invention can be obtained. Or, there is the case where a full-length gene to be elucidated can be amplified using a primer in which the full-length gene of SEQ ID NO: 1, 3, 5 or 7 has been amplified. Moreover, the polynucleotide in the present invention can be obtained by using a primer so designed that a polynucleotide excluding a base sequence encoding for a signal part can be amplified. Or, a PCR product obtained using SEQ ID NOs: 17 and 18 may be used as the above screening probe. Finally, large scale amplification is made by PCR, thereby enabling the production of the polynucleotide according to the present invention.

The polynucleotide in the present invention may be produced by modifying using a known method for introducing mutation, mutagenesis PCR, etc. Also, the polynucleotide may be obtained by the probe hybridization method using an oligonucleotide prepared based on the nucleotide sequence information from a genome DNA or a library of its cDNA. The above polynucleotide can be obtained by variously changing the stringent condition in the hybridization. The stringent condition is defined by salt concentrations, the concentration of an organic solvent (formaldehyde etc.), temperature condition etc. in the hybridization and washing step, and various conditions known to a person skilled in the art as disclosed in, for example, U.S. Pat. No. 6,100,037 may be adopted.

The polynucleotide in the present invention may be synthesized in vitro by known chemically synthesizing method as described in the literatures (Carruthers (1982) Cold Spring Harbor Symp. Quant. Biol. 47: 411-418; Adams (1983) J. Am. Chem. Soc. 105:661; Belousov (1997) Nucleic Acid Res. 25: 3440-3444; Frenkel (1995) Free Radic. Biol. Med. 19: 373-380; Blommers (1994) Biochemistry 33: 7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066).

The recombinant vector according to the present invention is a cloning vector or expression vector and an appropriate vector is used corresponding to, for example, the type of polynucleotide as an insert and its purpose of use. For example, when a flavin-binding glucose dehydrogenase is produced by using a cDNA or its ORF region as an insert, an expression vector for in vitro transcription, or expression vectors suitable for prokaryotic cells such as *E. coli* and grass *bacillus*, and eukaryotic cells including filamentous fungi such as yeast and mold, insect cells, and mammal cells may be used.

For the transformed cell in the present invention, for example, prokaryotic cell such as *E. coli* and grass *bacillus*, and eukaryotic cell such as fungi (e.g. yeast and mold), insect cell and mammal cell may be used. The transformed cell is preferably fungi belonging to different species from wild type strain and more preferably a fungi belonging to genus *Aspergillus*. These transformed cells can be prepared by introducing a recombinant vector into cells by a known method such as electroporation, calcium phosphate method, liposome method and DEAE dextran method. Specific examples of the recombinant vector and the transformed cell include the recombinant vectors shown in the examples below, transformed *E. coli*, transformed yeast and transformed filamentous fungi by the vectors.

When a DNA is expressed by microorganisms such as *E. coli* to produce the flavin-binding glucose dehydrogenase of the present invention, an expression vector having an origin, promoter, ribosome binding site, DNA cloning site, terminator sequence etc. which are replicable in microorganisms is recombined with the aforementioned polynucleotide to prepare a recombinant expression vector. Then, if a host cell is transformed by this expression vector and then, the obtained transformant is cultured, a flavin-binding glucose dehydrogenase can be mass-produced by microorganisms. In this case, if a start codon and a stop codon are added to positions before and behind an optional coding region to express, a flavin-binding glucose dehydrogenase fragment containing a desired region can be obtained. Or, the enzyme can be expressed as a fusion protein combined with other protein. When this fusion protein is cleaved by a proper protease, an intended flavin-binding glucose dehydrogenase can be obtained. As the *E. coli* expression vector, a pUC system, pBluescriptII, pET expression system, pGEX expression system and pCold expression system may be exemplified.

Or, when the flavin-binding glucose dehydrogenase is produced by using eukaryotic cells to express, the aforementioned polynucleotide is introduced into a eukaryotic cell expression vector having a promoter, splicing region, poly (A) addition site etc. to form a recombinant vector and the obtained recombinant vector is introduced into the eukaryotic cells, and thus, the flavin-binding glucose dehydrogenase can be produced by the eukaryotic cells. The enzyme is preferably a glycoprotein and the transformed cells expressing the enzyme are preferably eukaryotic cells. The enzyme can be maintained either in cells in the state of a plasmid or in the state incorporated into a genome. As the expression vector, pKA1, pCDM8, pSVK3, pSVL, pBK-CMV, pBK-RSV, EBV vector, pRS and pYE82 may be exemplified. Also, if pIND/V5-His, pFLAG-CMV-2, pEGFP-N1, pEGFPC1, etc. is used as an expression vector, the flavin-binding glucose dehydrogenase can also be expressed as a fusion protein with various tags such as a His-tag, FLAG-tag and GFP added thereto. As the eukaryotic cell, any eukaryotic cell may be used as long as it can express the flavin-binding glucose dehydrogenase though mammalian cultured cells such as a monkey kidney cell COS-7 and Chinese hamster ovary cell CHO, budding yeast, fission yeast, filamentous fungi, silkworm cell and *Xenopus oocyte* are generally used. A known method such as electroporation, calcium phosphate method, liposome method or DEAE dextran method may be used to introduce an expression vector into eukaryotic cells.

When the flavin-binding glucose dehydrogenase is expressed in vitro to produce, the aforementioned polynucleotide is inserted into a vector having a promoter with which a RNA polymerase can be bound to form a recombinant vector and this vector is added to an in-vitro translation system such as a rabbit reticulocyte lysate or wheat germ extract containing a RNA polymerase corresponding to the promoter, whereby the flavin-binding glucose dehydrogenase can be produced in vitro. As the promoter with which a RNA polymerase can be bound, T3, T7 and SP6 may be exemplified. As the vector containing these promoters, pKA1, pCDM8, pT3/T718, pT7/319 and pBluescript II may be exemplified.

The glucose dehydrogenase of the present invention may be a synthetic glucose dehydrogenase or recombinant glucose dehydrogenase obtained by genetic engineering. A person skilled in the art can easily obtain the glucose dehydrogenase based on the disclosure of the present invention. For example, a glucose dehydrogenase can be obtained by extracting from microorganisms containing filamentous fungi or natural products such as animals and vegetables or by a synthetic method based on its amino acid sequence or the base sequence of a gene encoding for this amino acid sequence. With regard to a recombination production method, on the other hand, the polynucleotide according to the present invention is inserted into a known expression vector such as commercially available expression vectors and the obtained plasmid is used to transform a host such as *E. coli* or filamentous fungi. Then, the transformed product is cultured to obtain an intended glucose dehydrogenase from the cultured product, for industrial-scale production of a glucose dehydrogenase. Because the glucose dehydrogenase of the present invention is preferably a glycoprotein as mentioned above, it is preferable to culture eukaryotic cells such as filamentous fungi or yeast (recombinant) and to extract a glucose dehydrogenase from the cultured product. Moreover, it is preferable to utilize a gene encoding a wild type secretion signal sequence or a gene encoding a secretion signal sequence homologous to a gene encoding a secretion signal sequence in the vector or host, and preferably a gene encoding a secretion signal sequence exhibiting high secretory efficiency, to produce an enzyme by secretion to outside the cell bodies (in the medium), thereby making possible to produce the enzyme more efficiently than in the case of producing the enzyme inside the cell bodies.

In the measurement of the activity of the enzyme, the enzyme is properly diluted to adjust the final concentration of preferably 0.15 to 0.6 unit/mL prior to use. In this case, the enzymatic activity unit is an enzymatic activity for oxidizing 1 μmol of glucose for one minute. The enzymatic activity of the glucose dehydrogenase (GLD) of the present invention may be measured by the following method.

(Method for Measuring Enzymatic Activity)

Each solution was mixed according to the following procedures to measure the absorbance, thereby examining GLD activity.

1.00 mL of a 100 mM potassium phosphate buffer solution (pH 6.0), 1.00 mL of a 1M D-glucose solution, 0.61 mL of ultrapure water, 0.14 mL of 3 mM 2,6-dichlorophenol indophenol (hereinafter referred to as DCIP), and 0.20 mL of 3 mM 1-methoxy-5-methylphenaziummethyl sulfate (hereinafter referred to as 1-m-PMS) were mixed and the mixture was kept at 37° C. for 10 minutes. Then, 0.05 mL of an enzyme sample was added to the mixture to start a reaction. The amount (ΔA600) of reduction in light absorbance per minute at 600 nm along with the progress of the enzymatic reaction was measured for 5 minutes from the start of the reaction to calculate GLD activity from the straight line part according to the equation 1. At this time, in the measurement of GLD activity, the amount of an enzyme reducing 1 μmol of DCIP at 37° C. and a pH of 6.0 for one minute was defined as 1 U.

[Math. Formulation 1]

$$\text{Enzymatic activity (U/mL)} = \frac{-(\Delta A600 - \Delta A600\ \text{blank}) \times 3.0 \times df}{(10.8 \times 1.0 \times 0.05)}$$

In the above formula, 3.0 represents the amount (mL) of reaction reagent+oxygen solution, 10.8 represents the molar absorption coefficient ($mM^{-1}\ cm^{-1}$) of DCIP at a pH of 6.0, 1.0 represents the optical path length (cm) of a cell, 0.05 represents the amount (mL) of the oxygen solution, ΔA600 blank represents a reduction in the amount of light absorbance per minute at 600 nm when the solution used to dilute the enzyme is added in place of the enzyme solution to start a reaction, and df represents a dilution ratio.

The glucose dehydrogenase of the present invention may be used for, though not particularly limited to, measurement of glucose, measuring reagents, biosensors or bio-batteries. Among the glucose dehydrogenases of the present invention, glucose dehydrogenases which are glycoproteins are preferably used in each application. Specifically, because the glucose dehydrogenase of the present invention has high specificity to glucose, also maintains high activity even at ambient temperature, and is not affected by dissolved oxygen in the measurement, it is useful to measure glucose concentration and especially, blood glucose concentration. The concentration of glucose in a test sample can be measured by a process of bringing the test sample containing glucose, for example, blood into contact with the glucose dehydrogenase of the present invention. If a glucose measuring method in which the pH in the measurement is 5.0 to 9.0 is used, the reactivity of the enzyme is high.

The glucose dehydrogenase of the present invention may be used for a glucose measuring reagent. The measuring reagent may be appropriately formulated with bovine serum albumin (BSA) or egg albumin, sugars or sugar alcohols exhibiting no reactivity to the enzyme, carboxyl group-containing compound, alkali earth metal compound, ammonium salt, heat stabilizer selected from the group consisting of sulfates, proteins etc., or optional components such as a buffer agent, which are known to a person skilled in the art, thereby making it possible to improve the heat stability and storage stability of the enzyme and reagent component. If the pH of the measuring reagent is preferably 4.0 to 7.5, preferable storage stability is obtained. Moreover, the measuring reagent may contain known materials which prevent the adverse influence of foreign materials existing in the test sample and affecting the measurement. The method of producing the measuring reagent is not particularly limited, the measuring reagent may be prepared preferably at a pH range from 4.0 to 7.5.

The glucose dehydrogenase of the present invention may be used for a biosensor. A biosensor according to the present invention may be one in which the glucose dehydrogenase of the present invention is used as an enzyme in a reaction layer. When the pH of the reaction layer is preferably 4.0 to 7.5, the sensor can be stored stably. For example, the biosensor is manufactured by utilizing a method such as screen printing or vapor deposition to form an electrode system on an insulating substrate and further by providing a measuring reagent containing an oxidoreductase and electron acceptor. When a sample solution containing a substrate is brought into contact with the measuring reagent of the biosensor, the measuring reagent is dissolved to undergo the reaction between the enzyme and the substrate, followed by the reduction of an electron acceptor. After the enzymatic reaction is finished, the reduced electron acceptor is oxidized electrochemically. At this time, this biosensor can measure the substrate concentration in the sample solution from value of current for oxidation. Besides, a biosensor having a system detecting developed color intensity or pH variation may be prepared. These biosensors enable the measurement of various materials by selecting an enzyme containing a substrate which is a subject material for measurement. For example, when the glucose dehydrogenase of the present invention is selected as an enzyme, a glucose sensor that measures glucose concentration in a sample solution can be manufactured.

As the electron acceptor of the biosensor, a material superior in electron transferability may be used. The material superior in electron transferability usually means chemical materials or proteinaceous electron mediators which are called "electron carriers", "mediators" or "oxidizing and reducing mediators". As these chemical materials corresponding to the above materials, the electron carriers and oxidizing and reducing mediators exemplified in JP-A-2002-526759 etc. may be utilized.

Moreover, the glucose dehydrogenase of the present invention may be used in bio-batteries. The bio-battery according to the present invention is constituted of an anode electrode undergoing an oxidation reaction and a cathode electrode undergoing a reducing reaction and, if necessary, contains an electrolyte layer separating the anode from the cathode. An enzyme electrode including the above electron mediator and glucose oxidoreductase, or the above fusion body is used as the anode electrode to draw electrons generated by oxidizing the substrate from the electrode and also to generate protons. For the cathode side, on the other hand, an enzyme which is usually used for a cathode electrode may be used, and for example, laccase, ascorbate oxidase or bilirubin oxidase is used to undergo a reaction between the protons generated on the anode side and oxygen to produce water. As the electrode, for example, a carbon, gold or platinum electrode which is usually used for a bio-battery may be used.

Various technologies used to carry out the present invention, except for, particularly, technologies indicated by citation, can be easily and surely carried out by a person skilled in the art, based on known prior art documents etc. For example, genetic engineering and molecular biological technologies can be carried out by the methods described in Sambrook and Maniatis, in Molecular Cloning—A Laboratory Manual, Cold Spring Harbor Laboratory Press, New York, 1989; Ausubel, F. M. et al., Current Protocols in Molecular Biology, John Wiley & Sons, New York, N.Y., 1995, methods described in the literatures cited there, substantially the same methods as the above methods or their modified methods. Moreover, the terms in this invention are basically based on IUPAC-IUB Commission on Biochemical Nomenclature, or based on the meaning of terms conventionally used in the technical fields.

EXAMPLES

The present invention will be exemplified by way of examples, which are however not intended for limiting the present invention within the spirit of the present invention. Also, the content described in the documents cited in this specification constitutes a part of disclosures of this specification. The quantitative measurement of glucose dehydrogenase activity in the following examples was performed according to the aforementioned method.

Example 1

Preparation of the Flavin-Binding Glucose Dehydrogenase (GLD) of the Present Invention The screening of GLD-producing microorganism was performed using a total of about 3,800 strains consisting of strains of microorganism isolated from the natural world and strains procured from Culture Collection (National Institute of Technology and Evaluation) and as a result, the inventors of the present invention confirmed GLD activity in culture filtrates of *Dumontinia tuberosa* NBRC30254, *Ovulinia azaleae* NBRC6610, *Sclerotinia sclerotiorum* NBRC9395, *Sclerotinia sclerotiorum* NBRC103652, *Botrytis fabae* NBRC5895, *Botrytis fabae* NBRC7171, *Botrytis tulipae* NBRC5896 and *Ciborinia camelliae* NBRC103663.

Purification of GLD Derived from Microorganisms of the Genus *Dumontinia*: Glucose Dehydrogenase (A)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 cm2 of *Dumontinia tuberosa* NBRC30254 cultured in advance on a plate, for 2 minutes and then, subjected to rotational shaking culture performed at 25° C. at 100 rpm for 3 days. This medium was used as a seed medium and 3.5 L of the above medium put into a 5 L jar fermenter (five jar fermenters) and treated for autoclave was inoculated with 0.05 L of the seed culture, followed by culturing at 25° C., at 300 rpm and a rate of 1 v/v/m for 7 days. After the culturing was finished, 17.5 L of the cultured solution was filtered with a filter cloth to harvest the filtrate. Then, the obtained filtrate was subjected to centrifugation (7,000×g, 30 minutes) to harvest the supernatant, which was then subjected to suction filtration using a membrane filter (manufactured by Advantech Co., Ltd., 10 μm) to obtain the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 50% saturation to precipitate an unnecessary protein. The enzyme solution was allowed to stand at 4° C. overnight and then subjected to centrifugation (7,000×g, 30 minutes) to harvest the supernatant.

This supernatant was made to flow through a Butyl Toyopearl 650C (trademark, manufactured by TOSOH CORPORATION) column (ϕ 3.00 cm×20.0 cm) equilibrated in advance with a buffer solution A1 (50 mM potassium phosphate buffer solution, 50% saturated ammonium sulfate, pH 6.0). After the column was washed with the buffer solution A1, a protein was eluted with a linear gradient of a buffer solution B1 (50 mM potassium phosphate buffer solution, pH 6.0) in the buffer solution A1. Among the eluted protein, an active fraction was concentrated, then dialyzed against a buffer solution C1 (1 mM potassium phosphate buffer solution, pH 6.0), and made to flow through a DEAE Cellfine A-500m (trademark, manufactured by JNC Corporation) column (ϕ 2.10 cm×22.0 cm) equilibrated in advance with the buffer solution C1. After the column was washed with the buffer solution C1, a protein was eluted with a linear gradient of a buffer solution D1 (250 mM potassium phosphate buffer solution, pH 6.0) in the buffer solution C1. Among the eluted protein, an active fraction was concentrated, then dialyzed against the buffer solution C1, and made to flow through a DEAE Cellfine A-500m (trademark, manufactured by JNC Corporation) column (ϕ 1.00 cm×12.7 cm) equilibrated in advance with the buffer solution C1. After the column was washed with the buffer solution C1, a protein was eluted with a buffer solution E1 (40 mM potassium phosphate buffer solution, pH 6.0), a buffer solution F1 (70 mM potassium phosphate buffer solution, pH 6.0) and a buffer solution G (80 mM potassium phosphate buffer solution, pH 6.0) stepwise. Among the eluted protein, an active fraction was concentrated, then dialyzed against a buffer solution H (50 mM potassium phosphate buffer solution, 0.2 N sodium chloride, pH 6.0), and made to flow through a TSKgel-G3000SW (trademark, manufactured by TOSOH CORPORATION) column (ϕ 2.15 cm×60.0 cm) equilibrated in advance with the buffer solution H. Among the eluted protein, an active fraction was concentrated and desalted to obtain a purified enzyme of GLD derived from the genus *Dumontinia* substituted with water. Hereinafter the purified enzyme of GLD derived from the genus *Dumontinia* is abbreviated as DuGLD.

Example 2

Purification of GLD Derived from Microorganisms of the Genus *Ovulinia*: Glucose Dehydrogenase (B)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 cm2 of *Ovulinia azaleae* NBRC6610 cultured in advance on a plate, for 2 minutes and then, subjected to rotational shaking culture performed at 25° C. at 100 rpm for 3 days. This medium was used as a seed medium and 3.5 L of the above medium put into a 5 L jar fermenter (five jar fermenters) and treated for autoclave was inoculated with 0.05 L of the seed culture, followed by culturing at 25° C., at 300 rpm and a rate of 1 v/v/m for 4 days. After the culturing was finished, 17.5 L of the cultured solution was filtered with a filter cloth to harvest the filtrate. Then, the obtained filtrate was subjected to centrifugation (7,000×g, 30 minutes) to harvest the supernatant, which was then subjected to suction filtration using a membrane filter (manufactured by Advantech Co., Ltd., 10 μm) to obtain the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 60% saturation to precipitate an unnecessary protein. The enzyme solution was allowed to stand at 4° C. overnight and then subjected to centrifugation (7,000×g, 30 minutes) to harvest the supernatant.

This supernatant was made to flow through a Butyl Toyopearl 650C (trademark, manufactured by TOSOH CORPORATION) column (ϕ 2.20 cm×21.3 cm) equilibrated in advance with a buffer solution A2 (50 mM potassium phosphate buffer solution, 60% saturated ammonium sulfate, pH 6.0). After the column was washed with the buffer solution A2, a protein was eluted with a linear gradient of a buffer solution B1 (50 mM potassium phosphate buffer solution, pH 6.0) in the buffer solution A2. Among the eluted protein, an active fraction was concentrated, then dialyzed against a buffer solution C1 (1 mM potassium phosphate buffer solution, pH 6.0), and made to flow through a DEAE Cellfine A-500m (trademark, manufactured by JNC Corporation) column (ϕ 2.20 cm×10.8 cm) equilibrated in advance with the buffer solution C1. After the column was washed with the buffer solution C1, a protein was eluted with a linear gradient of a buffer solution D2 (150 mM potassium phosphate buffer solution, pH 6.0) in the buffer solution C1. Among the eluted protein, an active fraction was concentrated, then dialyzed against a buffer solution H (50 mM potassium phosphate buffer solution, 0.2 N sodium chloride, pH 6.0), and made to flow through a TSKgel-G3000SW (trademark, manufactured by TOSOH CORPORATION) column (ϕ 2.15 cm×60.0 cm) equilibrated in advance with the buffer solution H. Among the eluted protein, an active fraction was concentrated and desalted to obtain a purified enzyme of GLD derived from the genus *Ovulinia* substituted with water. Hereinafter the purified enzyme of GLD derived from the genus *Ovulinia* is abbreviated as OvGLD.

Example 3

Purification of GLD Derived from Microorganisms of the Genus *Sclerotinia*: Glucose Dehydrogenase (C)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 cm2 of *Sclerotinia sclerotiorum* NBRC103652 cultured in advance on a plate, for 2 minutes and then, subjected to rotational shaking culture performed at 25° C. at 100 rpm for 3 days. This medium was used as a seed medium and 3 L of the above medium put into a 5 L jar fermenter (five jar fermenters) and treated for autoclave was inoculated with 0.05 L of the seed culture, followed by culturing at 25° C., at 400 rpm and a rate of 1 v/v/m for 6 days. After the culturing was finished, 15 L of the cultured solution was filtered with a filter cloth to harvest the filtrate. Then, the obtained filtrate was subjected to centrifugation (5,000×g, 15 minutes) to harvest the supernatant, which was then subjected to suction filtration using a membrane filter (manufactured by Advantech Co., Ltd., 10 μm) to obtain the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 40% saturation to precipitate an unnecessary protein. The enzyme solution was allowed to stand at 4° C. overnight and then subjected to centrifugation (5,000×g, 15 minutes) to harvest the supernatant.

This supernatant was made to flow through a Butyl Toyopearl 650C (trademark, manufactured by TOSOH CORPORATION) column (ϕ 6.00 cm×5.70 cm) equilibrated in advance with a buffer solution A3 (50 mM potassium phosphate buffer solution, 40% saturated ammonium sulfate, pH 7.0). After the column was washed with the buffer solution A3, a protein was eluted with a linear gradient of a buffer solution B2 (50 mM potassium phosphate buffer solution, pH 7.0) in the buffer solution A3. Among the eluted protein, an active fraction was concentrated, then dialyzed against a buffer solution C2 (1 mM potassium phosphate buffer solution, pH 7.0), and made to flow through a DEAE Cellfine A-500m (trademark, manufactured by JNC Corporation) column (ϕ 2.00 cm×10.2 cm) equilibrated in advance with the buffer solution C2. After the column was washed with the buffer solution C2, a protein was eluted with linear gradient of a buffer solution D3 (500 mM potassium phosphate buffer solution, pH 7.0) in the buffer solution C2. Among the eluted protein, an active fraction was concentrated, then dialyzed against a buffer solution E2 (20 mM potassium phosphate buffer solution, pH 7.0), and made to flow through a DEAE Cellfine A-500m (trademark, manufactured by JNC Corporation) column (ϕ 1.00 cm×12.7 cm) equilibrated in advance with the buffer solution E2. After the column was washed with the buffer solution E2, a protein was eluted with a linear gradient of a buffer solution F2 (100 mM potassium phosphate buffer solution, pH 7.0) in the buffer solution E2. Among the eluted protein, an active fraction was concentrated and desalted to obtain a purified enzyme of GLD derived from the genus *Sclerotinia* substituted with water. Hereinafter the purified enzyme of GLD derived from the genus *Sclerotinia* is abbreviated as ScGLD.

Example 4

Purification of GLD Derived from Microorganisms of the Genus *Botrytis*: Glucose Dehydrogenase (D)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 cm2 of *Botrytis fabae* NBRC7171 cultured in advance on a plate, for 2 minutes and then, subjected to rotational shaking culture performed at 25° C. at 130 rpm for 4 days. This medium was used as a seed medium and 3 L of the above medium put into a 5 L jar fermenter (five jar fermenters) and treated for autoclave was inoculated with 0.05 L of the seed culture, followed by culturing at 25° C., at 400 rpm and a rate of 1 v/v/m for 4 days. After the culturing was finished, 15 L of the cultured solution was filtered with a filter cloth to harvest the filtrate. Then, the obtained filtrate was subjected to centrifugation (5,000×g, 15 minutes) to harvest the supernatant, which was then subjected to suction filtration using a membrane filter (manufactured by Advantech Co., Ltd., 10 μm) to obtain the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 50% saturation to precipitate an unnecessary protein. The enzyme solution was allowed to stand at 4° C. overnight and then subjected to centrifugation (5,000×g, 15 minutes) to harvest the supernatant.

This supernatant was made to flow through a Butyl Toyopearl 650C (trademark, manufactured by TOSOH CORPORATION) column (ϕ 6.0 cm×11.3 cm) equilibrated in advance with a buffer solution A4 (20 mM sodium acetate buffer solution, 50% saturated ammonium sulfate, pH 5.0). After the column was washed with the buffer solution A4, a protein was eluted with a linear gradient of a buffer solution B3 (20 mM sodium acetate buffer solution, pH 5.0) in the buffer solution A4. Among the eluted protein, an active fraction was concentrated, then dialyzed against a buffer solution C3 (1 mM sodium acetate buffer solution, pH 5.0), and made to flow through a SP Toyopearl 650M (trademark, manufactured by TOSOH CORPORATION) column (ϕ 4.6 cm×11.4 cm) equilibrated in advance with the buffer solution C3 to elute a protein with a buffer solution D4 (100 mM sodium acetate buffer solution, pH 5.0). The transmitted active fraction was combined with the active fraction eluted after adsorbed and these fractions were concentrated and dialyzed against the buffer solution C3. Then, the dialyzed solution was made to flow through a DEAE Cellfine A-500m (trademark, manufactured by JNC Corporation) column (ϕ 4.6 cm×12.0 cm) equilibrated in advance with the buffer solution C3. After the column was washed with the buffer solution C3, a protein was eluted with a linear gradient of a buffer solution E3 (200 mM sodium acetate buffer solution, pH 5.0) in the buffer solution C3. Among the eluted protein, an active fraction was concentrated and desalted to obtain a purified enzyme of GLD derived from the genus *Botrytis* substituted with water. Hereinafter the purified enzyme of GLD derived from the genus *Botrytis* is abbreviated as BoGLD.

Example 5

Cloning 1 of a GLD Gene Derived from Microorganisms of the Genus *Dumontinia*

(1) Culturing of Microorganism

A liquid medium consisting of 1% (W/V) of glucose (manufactured by Nacalai Tesque, Inc.), 2% (W/V) of defatted soybean (manufactured by Showa Sangyo Co., Ltd.), 0.5% (W/V) of a corn steep liquor (manufactured by San-ei Sucrochemical Co., Ltd.), 0.1% (W/V) of magnesium sulfate heptahydrate (manufactured by Nacalai Tesque, Inc.) and water was adjusted to pH 6.0. 150 mL of the liquid medium were added into a 500 mL of Sakaguchi flask and treated at 121° C. for 20 minutes for autoclave. The liquid medium after cooled was inoculated with *Dumontinia tuberosa* NBRC30254 strains and shake-cultured at 15° C. for 90 hr and then, wet cells were harvested by using a bleached cloth.

(2) Isolation of a Total RNA 200 mg of the wet cells obtained in the above (1) was frozen at −80° C. and then, 100 μg of a total RNA was extracted with ISOGEN II (trademark, manufactured by NIPPON GENE CO., LTD.).

(3) Preparation of a cDNA Library

A cDNA library was prepared from the total RNA by reverse transcription using a reverse transcriptase and an oligo dT primer with an adapter sequence. As the reaction reagent, a "SMARTer RACE cDNA Amplification kit" (manufactured by TAKARA BIO INC.) was used and the reaction was run in a condition according to the protocol described in an instruction manual.

(4) Cloning of a GLD Gene

A GLD gene was PCR-amplified using, as a template, the cDNA library obtained in the above (3). The primer was designed by analyzing a consensus sequence from a plurality of GLD sequences which had been already clarified by the inventors of the present invention and by using a degenerate base such that even a GLD sequence having less homology is amplified based on the consensus sequence. Finally, a primer pair represented by the following SEQ ID NOs: 17 and 18 was used to perform PCR and as a result, a band corresponding to about 1,200 bp length was confirmed. The DNA fragment was purified to perform ligation with a T-vector PMD20 (trademark, manufactured by TAKARA BIO INC.) by using a DNA Ligation Kit (trademark, manufactured by TAKARA BIO INC.).

An *E. coli* JM109 competent cell (manufactured by TAKARA BIO INC.) was transformed by a known method using the obtained plasmid. A plasmid was extracted from the obtained transformed material and purified by using an illustra plasmid-Prep Mini Spin Kit to determine a gene sequence of the aforementioned amplified DNA contained in the plasmid (1,171 bp). Moreover, the upstream region of the cDNA was amplified by PCR according to the 5' RACE method using a primer represented by the following SEQ ID NO: 19 designed based on the obtained internal sequence and the downstream region of the cDNA was amplified by PCR according to the 3' RACE method using a primer represented by the following SEQ ID NO: 20 to make analysis of the base sequence of the DNA fragment obtained according to the above method, and as a result, the full-length gene sequence of GLD derived from the *Dumontinia tuberosa* NBRC30254 strains represented by the above SEQ ID NO: 1 and having a total chain length of 1,770 bp was clarified. A full-length amino acid sequence for which this gene sequence encodes is represented by the above SEQ ID NO: 2.

```
SEQ ID NO: 17:
5'-GGAACCAGTGGTCTAGTCATCGCAAAYCGKYTATCYGA-3'

SEQ ID NO: 18:
5'-TGGATACTTCCTCTTGCAAATGGTARYARRGCCCAATA-3'
```

-continued

```
SEQ ID NO: 19:
5'-GATCGCCGCAGGGGTGCCTGGTATCG-3'

SEQ ID NO: 20:
5'-GGTGCCGATGTCCCTACTGCAAATGGAG-3'
```

(In the primer sequence, Y is C or T, K is G or T, and R is A or G)

(5) Construction of Plasmid pAFF4/DuGLD

A primer (SEQ ID NOs: 21 and 22) was so designed as to amplify a gene encoding for an amino acid sequence on and after the amino acid at position-17 in the amino acid sequence, that is, an amino acid sequence excluding a predicted signal sequence from the full-length amino acid sequence clarified in the above (4) and PCR was performed using, as a template, the cDNA prepared in the above (3) to obtain a modified gene. At this time, the primer represented by SEQ ID NO: 21 was phosphorylated in advance. The obtained PCR product was treated in advance with NaeI and SalI after treated with SalI and the NaeI cleavage site was introduced into a dephosphorylated secretory plasmid pAFF2 (distributed from National Institute Advanced Industrial Science Technology) to obtain a plasmid pAFF3/DuGLD. Next, PCR was performed using, as a template, pAFF3/DuGLD and a primer pair represented by SEQ ID NOs: 21 and 23. The obtained PCR product was treated with BglII and SphI, inserted into the plasmid pAFF3/DuGLD which was treated in advance with BglII and SphI to obtain a plasmid pAFF4/DuGLD, which was then introduced into *E. coli* JM109 strains to transform. A plasmid was prepared from 5 clones among the obtained transformants and treated with BglII and XbaI, to confirm that fragments having an intended size were confirmed in all clones. With regard to 4 clones among these clones, a plasmid was prepared to determine the sequence of the insert, to confirm intended genes in all plasmids (pAFF4/DuGLD). This pAFF4/DuGLD was used in the following experiments.

```
SEQ ID NO: 21:
5'-GGCAGATCTAGTCCTGACCTTAGTCTAACTTATGACTAT-3'

SEQ ID NO: 22:
5'-CTGCAGGTCGACGCATGCTTAAATATCCTCCTTGATCAAATCTGCCGC-3'

SEQ ID NO: 23:
5'-ACATGCATGCTCTAGATTAAATATCCTCCTTGATCAAATCTGCCGC-3'
```

(6) Transformation of Yeast and Confirmation of GLD Activity

The prepared recombinant vector (pAFF4/DuGLD) was introduced into a host yeast *Saccharomyces cerevisiae* BY4741. Frozen-EZ Yeast Transformation II Kit (manufactured by ZYMO RESEARCH CORP.) was used for the introduction. The obtained transformant was incubated in a 500 mL Sakaguchi flask in which 100 mL of a YPD medium containing 1.00 of a yeast extract (manufactured by BD (Becton, Dickinson and Company)), 2.0% of tripton (manufactured by BD (Becton, Dickinson and Company)) and 2.0% of glucose (manufactured by Wako Pure Chemical Industries, Ltd.) was added and shake-cultured at 30° C. at 120 rpm for 72 hr. After cultured, the medium was centrifuged to harvest the supernatant. The GLD activity of the supernatant was measured using a plate reader (manufactured by Molecular Device Corporation) according to the above GLD activity measuring method. The GLD activity in the supernatant obtained using control strains transformed by a plasmid (pAFF4) into which no GLD gene was inserted was 0.1 U/mL or less, whereas the GLD activity in the supernatant obtained using the strains obtained by transforming pAFF4/DuGLD was 1.6 U/mL, to confirm the GLD activity of the present invention. This cultured supernatant was concentrated using an ultrafiltration concentrating membrane (manufactured by Sartorius K. K., fractional molecular weight 10,000) to obtain a crude enzyme of GLD derived from the genus *Dumontinia.*

Example 6

Cloning 2 of a GLD Gene Derived from Microorganisms of the Genus *Dumontinia*

(1) Construction of Plasmid pSENS/DuGLD and DuGLD-Atsig

Using, as a template, the cDNA prepared in Example 5(3), PCR was performed using a primer pair represented by the following SEQ ID NOs: 34 and 35 designed from the sequence described in SEQ ID NO: 1 to obtain a PCR product including a full-length DuGLD gene. Moreover, PCR for obtaining a DuGLD-Atsig modified gene that encodes a protein substituting the predicted signal sequence of DuGLD with a signal sequence of GLD derived from *Aspergillus terreus* was performed in three stages. As each reverse primer, a primer described in SEQ ID NO: 35 was used. The PCR in the first stage was performed using, as a template, the above PCR product and also using, as a forward primer, a primer (SEQ ID NO: 36) that was so designed as to amplify a gene encoding for an amino acid sequence on and after the amino acid at position-17 in the amino acid sequence, that is, an amino acid sequence excluding a predicted signal sequence of DuGLD. The PCR in the second stage was performed using as a template, the PCR product obtained in the first stage and also using, as a forward primer, a primer shown in SEQ ID NO: 37, and the PCR in the third stage was performed using, as a template, the PCR product obtained in the second stage and also using, as a forward primer, a primer described in SEQ ID NO: 38, to obtain a PCR product including a DuGLD-Atsig modified gene.

```
SEQ ID NO: 34:
5'-(TGACCAATTCCGCAGCTCGTCAAA)ATGAATCATTTACTTCCTGCTTTTGC-3'

SEQ ID NO: 35:
5'-((CGCTTCTAGA))GCATGCTTAAATATCCTCCTTGATCAAATCTGCC-3'

SEQ ID NO: 36:
5'-CCCTGTCCCTGGCAGTGGCGGCACCTTTGAGTCCTGACCTTAGTCTAACTTATG-3'

SEQ ID NO: 37:
5'-ATGTTGGGAAAGCTCTCCTTCCTCAGTGCCCTGTCCCTGGCAGTGGCGGCACCTTTG-3'

SEQ ID NO: 38:
5'-(TGACCAATTCCGCAGCTCGTCAAA)ATGTTGGGAAAGCTCTCCTTCCTCA-3'
```

(Parenthesis: transcription enhancing factor, double parenthesis: pSENS vector sequence, underline portion: restriction enzyme site (SphI), underline portions of SEQ ID NOs: 36, 37 and 38: signal sequences)

Next, the above PCR product including a full-length DuGLD gene and PCR product including a DuGLD-Atsig modified gene were each used as a template to perform PCR by using a primer pair described in SEQ ID NO: 39 and 35, to add a restriction enzyme recognition site and a vector sequence at the N-terminal side.

```
SEQ ID NO: 39:
5'-((CCGTCCTCCAAGTTA))GTCGAC(TGACCAATTCCGCAGCTCGTCAAA)-3'
```

(Parenthesis: transcription enhancing factor, double parenthesis: pSENS vector sequence, underline portion: restriction enzyme site (SalI))

Using an amylase type improved promoter derived from *Aspergillus oryzae* described in a known literature 1 ("Heterologous Gene Expression System of The Genus *Aspergillus*", MINETOKI Toshitaka, Biotechnology, and Agrochemistry, 38, 12, 831-838, 2000), two plasmid vectors for gene-expression were each prepared by binding two PCR products obtained above to the downstream of the promoter. These expressing plasmid vectors were respectively introduced into *E. coli* JM109 strains to transform and each obtained transformant was cultured to extract each plasmid from the collected bacterial body by using an Illustra plasmid-prep MINI Flow Kit (trademark, manufactured by GE Healthcare Japan). The sequence analysis of inserts in each plasmid was made and as a result, a DuGLD gene (SEQ ID NO: 1) or a DuGLD-Atsig modified gene (SEQ ID NO: 48) was confirmed.

(2) Acquisition of a Transformant

Recombinant fungi (*Aspergillus oryzae*) into which a DuGLD gene or DuGLD-Atsig modified gene was introduced were respectively produced using the plasmid extracted in the above (1) according to the method described in a known literature 2 (Biosci. Biotech. Biochem., 61 (8), 1367-1369, 1997) and to the method described in a known literature 3 (GOMI Katsunari, "Gene Operation Technology of yeast cells for sake", Journal of the Brewing Society of Japan, 494-502, 2000). The obtained recombinant strains were each cloned in a Czapek-Dox solid medium. As the host, *Aspergillus oryzae* NS4 strain was used. The strain are available which is bled in Natl. Res. Inst. of Brewing in 1997, utilized for the analysis of transcription factors and bleeding of highly productive strain of various enzymes, and distributed, as described in the known literature 2.

(3) Confirmation of the Activity of GLD Derived from Recombinant Fungi 15 mL of a liquid medium consisting of 2% (w/v) of a Pinedex (trademark, manufactured by Matsutani Chemical Industry Co., Ltd.), 1% (w/v) of tripton (manufactured by BD (Becton, Dickinson and Company)), 0.5% (w/v) of potassium dihydrogenphosphate (manufactured by Nacalai Tesque, Inc.), 0.05% (w/v) of magnesium sulfate heptahydrate (manufactured by Nacalai Tesque, Inc.) and water were added into a thick test tube (22 mm×200 mm) and treated at 121° C. for 20 minutes for autoclave. The liquid medium after cooled was inoculated with the transformant obtained in the above (2) and shake-cultured at 30° C. for 4 days. After the culturing was finished, the medium was centrifuged to harvest the supernatant and the GLD activity (U/mL) of each sample was measured according to the aforementioned GLD activity measuring method to confirm that each sample had GLD activity and that the recombinant fungi transformed by the DuGLD-Atsig modified gene had a productivity of 500 U/mL per 1 mL of the culture solution.

Example 7

Cloning 1 of a GLD Gene Derived from Microorganisms of the Genus *Botrytis*

(1) Culturing of Microorganism

A liquid medium consisting of 1% (W/V) of glucose (manufactured by Nacalai Tesque, Inc.), 2% (W/V) of defatted soybean (manufactured by Showa Sangyo Co., Ltd.), 0.5% (W/V) of a corn steep liquor (manufactured by San-ei Sucrochemical Co., Ltd.), 0.1% (W/V) of magnesium sulfate heptahydrate (manufactured by Nacarai Tesque, Inc.) and water was adjusted to pH 6.0. 150 mL of the liquid medium were added into a 500 mL of Sakaguchi flask and treated at 121° C. for 20 minutes for autoclave. The liquid medium after cooled was inoculated with *Botrytis tulipae* NBRC5896 strains and shake-cultured at 15° C. for 90 hr and then, wet cells were harvested by using a bleached cloth.

(2) Isolation of a Total RNA 200 mg of the wet cells obtained in the above (1) was frozen at −80° C. and then, 100 μg of a total RNA was extracted with ISOGEN II (trademark, manufactured by NIPPON GENE CO., LTD.).

(3) Preparation of a cDNA Library

A cDNA library was prepared from the total RNA by reverse transcription using a reverse transcriptase and an oligo dT primer with an adapter sequence. As the reaction reagent, a “SMARTer RACE cDNA Amplification kit” (manufactured by TAKARA BIO INC.) was used and the reaction was run in a condition according to the protocol described in an instruction manual.

(4) Cloning of a GLD Gene

Using, as a template, the cDNA library obtained in the above (3), a primer pair represented by the following SEQ ID NOs: 17 and 18 was used to perform PCR and as a result, a band corresponding to about 1,200 bp length was confirmed. The DNA fragment was purified to perform ligation with a T-vector PMD20 (trademark, manufactured by TAKARA BIO INC.) by using a DNA Ligation Kit (trademark, manufactured by TAKARA BIO INC.).

A *E. coli* JM109 competent cell (manufactured by TAKARA BIO INC.) was transformed by a known method using the obtained plasmid. A plasmid was extracted from the obtained transformant and purified by using an illustra plasmid-Prep Mini Spin Kit to determine a gene sequence of the aforementioned amplified DNA contained in the plasmid (1,174 bp).

The downstream region of the cDNA was PCR-amplified according to the 3' RACE method using a primer represented by the following SEQ ID NO: 24 designed based on the obtained internal sequence and the GLD sequence which had been already elucidated by the inventors of the present invention and the GLD gene was PCR-amplified using a primer pair represented by the following SEQ ID NOs 25 and 26 to make analysis of the base sequence of the DNA fragment obtained according to the above method, and as a result, the full-length gene sequence of GLD represented by SEQ ID NO: 3 and having a total chain length of 1,773 bp was clarified. A full-length amino acid sequence for which this gene sequence encodes is represented by SEQ ID NO: 4.

```
SEQ ID NO: 24:
5'-CGTTCGTCATGACGCTGGACGAGC-3'

SEQ ID NO: 25:
5'-GAAGATCTATGTATCGTTTACTCTCTACATTTGC-3'

SEQ ID NO: 26:
5'-GCTCTAGACTAAATGTCCTCCTTGATCAAATCTG-3'
```

(5) Transformation of Yeast and Confirmation of GLD Activity

A primer (SEQ ID NOs: 27 and 28) was so designed as to amplify a modified gene encoding for an amino acid sequence on and after the amino acid at position-17 in the amino acid sequence, that is, an amino acid sequence excluding a predicted signal sequence from the full-length amino acid sequence clarified in the above (4) and PCR was performed using, as a template, the cDNA prepared in the above (3) to obtain a modified gene. The PCR product was subjected to agarose electrophoresis, to confirm a band in the vicinity of about 1.8 kb, and therefore, cut by BglII and XbaI after gel-purified using a Wizard SV Gel and PCR Clean-Up System (trademark, manufactured by Promega K. K.). Also, the pAFF4/DuGLD produced in the above (5) in Example 5 was treated with the same restriction enzyme, and the PCR product after treated by the restriction enzyme was ligated to a vector and introduced into *E. coli* JM109 strains to transform. Plasmid DNAs were prepared from five clones among the obtained transformants and treated with BglII and XbaI, to confirm DNA fragments each having an intended size in all clones. With regard to each of these five clones, a plasmid was prepared to determine the sequence of the insert, to confirm intended genes in each plasmid (pAFF4/BotGLD).

```
SEQ ID NO: 27:
5'-GAAGATCTAGCACCGACTCTACTTTAACTTATG-3'

SEQ ID NO: 28:
5'-GCTCTAGACTACATGTCTTCCTTGATCAAATCTGC-3'
```

The recombinant vector (pAFF4/BotGLD) was introduced into host yeast *Saccaromyces* cerevisiae BY4741. A Frozen-EZ Yeast Transformation II kit (trademark, manufactured by ZYMO RESEARCH CORP.) was used for the introduction. The obtained transformant was incubated in a 500 mL Sakaguchi flask in which 100 mL of a YPD medium containing 1.0% of a yeast extract (manufactured by BD (Becton, Dickinson and Company)), 2.0% of tripton (manufactured by BD (Becton, Dickinson and Company)) and 2.0% of glucose (manufactured by Wako Pure Chemical Industries, Ltd.) was added and shake-cultured at 30° C. at 120 rpm for 72 hr. After cultured, the medium was centrifuged to harvest the supernatant. The GLD activity of the supernatant was measured using a plate reader according to the above GLD activity measuring method. The GLD activity in the supernatant obtained using control strains was 0.1 U/mL or less, whereas the GLD activity of the supernatant obtained using the strains transformed from pAFF4/BotGLD was 2.6 U/mL, to confirm the GLD activity of the present invention.

Example 8

Cloning 2 of a GLD Gene Derived from Microorganisms of the Genus *Botrytis*

(1) Construction of Plasmid pSENS/BotGLD and BotGLD-Atsig

Using, as a template, the cDNA prepared in Example 7 (3), PCR was performed using a primer pair represented by the following SEQ ID NOs: 40 and 41 designed from the sequence described in SEQ ID NO: 3 to obtain a PCR product including a full-length BotGLD gene. Moreover, PCR for obtaining a BotGLD-Atsig modified gene that encodes a protein substituting the predicted signal sequence of BotGLD with a signal sequence of GLD derived from *Aspergillus terreus* was performed in three stages. As each reverse primer, a primer described in SEQ ID NO: 41 was used. The PCR in the first stage was performed using, as a template, the above PCR product and also using, as a forward primer, a primer (SEQ ID NO: 42) so designed as to amplify a gene encoding for an amino acid sequence on and after the amino acid at position-17 in the amino acid sequence, that is, an amino acid sequence excluding a predicted signal sequence of BotGLD. The PCR in the second stage was performed using as a template, the PCR product obtained in the first stage and also using, as a forward primer, a primer shown in SEQ ID NO: 37, and the PCR in the third stage was performed using, as a template, the PCR product obtained in the second stage and also using, as a forward primer, a primer described in SEQ ID NO: 38, to obtain a PCR product including a BotGLD-Atsig modified gene.

SEQ ID NO: 40:
5'-(TGACCAATTCCGCAGCTCGTCAAA)ATGTATCGTTTACTCTCTACATTTGC-3'

SEQ ID NO: 41:
5'-((CGCTTCTAGA))GCATGCCTAAATGTCCTCCTTGATCAAATCTGC-3'

SEQ ID NO: 42:
5'-CCCTGTCCCTGGCAGTGGCGGCACCTTTGAGCACCGACTCTACTTTAACTTATG-3'

(Parenthesis: transcription enhancing factor, double parenthesis: pSENS vector sequence, underline portion: restriction enzyme site (SphI), underline portions of SEQ ID NO: 42: At signal sequences)

Next, the above PCR product including a full-length BotGLD gene and PCR product including a BotGLD-Atsig modified gene were each used as a template to perform PCR by using a primer pair described in SEQ ID NOs: 39 and 41, to add a restriction enzyme recognition site and a vector sequence at the N-terminal side.

Using an amylase type improved promoter derived from *Aspergillus oryzae* described in a known literature 1 ("Heterologous Gene Expression System of The Genus *Aspergillus*", MINETOKI Toshitaka, Biotechnology, and Agrochemistry, 38, 12, 831-838, 2000), two plasmid vectors which were gene-expressible were each prepared by binding two PCR products obtained above to the downstream of the promoter. These expressing plasmid vectors were respectively introduced into *E. coli* JM109 strains to transform and each obtained transformant was cultured to extract each plasmid from the collected bacterial body by using an Illustra plasmid-prep MINI Flow Kit (trademark, manufactured by GE Healthcare Japan). The sequence analysis of inserts in each plasmid was made and as a result, a BotGLD gene (SEQ ID NO: 3) or a BotGLD-Atsig modified gene (SEQ ID NO: 50) was confirmed.

(2) Acquisition of a Transformant

Recombinant fungi (*Aspergillus oryzae*) into which a BotGLD gene or BotGLD-Atsig modified gene was introduced were respectively produced using the plasmid extracted in the above (1) according to the method described in a known literature 2 and literature 3. The obtained recombinant strains were each refined in a Czapek-Dox solid medium. As the host, *Aspergillus oryzae* NS 4 strain was used.

(3) Confirmation of the Activity of GLD Derived from Recombinant Fungi 15 mL of a liquid medium consisting of 2% (w/v) of a Pinedex (trademark, manufactured by Matsutani Chemical Industry Co, Ltd.), 1% (w/v) of tripton (manufactured by BD (Becton, Dickinson and Company)), 0.5% (w/v) of potassium dihydrogenphosphate (manufactured by Nacalai Tesque, Inc.), 0.05% (w/v) of magnesium sulfate heptahydrate (manufactured by Nacalai Tesque, Inc.) and water were added into a thick test tube (22 mm×200 mm) and treated at 121° C. for 20 minutes for autoclave. The liquid medium after cooled was inoculated with the transformant obtained in the above (2) and shake-cultured at 30° C. for 4 days. After the culturing was finished, the medium was centrifuged to harvest the supernatant and the GLD activity (U/mL) of each sample was measured according to the aforementioned GLD activity measuring method to confirm that each sample had GLD activity and that the recombinant fungi transformed by the BotGLD gene had a productivity of 13 U/mL per 1 mL of the culture solution and the recombinant fungi transformed by the BotGLD-Atsig modified gene had a productivity of 36 U/mL per 1 mL of the culture solution.

Example 9

Cloning of a GLD Gene Derived from Microorganisms of the Genus *Ovulinia*

(Preparation of a Vector Containing an Insert DNA)

(1) Culturing of Microorganism

A liquid medium consisting of 1% (W/V) of glucose (manufactured by Nacalai Tesque, Inc.), 2% (W/V) of defatted soybean (manufactured by Showa Sangyo Co., Ltd.), 0.5% (W/V) of a corn steep liquor (manufactured by San-ei Sucrochemical Co., Ltd.), 0.1% (W/V) of magnesium sulfate heptahydrate (manufactured by Nacalai Tesque, Inc.) and water was adjusted to pH 6.0. 150 mL of the liquid medium were added into a 500 mL of Sakaguchi flask and treated at 121° C. for 20 minutes for autoclave. The liquid medium after cooled was inoculated with *Ovulinia azaleae* NBRC6610 strains and shake-cultured at 15° C. for 90 hr and then, wet cells were harvested by using a bleached cloth.

(2) Isolation of a Total RNA 200 mg of the wet cells obtained in the above (1) was frozen at −80° C. and then, 100 μg of a total RNA was extracted with ISOGEN II (trademark, manufactured by NIPPON GENE CO., LTD.).

(3) Preparation of a cDNA Library

A cDNA library was prepared from the total RNA by reverse transcription using a reverse transcriptase and an oligo dT primer with an adapter sequence. As the reaction reagent, a "SMARTer RACE cDNA Amplification kit" (manufactured by TAKARA BIO INC.) was used and the reaction was run in a condition according to the protocol described in an instruction manual.

(4) Cloning of a GLD Gene

Using, as a template, the cDNA library obtained in the above (3), a primer pair represented by SEQ ID NOs: 17 and 18 described in Example 5(4) was used to perform PCR and as a result, a band corresponding to about 1,200 bp length was confirmed. The DNA fragment was purified to perform ligation with a T-vector PMD20 (trademark, manufactured by Takara Bio Inc.) by using a DNA Ligation Kit (trademark, manufactured by TAKARA BIO INC.).

An *E. coli* JM109 competent cell (manufactured by TAKARA BIO INC.) was transformed by a known method using the obtained plasmid. A plasmid was extracted from the obtained transformant and purified by using an illustra plasmid-Prep Mini Spin Kit to determine a gene sequence of the aforementioned amplified DNA contained in the plasmid (1,174 bp).

Moreover, the downstream region of the cDNA was PCR-amplified according to the 3' RACE method using a primer represented by the following SEQ ID NO: 29 designed based on the obtained internal sequence and the GLD sequence which had been already elucidated by the inventors of the present invention and the GLD gene was PCR-amplified using a primer pair represented by the following SEQ ID NOs: 30 and 31 to make analysis of the base sequence of the DNA fragment obtained according to the above method, and as a result, the full-length gene sequence of GLD represented by SEQ ID NO: 5 and having a total chain length of 1,773 bp was clarified. A full-length amino acid sequence for which this gene sequence encodes is represented by SEQ ID NO: 6.

```
SEQ ID NO: 29:
5'-CACATGGACATCCGACGCTAATACCCC-3'

SEQ ID NO: 30:
5'-ATGTATCGTTTACTCTCTACATTTGC-3'

SEQ ID NO: 31:
5'-CTACATGTCTTCCTTGATCAAATCTG-3'
```

(5) Transformation of Yeast and Confirmation of GLD Activity

A primer (SEQ ID NOs: 32 and 33) was so designed as to amplify a gene encoding for an amino acid sequence on and after the amino acid at position-17 in the amino acid sequence, that is, an amino acid sequence excluding a predicted signal sequence from the full-length amino acid sequence clarified in the above (4) and PCR was performed using, as a template, the cDNA prepared in the above (3) to obtain a modified gene. The PCR product was subjected to agarose electrophoresis, to confirm a band in the vicinity of about 1.8 kb, and therefore, cut by BglII and XbaI using a Wizard SV Gel and PCR Clean-Up System (trademark, manufactured by Promega K.K.) after gel-purified. Also, the pAFF4/DuGLD produced in the above (5) in Example 5 was treated with the same restriction enzyme, and the PCR product after treated by the restriction enzyme was ligated to a vector and introduced into *E. coli* JM109 strains to transform. Plasmid DNAs were prepared from five clones among the obtained transformants and treated with BglII and XbaI, to confirm DNA fragments each having an intended size in all clones. With regard to each of these five clones, a plasmid was prepared to determine the sequence of the insert, to confirm intended genes in each plasmid (pAFF4/OvGLD).

```
SEQ ID NO: 32:
5'-GAAGATCTAGCACCGACTCTACTTTAACTTATG-3'

SEQ ID NO: 33:
5'-GCTCTAGACTACATGTCTTCCTTGATCAAATCTG-3'
```

The prepared recombinant vector (pAFF4/OvGLD) was introduced into host yeast *Saccaromyces cerevisiae* BY4741. A Frozen-EZ Yeast Transformation II kit (trademark, manufactured by ZYMO RESEARCH CORP.) was used for the introduction. The obtained transformant was incubated in a 500 mL Sakaguchi flask in which 100 mL of a YPD medium containing 1.0% of a yeast extract (manufactured by BD (Becton, Dickinson and Company)), 2.0% of tripton (manufactured by BD (Becton, Dickinson and Company)) and 2.0% of glucose (manufactured by Wako Pure Chemical Industries, Ltd.) was added and shake-cultured at 30° C. at 120 rpm for 72 hr. After cultured, the medium was centrifuged to harvest the supernatant. The GLD activity of the supernatant was measured using a plate reader according to the above GLD activity measuring method, to confirm the GLD activity of the present invention.

Example 10

Cloning of a GLD Gene Derived from Microorganisms of the Genus *Ciborinia*

(1) Culturing of Microorganism

A liquid medium consisting of 1% (W/V) of glucose (manufactured by Nacalai Tesque, Inc.), 2% (W/V) of defatted soybean (manufactured by Showa Sangyo Co., Ltd.), 0.5% (W/V) of a corn steep liquor (manufactured by San-ei Sucrochemical Co., Ltd.), 0.1% (W/V) of magnesium sulfate heptahydrate (manufactured by Nacalai Tesque, Inc.) and water was adjusted to pH 6.0. 150 mL of the liquid medium were added into a 500 mL of Sakaguchi flask and treated at 121° C. for 20 minutes for autoclave. The liquid medium after cooled was inoculated with *Ciborinia camelliae* NBRC103663 strains and shake-cultured at 15° C. for 90 hr and then, wet cells were harvested by using a bleached cloth.

(2) Isolation of a Total RNA 200 mg of the wet cells obtained in the above (1) was frozen at −80° C. and then, 100 μg of a total RNA was extracted with ISOGEN II (trademark, manufactured by NIPPON GENE CO., LTD.).

(3) Preparation of a cDNA Library

A cDNA library was prepared from the total RNA by reverse transcription using a reverse transcriptase and an oligo dT primer with an adapter sequence. As the reaction reagent, a "SMARTer RACE cDNA Amplification kit" (manufactured by TAKARA BIO INC.) was used and the reaction was run in a condition according to the protocol described in an instruction manual.

(4) Cloning of a GLD Gene

A GLD gene was PCR-amplified using, as a template, the cDNA library obtained in the above (3) and also using a primer pair represented by SEQ ID NOs: 17 and 18 described in Example 5 (4), and as a result, a band corresponding to about 1,200 bp length was confirmed. The DNA fragment was purified to perform ligation with a T-vector PMD20 (trademark, manufactured by TAKARA BIO INC.) by using a DNA Ligation Kit (trademark, manufactured by TAKARA BIO INC.).

A *E. coli* JM109 competent cell (manufactured by TAKARA BIO INC.) was transformed by a known method using the obtained plasmid. A plasmid was extracted from the obtained transformed material and purified by using an illustra plasmid-Prep Mini Spin Kit to determine a gene sequence of the aforementioned amplified DNA contained in the plasmid. Moreover, the upstream region of the cDNA was amplified by PCR according to the 5' RACE method using a primer represented by the following SEQ ID NO: 43 designed based on the obtained internal sequence and the downstream region of the cDNA was amplified by PCR according to the 3' RACE method using a primer represented by the following SEQ ID NO: 44 to make analysis of the base sequence of the DNA fragment obtained according to the above method, and as a result, the full-length gene sequence of GLD derived from the *Ciborinia camelliae* NBRC103663 strains represented by the above SEQ ID NO: 7 and having a total chain length of 1,776 bp was clarified. A full-length amino acid sequence for which this gene sequence encodes is represented by the above SEQ ID NO: 8.

```
SEQ ID NO: 43:
5'-ACGGAAATGTTGTACTTCTCAAGGATAGCA-3'

SEQ ID NO: 44:
5'-CGTCGTTGATCTCCCAACCGTCGGAGAGAA-3'
```

(5) Construction of Plasmid pSENS/CiGLD and CiGLD-Atsig

PCR was performed using, as a template, the cDNA prepared in the above (3) and also using a primer pair represented by the following SEQ ID NOs: 45 and 46 designed from the sequence represented by SEQ ID NO: 7 to obtain a PCR product containing a full-length CiGLD gene. Moreover, PCR for obtaining a CiGLD-Atsig modified gene encoding a protein substituting a predicted signal sequence of CiGLD with a signal sequence of GLD derived from *Aspergillus terreus* was performed in three stages. As each of the reverse primers, a primer represented by SEQ ID NO: 46 was used. In the first stage, the above PCR product was used as a template to perform PCR using, as a forward primer, a primer (SEQ ID NO: 47) so designed as to amplify a gene encoding for an amino acid sequence on and after the amino acid at position-20 in the amino acid sequence, that is, an amino acid sequence excluding a predicted signal sequence of CiGLD. The PCR in the second stage was performed using as a template, the PCR product obtained in the first stage and also using, as a forward primer, a primer represented by SEQ ID NO: 37, and the PCR in the third stage was performed using, as a template, the PCR product obtained in the second stage and also using, as a forward primer, a primer represented by SEQ ID NO: 38, to obtain a PCR product including a DuGLD-Atsig modified gene.

SEQ ID NO: 45:
5'-(CCGCAGCTCGTCAAA)ATGCATCGCTTCCTTCCTGCC-3'

SEQ ID NO: 46:
5'-(GTTACGCTTCTAGA)<u>GCATGC</u>GTTCATTTACATATCTTCCTTGATC-3'

SEQ ID NO: 47:
5'-<u>GTGGCGGCACCTTTG</u>GTTGCCTTAACCTACGATTAT-3'

(Parenthesis: transcription enhancing factor, double parenthesis: pSENS vector sequence, underline portion: restriction enzyme site (SphI), underline portions of SEQ ID NO: 47: signal sequences)

Next, the above PCR product including a full-length CiGLD gene and PCR product including a CiGLD-Atsig modified gene were each used as a template to perform PCR by using a primer pair represented by SEQ ID NOs: 39 and 46, to add a restriction enzyme recognition site and a vector sequence at the N-terminal side.

Using an amylase type improved promoter derived from *Aspergillus oryzae* described in a known literature 1 ("Heterologous Gene Expression System of The Genus *Aspergillus*", MINETOKI Toshitaka, Biotechnology, and Agrochemistry, 38, 12, 831-838, 2000), two plasmid vectors which were gene-expressible were each prepared by binding two PCR products obtained above to the downstream of the promoter. These expressing plasmid vectors were respectively introduced into *E. coli* JM109 strains to transform and each obtained transformant was cultured to extract each plasmid from the collected bacterial body by using an Illustra plasmid-prep MINI Flow Kit (trademark, manufactured by GE Healthcare Japan). The sequence analysis of inserts in each plasmid was made and as a result, a CiGLD gene (SEQ ID NO: 7) or a CiGLD-Atsig modified gene (SEQ ID NO: 52) was confirmed.

(2) Acquisition of a Transformant

Recombinant fungi (*Aspergillus oryzae*) into which a CiGLD gene or CiGLD-Atsig modified gene was introduced were respectively produced using the plasmid extracted in the above (5) according to the method described in a known literature 2 and literature 3. The obtained recombinant strains were each refined in a Czapek-Dox solid medium. As the host, *Aspergillus oryzae* NS 4 strain was used.

(7) Confirmation of the Activity of CiGLD Derived from Recombinant Fungi and CiGLD-Atsig 15 mL of a liquid medium consisting of 2% (w/v) of a Pinedex (trademark, manufactured by Matsutani Chemical Industry Co., Ltd.), 1% (w/v) of tripton (manufactured by BD (Becton, Dickinson and Company)), 0.5% (w/v) of potassium dihydrogenphosphate (manufactured by Nacalai Tesque, Inc.), 0.05% (w/v) of magnesium sulfate heptahydrate (manufactured by Nacalai Tesque, Inc.) and water were added into a thick test tube (22 mm×200 mm) and treated at 121° C. for 20 minutes for autoclave. The liquid medium after cooled was inoculated with the transformant obtained in the above (6) and shake-cultured at 30° C. for 4 days. After the culturing was finished, the medium was centrifuged to harvest the supernatant and the GLD activity (U/mL) of each sample was measured according to the aforementioned GLD activity measuring method to confirm that each sample had GLD activity and that the recombinant fungi transformed by the CiGLD gene had a productivity of 90 U/mL per 1 mL of the culture solution and the recombinant fungi transformed by the CiGLD-Atsig modified gene had a productivity of 250 U/mL per 1 mL of the culture solution.

Example 11

N-terminal Analysis

When the N-terminal of the purified DuGLD obtained in Example 1 was analyzed, it was confirmed that the acid sequence at the N-terminal was LSLTYD. Namely, it was found that 19 amino acids MNHLLPAFALASLAVASPD were a signal sequence, these amino acids were deleted from the enzyme by the modification using signal peptidase after translated and the enzyme existed as a glucose dehydrogenase represented by SEQ ID NO: 8. Moreover, it was inferred that 19 amino acids form a signal sequence similarly to OvGLD, BotGLD and CiGLD from sequence homology and comparison with the *Aspergillus terreus* GLD sequence described in Patent Literature 1.

Example 12

Purification of GLD Derived from the Genus *Botrytis*: Glucose Dehydrogenase (E)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 $cm^2$ of *A. oryzae* NS4 strains into which a BotGLD-Atsig modified gene cultured in advance on a plate was introduced, and then, subjected to rotational shaking culture performed at 25° C. at 100 rpm for 3 days. This medium was used as a seed medium and 3.5 L of the above medium put into a 5 L jar fermentor and treated for autoclave was inoculated with 0.05 L of the seed culture, followed by culturing at 25° C., at 300 rpm and a rate of 1 v/v/m for 7 days. After the culturing was finished, the cultured solution was filtered with a filter cloth to harvest the filtrate. Then, the obtained filtrate was subjected to centrifugation (7,000×g, 30 minutes) to harvest the supernatant, which was then subjected to suction filtration using a membrane filter (manufactured by Advantech Co., Ltd., 10 μm) to harvest 2 L of the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 50% saturation to precipitate an unnecessary protein. The enzyme solution was allowed to stand at 4° C. overnight and then subjected to centrifugation (7,000×g, 30 minutes) to harvest the supernatant.

This supernatant was made to flow through a Butyl Toyopearl 650C (trademark, manufactured by TOSOH CORPORATION) column (ϕ 2.0 cm×14.0 cm) equilibrated in advance with a buffer solution A1 (20 mM potassium phosphate buffer solution, 50% saturated ammonium sulfate, pH 6.0). After the column was washed with the buffer solution A1, a protein was eluted with a linear gradient of a buffer solution B1 (20 mM potassium phosphate buffer solution, pH 6.0) in the buffer solution A1. Among the eluted protein, an active fraction was concentrated, then dialyzed against a buffer solution C1 (1 mM potassium phosphate buffer solution, pH 6.0), and made to flow through a DEAE Cellfine A-500m (trademark, manufactured by JNC Corporation) column equilibrated in advance with the buffer solution C1. After the column was washed with the buffer solution C1, a protein was eluted with a linear gradient of a buffer solution D1 (200 mM potassium phosphate buffer solution, pH 6.0) in the buffer solution C1. Among the eluted protein, an active fraction was concentrated and desalted to obtain a purified enzyme of GLD derived from the genus *Botrytis tulipae* substituted with water. Hereinafter the purified enzyme of GLD derived from the genus *Botrytis tulipae* is abbreviated as BotGLD.

Example 13

Purification of GLD Derived from the Genus *Ciborinia*: Glucose Dehydrogenase (F)

0.05 L of a preculture medium (D-glucose 1.0%, soybean powder 2.0%, corn steep liquor 0.5%, magnesium sulfate heptahydrate 0.1%, pH 7.0) were added into a 0.2 L conical flask with baffles and the mixture was treated at 121° C. for 20 minutes for autoclave. The medium was inoculated with about 0.5 $cm^2$ of *A. oryzae* NS4 strains into which a CiGLD-Atsig modified gene cultured in advance on a plate was introduced, and then, subjected to rotational shaking culture performed at 25° C. at 100 rpm for 3 days. This medium was used as a seed medium and 3.5 L of the above medium put into a 5 L jar fermentor and treated for autoclave was inoculated with 0.05 L of the seed culture, followed by culturing at 25° C., at 300 rpm and a rate of 1 v/v/m for 7 days. After the culturing was finished, the cultured solution was filtered with a filter cloth to harvest the filtrate. Then, the obtained filtrate was subjected to centrifugation (7,000×g, 30 minutes) to harvest the supernatant, which was then subjected to suction filtration using a membrane filter (manufactured by Advantech Co., Ltd., 10 μm) to harvest 2 L of the cultured supernatant.

The above cultured supernatant was concentrated using an ultrafiltration concentrating membrane (manufactured by Millipore Japan Co., Ltd., fractional molecular weight 8,000). Ammonium sulfate was gradually added to the concentrated enzyme solution to the extent of 50% saturation to precipitate an unnecessary protein. The enzyme solution was allowed to stand at 4° C. overnight and then subjected to centrifugation (7,000×g, 30 minutes) to harvest the supernatant.

This supernatant was made to flow through a Butyl Toyopearl 650C (trademark, manufactured by TOSOH CORPORATION) column (ϕ 2.0 cm×14.0 cm) equilibrated in advance with a buffer solution A1 (20 mM potassium phosphate buffer solution, 50% saturated ammonium sulfate, pH 6.0). After the column was washed with the buffer solution A1, a protein was eluted with a linear gradient of a buffer solution B1 (20 mM potassium phosphate buffer solution, pH 6.0) in the buffer solution A1. Among the eluted protein, an active fraction was concentrated, then dialyzed against a buffer solution C1 (1 mM potassium phosphate buffer solution, pH 6.0), and made to flow through a DEAE Cellfine A-500m (trademark, manufactured by JNC Corporation) column equilibrated in advance with the buffer solution C1. After the column was washed with the buffer solution C1, a protein was eluted with a linear gradient of a buffer solution D1 (200 mM potassium phosphate buffer solution, pH 6.0) in the buffer solution C1. Among the eluted protein, an active fraction was concentrated and desalted to obtain a purified enzyme of GLD derived from the genus *Ciborinia* substituted with water. Hereinafter the purified enzyme of GLD derived from the genus *Ciborinia* is abbreviated as CiGLD.

Example 14

Test for the Property of GLD of the Present Invention

Various properties of each purified GLD obtained in Examples were examined. (A) to (F) represent the following enzymes: (A): DuGLD, (B): OvGLD, (C): ScGLD, (D): BoGLD, (E): BotGLD and (F): CiGLD.

(a) Coenzyme

The absorption spectrum of each of the purified GLDs (A) to (F) at 300 to 600 nm was measured using a microplate reader (trademark: SPECTRA MAX PLUS 384, manufactured by Molecular Device Corporation. The results of the measurement are shown in FIG. 1. Each purified GLD was found to have its absorption maximums at a wavelength around 360 to 380 nm and a wavelength around 450 to 460 nm. Because these absorption maximums are specific to flavin, it was clarified that the coenzyme of each GLD of the present invention is a flavin adenine dinucleotide.

(b) Km Value to D-glucose

With regard to each of the purified GLDs (A) to (F), the concentration of D-glucose which was a substrate was varied to measure GLD activity in the aforementioned activity measuring method. A Michaelis constant (Km) of each GLD was calculated from a Hanes-Woolf plot and shown collectively in Table 1. In this case, because the Km value is varied corresponding to measuring method and calculated plots, the Km value of each GLD is considered to be as follows: DuGLD: about 100 to 200 mM, OvGLD: about 10 to 40 mM, ScGLD: about 10 to 30 mM, BoGlD: about 20 to 50 mM, BotGLD: about 20 to 50 mM and CiGLD: about 1.0 to 20 mM.

TABLE 1

Km value of GLD of the present invention

| | Km value (mM) |
|---|---|
| DuGLD | 140 |
| OvGLD | 22.8 |
| ScGLD | 16.7 |
| BoGLD | 35.0 |
| BotGLD | 36.2 |
| CiGLD | 5.44 |

(c) Measurement of Glucose Oxidase (GOD) Activity

The GOD activity of each of the purified GLDs (A) to (F) was examined and as a result, each GLD was found to have no GOD activity. Accordingly, GLD of the present invention did not substantially utilize oxygen as en electron acceptor and therefore, it was clarified that a biosensor resistant to the influence of dissolved oxygen could be manufactured when GLD of the present invention was used for a blood sugar level measuring biosensor.

The GOD activity was measured by the following method. 1.00 mL of 100 mM potassium phosphate buffer solution (pH 7.0), 0.10 mL of 25 mM 4-amino antipyrine, 0.10 mL of 420 mM phenol, 0.10 mL of peroxidase (100 units/mL), 0.65 mL of ultrapure water and 1.00 mL of D-glucose were blended and kept at 37° C. for 5 min. 0.05 mL of an enzyme sample was added to the mixture to start a reaction. An increase in the amount (ΔA500)/minute of absorbance at 500 nm along with the progress of enzymatic reaction was measured from the start of reaction to calculate GOD activity according to the following equation 2. In the measurement of the GOD activity, the amount of enzyme generating 1 mol of hydrogen peroxide at 37° C. and pH 7.0 for one minute was defined as 1 U. 3.0 in the equation represents the liquid measure (mL) of a reaction reagent+an enzyme solution, 10.66 represents mol absorption coefficient (mM−1 cm−1) in this measuring condition, 0.5 represents the ratio of the formation of a quinone type dye to the formation of 1 mol of hydrogen peroxide, 1.0 represents the optical path (cm) of a cell, 0.05 represents the amount (mL) of an enzyme solution, ΔA500 blank represents an increase in the amount of light absorbance per minute at 500 nm when the solution used to dilute the enzyme is added in place of the enzyme solution to start a reaction, and df represents a dilution ratio.

$$\text{GOD activity (U/mL)} = \frac{(\Delta A500 - \Delta A500\ \text{blank}) \times 3.0 \times df}{(10.66 \times 0.5 \times 1.0 \times 0.05)} \quad \text{[Math. formulation 2]}$$

(d) Heat Stability

Figure 2:
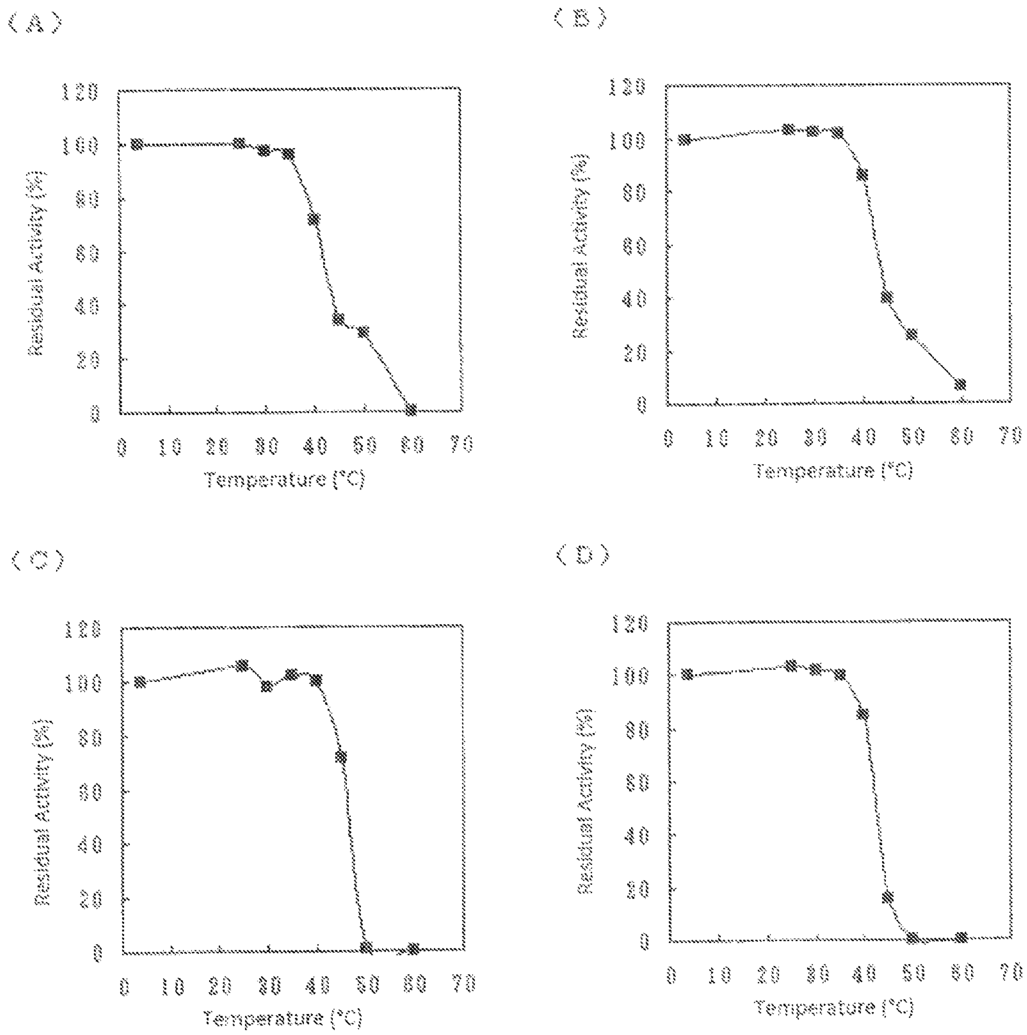
FIG. 2 shows the heat stability of glucose dehydrogenases (A) to (D) according to the present invention.

Each purified GLDs (A) to (D) was adjusted to 6 U/mL and treated at each temperature between 4 to 60° C. for 15 minutes in a 100 mM potassium phosphate buffer solution (pH 6.0) to measure enzymatic activity by the above method for measuring enzymatic activity. The residual ratio of enzymatic activity was calculated and is shown as heat stability in FIG. 2. When the activity of each purified GLD measured by the above method for measuring enzymatic activity after the purified GLD was treated at 4° C. for 15 minutes in a 100 mM potassium phosphate buffer solution (pH 6.0) was defined as 100%, the residual activity measured by the above method for measuring enzymatic activity after the GLD was treated at each temperature for 15 minutes was as follows: DuGLD: 90% or more at 35° C., 70% or more at 40° C. and 30% or more at 45° C., OvGLD: 90% or more at 35° C., 80% or more at 40° C. and 30% or more at 45° C., ScGLD: 90% or more at 40° C. and 70% or more at 45° C., and BoGLD: 90% or more at 35° C., 80% or more at 40° C. and 15% or more at 45° C. From the above, the GLD of the present invention was found to have a residual activity of 70% or more after heat treatment at 40° C. for 15 minutes and a residual activity of 90% or more after heat treatment at 35° C. for 15 minutes.

(e) Stable pH

Figure 3:
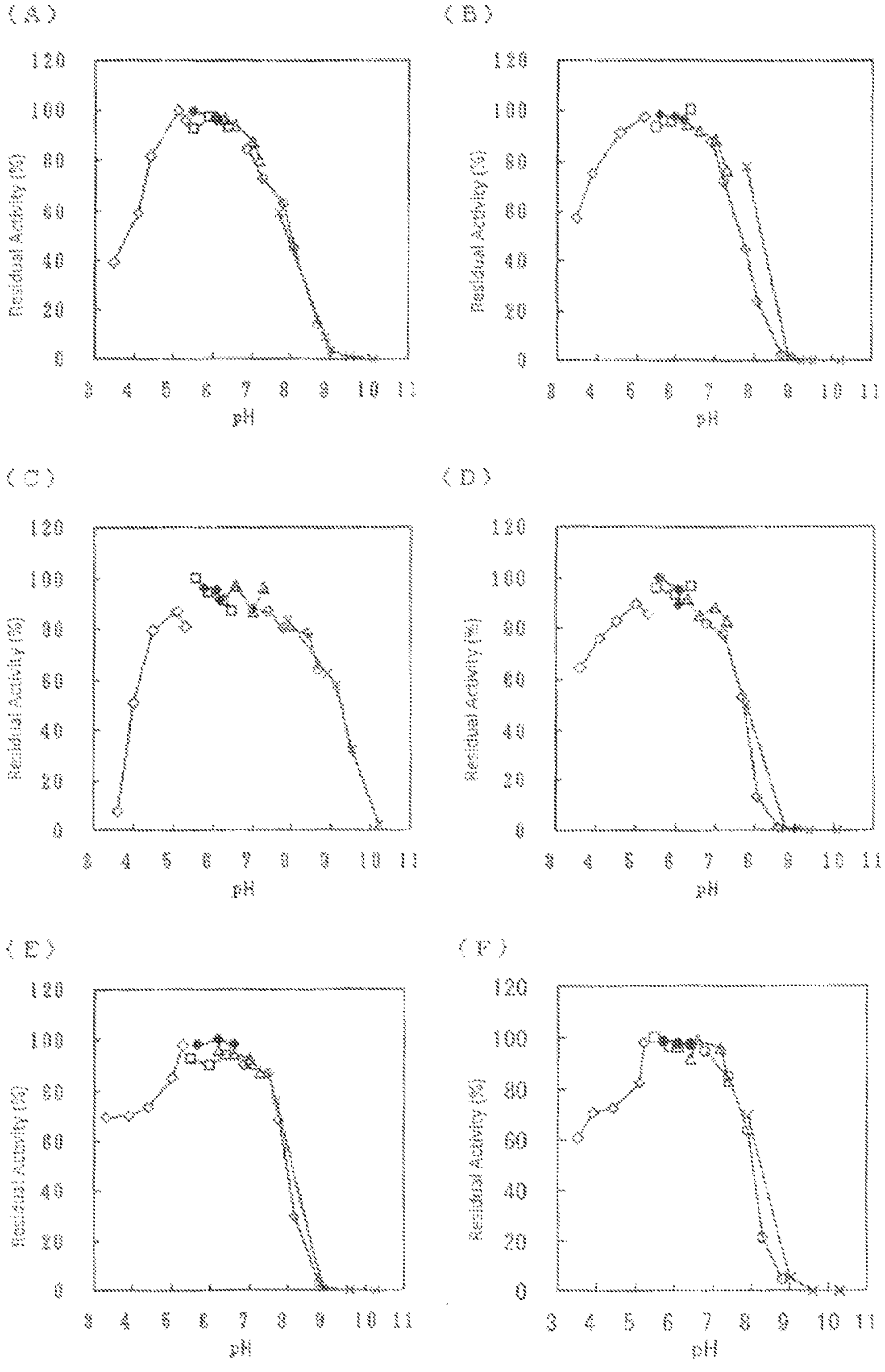
FIG. 3 shows stable pH ranges of glucose dehydrogenases (A) to (F) according to the present invention.

Each purified GLDs (A) to (F) was adjusted to 6 U/mL and the following buffer solutions were respectively added to the purified GLD such that the final concentration of each buffer solution was 100 mM: a sodium acetate buffer solution (pH 3.5 to 5.5, plotted as a diagonal square mark in the graph), sodium citrate buffer solution (pH 5.0 to 6.0, plotted as a square mark in the graph), sodium phosphate buffer solution (pH 5.0 to 6.0, plotted as a black dot mark in the graph), potassium phosphate buffer solution (pH 6.0 to 7.5, plotted as a triangle mark in the graph), Tris-HCl buffer solution (pH 7.0 to 9.0, plotted as a white circle mark) and glycine-NaOH buffer solution (pH 8.0 to 11.0, plotted as x mark). Then, the solution was treated at 25° C. for 16 hr and then, the enzymatic activity was measured according to the aforementioned method for measuring enzymatic activity. The residual rate of enzymatic activity was calculated and is shown as the stable pH in FIG. 3. As a result, the residual enzymatic activity of each GLD was as follows when the activity of the enzyme treated by a buffer solution at a pH at which the enzyme was most stable after each purified GLD was treated at 25° C. for 16 hr in 100 mM buffer solutions having various pHs was defined as 100%: DuGLD: 80% or more at pH 4.4 to 7.2, 70% or more at pH 4.4 to 7.3 and 40% or more at pH 4.1 to 8.1, OvGLD: 80% or more at pH 4.5 to 7.0, 70% or more at pH 3.9 to 7.8 and 40% or more at pH 3.5 to 7.8, ScGLD: 80% or more at pH 5.0 to 7.9, 70% or more at pH 4.5 to 8.4 and 40% or more at pH 4.0 to 9.1, BoGLD: 80% or more at pH 4.5 to 7.3, 70% or more at pH 4.1 to 7.3 and 40% or more at pH 3.6 to 7.8, BotGLD: 80% or more at pH 5.0 to 7.5, 70% or more at 3.9 to 7.7 and 40% or more at pH 3.3 to 7.8, and CiGLD: 80% or more at pH 5.1 to 7.4, 70% or more at pH 3.9 to 7.9 and 40% or more at pH 3.5 to 7.9. From the above results, it was found that the stable pH range of the GLD of the present invention was as follows: the residual activity: 80% in a pH range from 5.0 to 7.0, 70% or more in a pH range from 4.5 to 7.0 and 40% or more in a pH range from 4.0 to 7.5. It is to be understood that even if the buffer solution has the same pH, the residual activity differs depending on the type of buffer solution.

(f) Molecular Weight

DuGLD and OvGLD were each dissolved in a 50 mM potassium phosphate buffer solution (pH 6.0) including 0.2 M NaCl to analyze by using the same buffer solution as a mobile phase in TSK gel-G3000SW (trademark, manufactured by TOSOH CORPORATION, ϕ 2.15 cm×60.0 cm). The sample was measured by analysis using the gel filtration method and as a result, the molecular weight of DuGLD was 150 to 230 kDa and the molecular weight of OvGLD was 260 to 440 kDa by using a molecular weight marker (Gel Filtration standard, manufactured by Bio-Rad) as an index.

Figure 4:
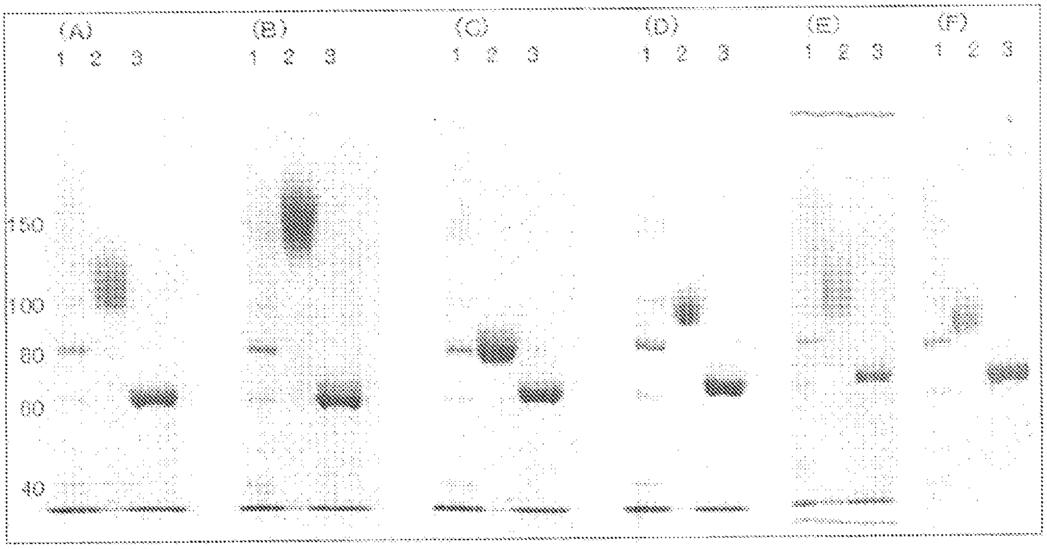
FIG. 4 shows the results of SDS-polyacrylamide gel electrophoresis of glucose dehydrogenases (A) to (F) according to the present invention.

The molecular weight of each of the purified GLDs (A) to (F) before and after a sugar chain was cleaved was found by the following method. 5 μL of each enzyme solution (each adjusted to 1.0 mg/mL), 1% of SDS and 5 μL of a 0.4 M sodium phosphate buffer solution (pH 6.0) including 2% of β-mercaptoethanol were mixed and the mixture was heat-treated at 100° C. for 3 minutes. In the sugar chain cutting treatment, 10 μL (50 mU) of endoglycosidase H (manufactured by Roche) was added to the sample after the heat-treatment to react at 37° C. for 18 hr. The samples before and after the sugar chain cutting treatment were subjected to SDS-polyacrylamide electrophoresis using 7.5% of e-PAGEL (manufactured by ATTO Corporation) and dyed with Coomassie Brilliant Blue (CBB) after the electrophoresis was finished. The results are shown in FIG. 4. The mobility of each GLD was compared with that of a molecular weight marker to find the molecular weight thereof. The electrophoresis sample is as follows.

FIG. 4(A)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: before cleaving DuGLD sugar chain

Lane 3: after cleaving DuGLD sugar chain

FIG. 4(B)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: before cleaving OvGLD sugar chain

Lane 3: after cleaving OvGLD sugar chain

FIG. 4(C)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: before cleaving ScGLD sugar chain

Lane 3: after cleaving ScGLD sugar chain

FIG. 4(D)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: before cleaving BoGLD sugar chain

Lane 3: after cleaving BoGLD sugar chain

FIG. 4(E)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: Before cleaving BotGLD sugar chain

Lane 3: After cleaving BotGLD sugar chain

FIG. 5(F)

Lane 1: molecular weight marker (manufactured by BioDynamics Laboratory Corporation, DynaMarker Protein Recombinant (10-150 kDa), 150 kDa, 100 kDa, 80 kDa, 60 kDa and 40 kDa from above)

Lane 2: before cleaving CiGLD sugar chain

Lane 3: after cleaving CiGLD sugar chain

From FIG. 4, the molecular weight of each GLD was as follows: DuGLD: 90 to 130 kDa, OvGLD: 130 to 200 kDa, ScGLD: 70 to 90 kDa, BoGLD: 90 to 100 kDa, BotGLD: 100 to 120 kDa and CiGLD: 900 to 100 kDa, and the molecular weight of each GLD after a sugar chain was cleaved was 60 to 70 kDa.

(g) Substrate Specificity

With regard to each of the purified GLDs (A) to (F), D-glucose in the above method for measuring enzymatic activity was replaced with other substrate to measure enzymatic activity to each substrate. As these substrates, maltose, D-galactose, D-fructose, sorbitol, lactose, sucrose, D-xylose, D-mannose and trehalose were used. When the activity to D-glucose was defined as 100%, the relative activity to each substrate was found. These relative activities are described collectively as the substrate specificity in Table 2.

TABLE 2

| | Relative activity (%) | | | | | |
|---|---|---|---|---|---|---|
| | DuGLD | OvGLD | ScGLD | BoGLD | BotGLD | CiGLD |
| D-glucose | 100 | 100 | 100 | 100 | 100 | 100 |
| Maltose | 0.54 | 3.0 | 3.9 | 1.1 | 1.5 | 6.4 |
| D-galactose | 0.28 | 1.3 | 1.5 | 0.39 | 0.76 | 10 |
| D-fructose | 0.1> | 0.12 | 0.1> | 0.1> | 0.1> | 0.49 |
| Sorbitol | 0.1> | 0.1> | 0.1> | 0.1> | 0.1> | 0.38 |
| Lactose | 0.1> | 0.1> | 0.1> | 0.1> | 0.1> | 0.21 |
| Sucrose | 0.1> | 0.1> | 0.1> | 0.1> | 0.1> | 0.40 |
| D-xylose | 10 | 8.2 | 22 | 10 | 20 | 25 |
| D-mannose | 1.7 | 5.7 | 11 | 3.9 | 8.2 | 23 |
| Trehalose | 1.0 | 4.6 | 7.8 | 2.7 | 10 | 20 |

The GLD of the present invention had a reactivity of 20% or less on maltose, D-galactose, D-fructose, sorbitol, lactose and sucrose, and further had a reactivity of 1% or less on D-fructose, sorbitol or sucrose in the case of defining the activity ton-glucose as 100% when the reactivity was measured at a substrate concentration of 333 mM.

(h) Optimum Temperature

Figure 5:
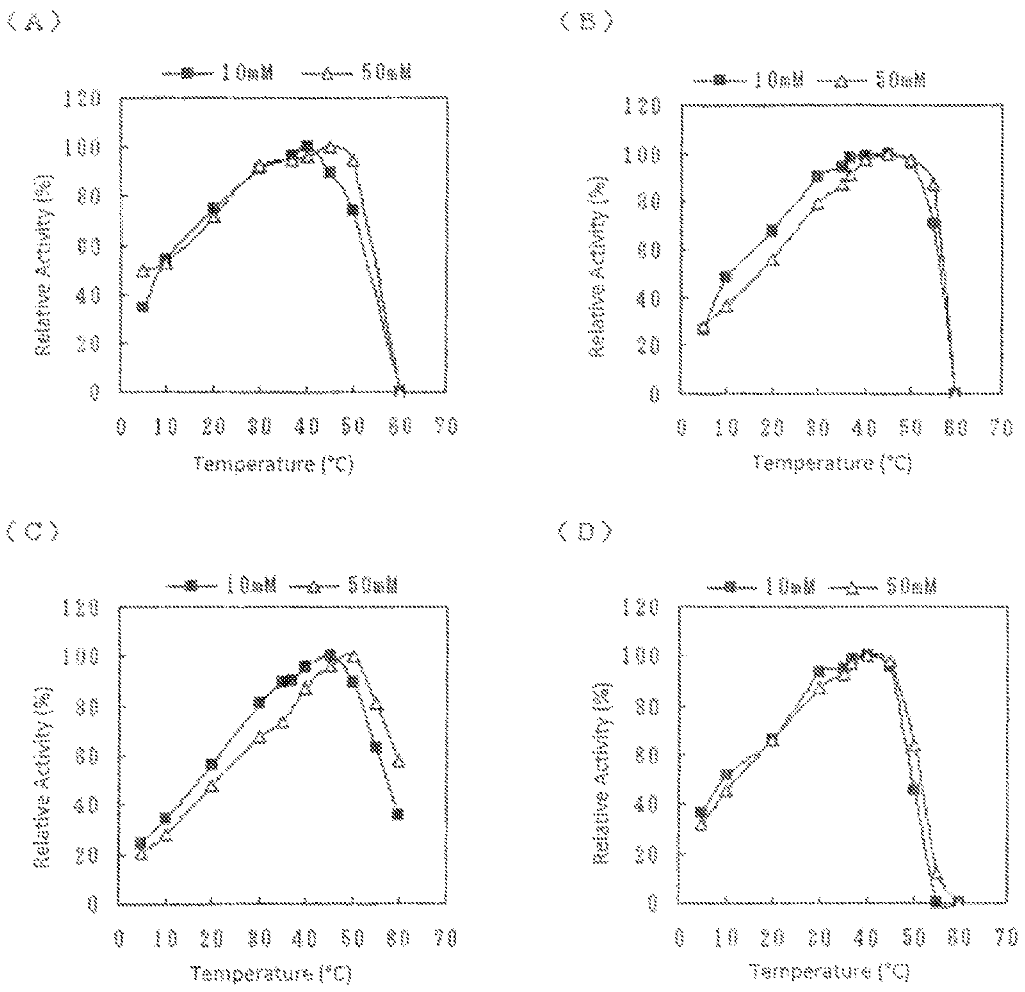
FIG. 5 shows the optimum temperatures of glucose dehydrogenases (A) to (D) according to the present invention.

With regard to each of the purified GLDs (A) to (D), its enzymatic activity was measured in the same manner as in the above method for measuring enzymatic activity except that the temperature was set to each temperature between 5 and 60° C. and the final concentration of the substrate was set to 10 mM and 50 mM. 1.00 mL of a 100 mM potassium phosphate buffer solution (pH 6.0), 0.03 mL of a 1 M D-glucose solution, 1.58 mL of ultrapure water, 0.14 mL of 3 mM DCIP and 0.20 mL of 3 mM 1-m-PMS were mixed when the final concentration of the substrate was 10 mM, and 1.00 mL of a 100 mM potassium phosphate buffer solution (pH 6.0), 0.15 mL of a 1 M D-glucose solution, 1.46 mL of ultrapure water, 0.14 mL of 3 mM DCIP and 0.20 mL of 3 mM 1-m-PMS were mixed when the final concentration of the substrate was 50 mM. These resulting solutions were each kept warm at each temperature instead of keeping at 37° C. for 10 minutes irrespective of each final concentration of the substrate. 0.05 mL of an enzyme sample was added to each solution to start a reaction at each temperature. The reduction in absorbance per minute at 600 nm along with the progress of an enzyme reaction was measured for five minutes from the start of the reaction to calculate GLD activity from the linear line part according to the aforementioned equation 1. The relative activity at each temperature was calculated when the activity at the temperature at which each purified GLD showed a maximum activity was defined as 100%. This temperature was defined as an optimum temperature as shown in FIG. 5. As a result, in the case where the activity at which each purified GLD showed a maximum activity was defined as 100%, DuGLD had a relative activity of 80% or more at 30 to 45° C., OvGLD had a relative activity of 80% or more at 30 to 50° C., ScGLD had a relative activity of 80% or more at 30 to 50° C., and BoGLD had a relative activity of 80% or more at 30 to 45° C. when the substrate concentration was 10 mM, DuGLD had a relative activity of 80% or more at 30 to 50° C., OvGLD had a relative activity of 80% or more at 35 to 55° C., ScGLD had a relative activity of 80% or more at 40 to 55° C., and BoGLD had a relative activity of 80% or more at 30 to 45° C. when the substrate concentration was 50 mM, and DuGLD had a relative activity of 80% or more at 30 to 45° C., OvGLD had a relative activity of 80% or more at 35 to 50° C., ScGLD had a relative activity of 80% or more at 40 to 50° C., and BoGLD had a relative activity of 80% or more at 30 to 45° C. irrespective of substrate concentration. From the above, in the case where the activity at which each purified GLD showed a maximum activity was defined as 100%, the GLD of the present invention had a relative activity of 80% or more at 30 to 45° C. when the substrate concentration was 10 mM, a relative activity of 80% or more at 40 to 45° C. when the substrate concentration was 50 mM, and a relative activity of 80% or more at 40 to 45° C. irrespective of final concentration.

(i) Optimum pH

Figure 6:
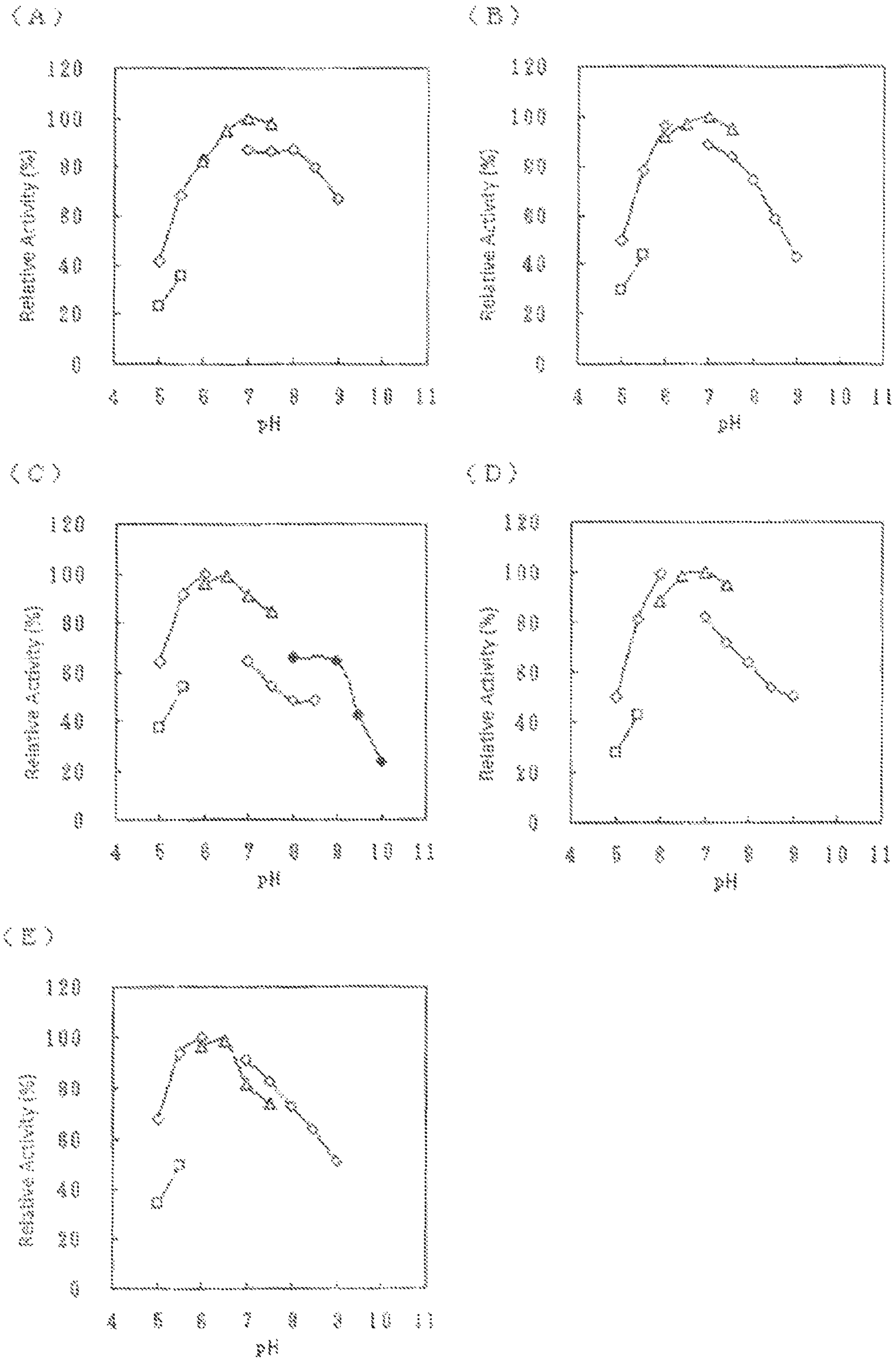
FIG. 6 shows the optimum pH of glucose dehydrogenases (A) to (E) according to the present invention.

With regard to each of the purified GLDs (A) to (E), the potassium phosphate buffer solution in the above method for measuring enzymatic activity was replaced with each substrate to measure enzymatic activity at each pH. As each buffer solution, a sodium acetate buffer solution (pH 5.0 to 5.5, plotted by a square mark in the drawing), a sodium citrate buffer solution (pH 5.0 to 6.0, plotted by a diagonal square mark in the drawing), a potassium phosphate buffer solution (pH 6.0 to 7.5, plotted by a triangle mark in the drawing), a tris hydrochloric acid buffer solution (pH 7.0 to 9.0, plotted by a white circular mark in the drawing) and a glycine sodium hydroxide buffer solution (pH 8.0 to 10.0, plotted by a black solid mark in the drawing) were used. The relative activity at each pH was calculated when the activity at the temperature at which each purified GLD showed a maximum activity was defined as 100%. This pH was defined as an optimum pH as shown in FIG. 6. As a result, in the case where the pH of the buffer solution at which each purified GLD showed a maximum activity was defined as 100%, DuGLD had a relative activity of 80% or more at pH 6.0 to 8.0 and a relative activity of 40% or more at pH 5.0 to 9.0, OvGLD had a relative activity of 80% or more at pH 6.0 to 7.5 and a relative activity of 40% or more at pH 5.0 to 9.0, ScGLD had a relative activity of 80% or more at pH 5.5 to 7.5 and a relative activity of 40% or more at pH 5.0 to 9.0, BoGLD had a relative activity of 80% or more at pH 5.5 to 7.5 and a relative activity of 40% or more at pH 5.0 to 9.0, and BotGLD had a relative activity of 80% or more at pH 5.5 to 7.5 and a relative activity of 40% or more at pH 5.0 to 9.0. From the above, in the case where the pH of the buffer solution at which each purified GLD showed a maximum activity was defined as 100%, the GLD of the present invention had a relative activity of 80% or more at pH 6.0 to 7.5 and a relative activity of 40% or more at pH 5.0 to 9.0.

(j) Temperature Characteristics

With regard to each of the purified GLDs (A) to (D), its enzymatic activity was measured in the same manner as in the above method for measuring enzymatic activity except that the temperature was set to each temperature between 10 and 50° C. and the final concentration of the substrate was set to 10 mM and 50 mM. The relative activity at each temperature was calculated when the activities at 30 and 45° C. were each defined as 100%. The results are collectively described in Table 3. In this case, each sample was measured twice in the same condition. An average of the measured relative activities is collectively described in Table 3. As a result, in the case where the activity at 30° C. was defined as 100%, the range of the activity at 10 to 50° C. was as follows: DuGLD: 60.6 to 108%, OvGLD: 54.4 to 107%, ScGLD: 43.2 to 119% and BoGLD: 55.0 to 106% when the substrate concentration was 10 mM, and DuGLD: 56.0 to 111%, OvGLD: 43.7 to 123%, ScGLD: 41.6 to 141% and BoGLD: 49.5 to 112% when the substrate concentration was 50 mM. In the case where the activity at 30° C. was defined as 100%, the range of the activity at 10 to 45° C. was as follows: DuGLD: 60.6 to 108%, OvGLD: 54.4 to 107%, ScGLD: 43.2 to 119% and BoGLD: 55.0 to 106% when the substrate concentration was 10 mM, and DuGLD: 56.0 to 111%, OvGLD: 43.7 to 123%, ScGLD: 41.6 to 137% and BoGLD: 49.5 to 112% when the substrate concentration was 50 mM. In the case where the activity at 45° C. was defined as 100%, the range of the activity at 10 to 45° C. was as follows: DuGLD: 60.1 to 107%, OvGLD: 51.9 to 102%, ScGLD: 36.4 to 100% and BoGLD: 58.8 to 113% when the substrate concentration was 10 mM, and DuGLD: 50.5 to 100%, OvGLD: 35.4 to 100%, ScGLD: 30.5 to 100% and BoGLD: 48.6 to 110% when the substrate concentration was 50 mM. It was found that in the case where the activity at 30° C. was defined as 100%, the GLD of the present invention had a range of the activity of 20 to 150% at 10 to 50° C. Accordingly, the GLD of the present invention shows reduced fluctuation of activity in a wide temperature range.

TABLE 3

(1) 100% at 30° C.

| Temperature | Relative activity (%) | | | | | | | |
|---|---|---|---|---|---|---|---|---|
| | DuGLD | | OvGLD | | ScGLD | | BoGLD | |
| (° C.) | 10 mM | 50 mM | 10 mM | 50 mM | 10 mM | 50 mM | 10 mM | 50 mM |
| 10 | 60.6% | 56.0% | 54.4% | 43.7% | 43.2% | 41.6% | 55.0% | 49.5% |
| 20 | 81.5% | 77.9% | 77.6% | 72.2% | 71.5% | 63.6% | 74.9% | 73.6% |
| 30 | 100% | 100% | 100% | 100% | 100% | 100% | 100% | 100% |
| 40 | 108% | 109% | 107% | 121% | 116% | 127% | 106% | 112% |

TABLE 3-continued

| | | | | | | | | |
|---|---|---|---|---|---|---|---|---|
| 45 | 101% | 111% | 105% | 123% | 119% | 137% | 93.5% | 102% |
| 50 | 87.5% | 105% | 97.8% | 118% | 106% | 141% | 43.6 | 62.0% |

(2) 100% at 45° C.

| Temperature | Relative activity | | | | | | | |
|---|---|---|---|---|---|---|---|---|
| | DuGLD | | OvGLD | | ScGLD | | BoGLD | |
| (° C.) | 10 mM | 50 mM | 10 mM | 50 mM | 10 mM | 50 mM | 10 mM | 50 mM |
| 10 | 60.1% | 50.5% | 51.9% | 35.4% | 36.4% | 30.5% | 58.8% | 48.6% |
| 20 | 80.7% | 70.3% | 74.0% | 58.5% | 60.2% | 46.6% | 80.1% | 72.3% |
| 30 | 99.1% | 90.2% | 95.3% | 81.0% | 84.3% | 73.3% | 107% | 98.3% |
| 40 | 107% | 98.6% | 102% | 97.6% | 97.9% | 93.1% | 113% | 110% |
| 45 | 100% | 100% | 100% | 100% | 100% | 100% | 100% | 100% |
| 50 | 86.7% | 94.4% | 93.2% | 95.7% | 89.7% | 103% | 46.6% | 61.0% |

(k) Inhibitive Effect of 1,10-Phenanthroline

The enzymatic activity of each of the purified GLDs (A) to (F) was measured when 1,10-phenanethroline dissolved in methanol was added such that its final concentration was 2 mM, 5 mM or 10 mM in the above method for measuring enzymatic activity. The inhibitive effect obtained when only methanol was added was defined as 0% to find the inhibitive effect of 1,10-phenanthroline at each concentration. The obtained results are shown collectively as the inhibitive effect of 1,10-phenanthroline in Table 4.

TABLE 4

| 1,10-phenanthroline Final concentration | Inhibitive effect (%) | | | | | |
|---|---|---|---|---|---|---|
| (mM) | DuGLD | OvGLD | ScGLD | BoGLD | BotGLD | CiGLD |
| 0 | 0 | 0 | 0 | 0 | 0 | 0 |
| 2 | 20.4 | 34.1 | 5.28 | 10.4 | 33.5 | 6.34 |
| 5 | 30.1 | 51.7 | 18.4 | 15.9 | 38.6 | 14.7 |
| 10 | 42.3 | 65.1 | 32.3 | 28.5 | 75.4 | 32.7 |

The inhibitive effect of 1,10-phenanthroline against the GLD of the present invention when the concentration of 1,10-phenanthroline was 2 mM was as follows: DuGLD, OvGLD and BotGLD: 20 to 34%, and ScGLD, BoGLD and CiGLD: about 5 to 10%.

Example 15

Figure 7:
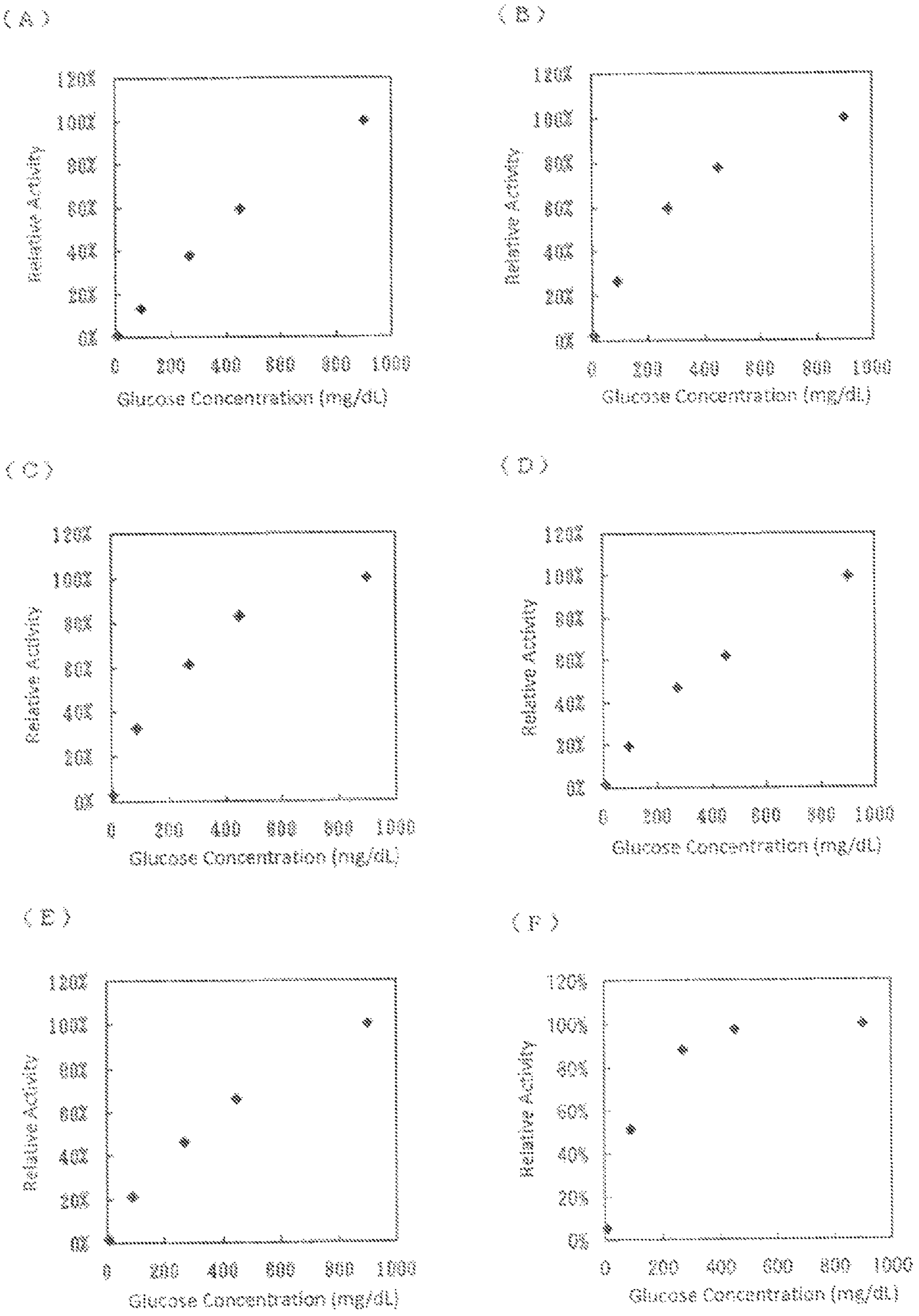
FIG. 7 shows results of measurement of the amount of glucose by using glucosedehydrogenases (A) to (F) according to the present invention.

Quantitative Determination of Glucose Concentration by the GLD of the Present Invention Using the GLDs (A) to (F) of the present invention, the concentration of D-glucose in the above activity measuring method was varied in a range from 0.3 mM (5.5 mg/dL) to 50 mM (900 mg/dL) to measure the variation of light absorbance. The results are shown in FIG. 7. It was shown to be possible that D-glucose was quantitatively measured by using the GLD of the present invention.

Example 16

The amino acid sequences or base sequences of each GLD of the present invention were compared among them according to GeneDoc (2.7.00) to find each identity (%). The results are described collectively in Table 5.

TABLE 5

| Amino acid sequence | | *D. tuberosa* 570AA | *B. tulipae* 590AA | *B. tulipae* 571AA | *O. azaleae* 590AA | *O. azaleae* 571AA | *C. camelliae* 591AA | *C. camelliae* 572AA |
|---|---|---|---|---|---|---|---|---|
| *D. tuberosa* | 589AA | 96% | 84% | 81% | 83% | 81% | 71% | 69% |
| *D. tuberosa* | 570AA | | 81% | 84% | 81% | 84% | 69% | 71% |
| *B. tulipae* | 590AA | | | 96% | 99% | 96% | 70% | 68% |
| *B. tulipae* | 571AA | | | | 96% | 99% | 68% | 70% |
| *O. azaleae* | 590AA | | | | | 96% | 70% | 68% |
| *O. azaleae* | 571AA | | | | | | 68% | 70% |
| *C. camelliae* | 591AA | | | | | | | 96% |

| Amino acid sequence | | *D. tuberosa* 1713 bp | *B. tulipae* 1773 bp | *B. tulipae* 1716 bp | *O. azaleae* 1773 bp | *O. azaleae* 1716 bp | *C. camelliae* 1776 bp | *C. camelliae* 1719 bp |
|---|---|---|---|---|---|---|---|---|
| *D. tuberosa* | 1770 bp | 96% | 81% | 78% | 80% | 78% | 73% | 71% |
| *D. tuberosa* | 1713 bp | | 78% | 81% | 78% | 80% | 71% | 73% |
| *B. tulipae* | 1773 bp | | | 96% | 99% | 96% | 70% | 68% |
| *B. tulipae* | 1716 bp | | | | 96% | 99% | 68% | 70% |
| *O. azaleae* | 1773 bp | | | | | 96% | 70% | 68% |
| *O. azaleae* | 1716 bp | | | | | | 68% | 70% |
| *C. camelliae* | 1776 bp | | | | | | | 96% |

It was confirmed, from Table 5, that a protein having an amino acid sequence with an identity of at least 60% and exhibiting glucose dehydrogenase activity, as well as a polynucleotide having a base sequence with an identity of at least 60% and encoding a glucose dehydrogenase can be obtained.

The invention claimed is:

1. A biosensor for measuring glucose concentration, comprising:

(i) a reaction layer comprising an electron acceptor and a recombinant flavin-binding glucose dehydrogenase exhibiting glucose dehydrogenase activity and consisting of an amino acid sequence of the following (a), (b) or (c):

(a) an amino acid sequence represented by SEQ ID NO: 2, 4, 6, 8, 10, 12, 14 or 16;

(b) an amino acid sequence wherein one to 20 amino acids are substituted, deleted or added in an amino acid sequence represented by SEQ ID NO: 2, 4, 6, 8, 10, 12, 14 or 16, or (c) an amino acid sequence having at least 95% identity with that represented by SEQ ID NO: 2, 4, 6, 8, 10, 12, 14 or 16; and (ii) an electrode system disposed on an insulating substrate.

2. The biosensor of claim 1, wherein the recombinant flavin-binding glucose dehydrogenase consists of an amino acid sequence represented by SEQ ID NO: 2, 4, 6, 8, 10, 12, 14 or 16.

3. The biosensor of claim 1, wherein the recombinant flavin-binding glucose dehydrogenase consists of an amino acid sequence wherein one to 20 amino acids are substituted, deleted or added in an amino acid sequence represented by SEQ ID NO: 2, 4, 6, 8, 10, 12, 14 or 16.

4. The biosensor of claim 1, wherein the recombinant flavin-binding glucose dehydrogenase consists of an amino acid sequence having at least 95% identity with that represented by SEQ ID NO: 2, 4, 6, 8, 10, 12, 14 or 16.

* * * * *

SEQUENCE LISTING

```
<160> NUMBER OF SEQ ID NOS: 53

<210> SEQ ID NO 1
<211> LENGTH: 1770
<212> TYPE: DNA
<213> ORGANISM: Dumontinia tuberosa
<220> FEATURE:
<221> NAME/KEY: CDS
<222> LOCATION: (1)..(1770)
<220> FEATURE:
<221> NAME/KEY: sig_peptide
<222> LOCATION: (1)..(57)

<400> SEQUENCE: 1

atg aat cat tta ctt cct gct ttt gct tta gcc tcc ttg gcc gtt gcc       48
Met Asn His Leu Leu Pro Ala Phe Ala Leu Ala Ser Leu Ala Val Ala
1               5                   10                  15

agt cct gac ctt agt cta act tat gac tat gtt att gtt ggt gct gga       96
Ser Pro Asp Leu Ser Leu Thr Tyr Asp Tyr Val Ile Val Gly Ala Gly
            20                  25                  30

aca agt ggt tta gtc att gca aac cgt cta tcc gag ttg aat gtc act      144
Thr Ser Gly Leu Val Ile Ala Asn Arg Leu Ser Glu Leu Asn Val Thr
        35                  40                  45

gtg gcc gtg att gaa gca ggt gat tca ggc tac aac aat gtc aat gtg      192
Val Ala Val Ile Glu Ala Gly Asp Ser Gly Tyr Asn Asn Val Asn Val
    50                  55                  60

act aac ccg gcc ggt tat gga ttg gct ttt gga acc gac atc gat tgg      240
Thr Asn Pro Ala Gly Tyr Gly Leu Ala Phe Gly Thr Asp Ile Asp Trp
65                  70                  75                  80

gca tac caa tca acc aat cag aag tat gca ggg aac gct acg cag act      288
Ala Tyr Gln Ser Thr Asn Gln Lys Tyr Ala Gly Asn Ala Thr Gln Thr
                85                  90                  95

tta cga gct ggg aaa gtc ata gga ggt act agc acg atc aat ggg atg      336
Leu Arg Ala Gly Lys Val Ile Gly Gly Thr Ser Thr Ile Asn Gly Met
            100                 105                 110

gca tac acc cga gct gaa gat gtt cag att gat gct tgg gca gcc ctt      384
Ala Tyr Thr Arg Ala Glu Asp Val Gln Ile Asp Ala Trp Ala Ala Leu
        115                 120                 125

gga aat gat gga tgg aat tgg gag aat tta ttc cca tac tac aag aag      432
Gly Asn Asp Gly Trp Asn Trp Glu Asn Leu Phe Pro Tyr Tyr Lys Lys
    130                 135                 140

tct cag aca ctt caa gct cct acc gct gct caa gct gaa gcc ggt gct      480
Ser Gln Thr Leu Gln Ala Pro Thr Ala Ala Gln Ala Glu Ala Gly Ala
145                 150                 155                 160

aca tac gat cct tcg gca aat gga ttc gat ggg cca ttg aag gtt ggc      528
Thr Tyr Asp Pro Ser Ala Asn Gly Phe Asp Gly Pro Leu Lys Val Gly
                165                 170                 175

tgg ctc aaa agc ttg gcc aat gat gac ttt cac ata att ctg aac gat      576
Trp Leu Lys Ser Leu Ala Asn Asp Asp Phe His Ile Ile Leu Asn Asp
            180                 185                 190

acc tac gct tct ctc ggc att ttt gcg aat gag gat gtc aac act ggt      624
Thr Tyr Ala Ser Leu Gly Ile Phe Ala Asn Glu Asp Val Asn Thr Gly
        195                 200                 205

aga atg gtt ggt tat aat cgc tac cca gtt acc tac gac gaa acc ttg      672
Arg Met Val Gly Tyr Asn Arg Tyr Pro Val Thr Tyr Asp Glu Thr Leu
    210                 215                 220

aac gtt cgt cat gat gcc ggg cga gca tac tat tat cca att gca aac      720
Asn Val Arg His Asp Ala Gly Arg Ala Tyr Tyr Tyr Pro Ile Ala Asn
```

-continued

```
225                 230                 235                 240

cgc acc aac ctt cat ctt tac cca aat acc atg gct caa cgg ctt act      768
Arg Thr Asn Leu His Leu Tyr Pro Asn Thr Met Ala Gln Arg Leu Thr
                245                 250                 255

tgg aaa tct ggt gcc gat gtc cct act gca aat gga gtt gag gta ctt      816
Trp Lys Ser Gly Ala Asp Val Pro Thr Ala Asn Gly Val Glu Val Leu
            260                 265                 270

acc aac aat tca agc atc cca tac acc att tct gca aat tca gaa gtc      864
Thr Asn Asn Ser Ser Ile Pro Tyr Thr Ile Ser Ala Asn Ser Glu Val
        275                 280                 285

att ctt tca gct gga gct ctg gcg tcc cct cta ctt ctc gaa ctt tct      912
Ile Leu Ser Ala Gly Ala Leu Ala Ser Pro Leu Leu Leu Glu Leu Ser
    290                 295                 300

ggc atc gga aat cct tcc ctt tta aac aag tac aac att ccg gtc gtg      960
Gly Ile Gly Asn Pro Ser Leu Leu Asn Lys Tyr Asn Ile Pro Val Val
305                 310                 315                 320

gtt gat ctt cca acc gtc gga gaa aat ctt cag gat caa acg aac aat     1008
Val Asp Leu Pro Thr Val Gly Glu Asn Leu Gln Asp Gln Thr Asn Asn
                325                 330                 335

ggt ctt gca tac aca gtt tca aag gac gcc tcc ttc tct ggg gtc ggt     1056
Gly Leu Ala Tyr Thr Val Ser Lys Asp Ala Ser Phe Ser Gly Val Gly
            340                 345                 350

acc ttg gtc act tat cct tca gcg gct caa gtt ttt ggt tct gaa atc     1104
Thr Leu Val Thr Tyr Pro Ser Ala Ala Gln Val Phe Gly Ser Glu Ile
        355                 360                 365

caa aac atc tcc gct cat gtt ctt gat tct ctt cct tca tat gct gca     1152
Gln Asn Ile Ser Ala His Val Leu Asp Ser Leu Pro Ser Tyr Ala Ala
    370                 375                 380

caa gtc tcg gct gcg tct ggt aat gtt aca aaa gcc gct gat ttg tta     1200
Gln Val Ser Ala Ala Ser Gly Asn Val Thr Lys Ala Ala Asp Leu Leu
385                 390                 395                 400

gaa ttc ttc aaa att caa cat gac ctt att ttt tca acc acc cac ccg     1248
Glu Phe Phe Lys Ile Gln His Asp Leu Ile Phe Ser Thr Thr His Pro
                405                 410                 415

gtt ccc atg gct gag atc ctc gtc ata cca tcc gca aca ggt ttc aag     1296
Val Pro Met Ala Glu Ile Leu Val Ile Pro Ser Ala Thr Gly Phe Lys
            420                 425                 430

tca gag tac tgg gct cta ttg cca ttt gca aga gga aac ata cac atc     1344
Ser Glu Tyr Trp Ala Leu Leu Pro Phe Ala Arg Gly Asn Ile His Ile
        435                 440                 445

act tct tcg ata cca ggc acc cct gcg gcg atc aat cca aat tat tac     1392
Thr Ser Ser Ile Pro Gly Thr Pro Ala Ala Ile Asn Pro Asn Tyr Tyr
    450                 455                 460

atg ctt gac tgg gat atc aca tcg caa atc act act gca aag ttc atc     1440
Met Leu Asp Trp Asp Ile Thr Ser Gln Ile Thr Thr Ala Lys Phe Ile
465                 470                 475                 480

cgt tcc gtc tac gct acc tct cca ttg tcc act ctg gtt ggc tca gaa     1488
Arg Ser Val Tyr Ala Thr Ser Pro Leu Ser Thr Leu Val Gly Ser Glu
                485                 490                 495

act aaa cca ggt ttg gag aca tta tca gca aat gct acc gag gcg gaa     1536
Thr Lys Pro Gly Leu Glu Thr Leu Ser Ala Asn Ala Thr Glu Ala Glu
            500                 505                 510

tgg tct gaa tgg att aaa gct ggc tat cgt ccc aac ttt cac cca gta     1584
Trp Ser Glu Trp Ile Lys Ala Gly Tyr Arg Pro Asn Phe His Pro Val
        515                 520                 525

tca acc gct gct atg atg cca aga gag gtt ggt gga gta gta gat tca     1632
Ser Thr Ala Ala Met Met Pro Arg Glu Val Gly Gly Val Val Asp Ser
    530                 535                 540

aga ttg aag gtc tat ggg aca tca aat gtg aga gtt gtg gat gcc agt     1680
```

-continued

```
Arg Leu Lys Val Tyr Gly Thr Ser Asn Val Arg Val Val Asp Ala Ser
545                 550                 555                 560

gta ctg cct atg cag gtt agt gga cat ttg gtc agt act tta tac gct     1728
Val Leu Pro Met Gln Val Ser Gly His Leu Val Ser Thr Leu Tyr Ala
                565                 570                 575

gta gcg gag aga gcg gca gat ttg atc aag gag gat att taa             1770
Val Ala Glu Arg Ala Ala Asp Leu Ile Lys Glu Asp Ile
            580                 585


<210> SEQ ID NO 2
<211> LENGTH: 589
<212> TYPE: PRT
<213> ORGANISM: Dumontinia tuberosa

<400> SEQUENCE: 2

Met Asn His Leu Leu Pro Ala Phe Ala Leu Ala Ser Leu Ala Val Ala
1               5                   10                  15

Ser Pro Asp Leu Ser Leu Thr Tyr Asp Tyr Val Ile Val Gly Ala Gly
            20                  25                  30

Thr Ser Gly Leu Val Ile Ala Asn Arg Leu Ser Glu Leu Asn Val Thr
        35                  40                  45

Val Ala Val Ile Glu Ala Gly Asp Ser Gly Tyr Asn Asn Val Asn Val
    50                  55                  60

Thr Asn Pro Ala Gly Tyr Gly Leu Ala Phe Gly Thr Asp Ile Asp Trp
65                  70                  75                  80

Ala Tyr Gln Ser Thr Asn Gln Lys Tyr Ala Gly Asn Ala Thr Gln Thr
                85                  90                  95

Leu Arg Ala Gly Lys Val Ile Gly Gly Thr Ser Thr Ile Asn Gly Met
            100                 105                 110

Ala Tyr Thr Arg Ala Glu Asp Val Gln Ile Asp Ala Trp Ala Ala Leu
        115                 120                 125

Gly Asn Asp Gly Trp Asn Trp Glu Asn Leu Phe Pro Tyr Tyr Lys Lys
    130                 135                 140

Ser Gln Thr Leu Gln Ala Pro Thr Ala Ala Gln Ala Glu Ala Gly Ala
145                 150                 155                 160

Thr Tyr Asp Pro Ser Ala Asn Gly Phe Asp Gly Pro Leu Lys Val Gly
                165                 170                 175

Trp Leu Lys Ser Leu Ala Asn Asp Asp Phe His Ile Ile Leu Asn Asp
            180                 185                 190

Thr Tyr Ala Ser Leu Gly Ile Phe Ala Asn Glu Asp Val Asn Thr Gly
        195                 200                 205

Arg Met Val Gly Tyr Asn Arg Tyr Pro Val Thr Tyr Asp Glu Thr Leu
    210                 215                 220

Asn Val Arg His Asp Ala Gly Arg Ala Tyr Tyr Tyr Pro Ile Ala Asn
225                 230                 235                 240

Arg Thr Asn Leu His Leu Tyr Pro Asn Thr Met Ala Gln Arg Leu Thr
                245                 250                 255

Trp Lys Ser Gly Ala Asp Val Pro Thr Ala Asn Gly Val Glu Val Leu
            260                 265                 270

Thr Asn Asn Ser Ser Ile Pro Tyr Thr Ile Ser Ala Asn Ser Glu Val
        275                 280                 285

Ile Leu Ser Ala Gly Ala Leu Ala Ser Pro Leu Leu Leu Glu Leu Ser
    290                 295                 300

Gly Ile Gly Asn Pro Ser Leu Leu Asn Lys Tyr Asn Ile Pro Val Val
305                 310                 315                 320
```

```
Val Asp Leu Pro Thr Val Gly Glu Asn Leu Gln Asp Gln Thr Asn Asn
                325                 330                 335

Gly Leu Ala Tyr Thr Val Ser Lys Asp Ala Ser Phe Ser Gly Val Gly
            340                 345                 350

Thr Leu Val Thr Tyr Pro Ser Ala Ala Gln Val Phe Gly Ser Glu Ile
        355                 360                 365

Gln Asn Ile Ser Ala His Val Leu Asp Ser Leu Pro Ser Tyr Ala Ala
    370                 375                 380

Gln Val Ser Ala Ala Ser Gly Asn Val Thr Lys Ala Ala Asp Leu Leu
385                 390                 395                 400

Glu Phe Phe Lys Ile Gln His Asp Leu Ile Phe Ser Thr Thr His Pro
                405                 410                 415

Val Pro Met Ala Glu Ile Leu Val Ile Pro Ser Ala Thr Gly Phe Lys
            420                 425                 430

Ser Glu Tyr Trp Ala Leu Leu Pro Phe Ala Arg Gly Asn Ile His Ile
        435                 440                 445

Thr Ser Ser Ile Pro Gly Thr Pro Ala Ala Ile Asn Pro Asn Tyr Tyr
    450                 455                 460

Met Leu Asp Trp Asp Ile Thr Ser Gln Ile Thr Thr Ala Lys Phe Ile
465                 470                 475                 480

Arg Ser Val Tyr Ala Thr Ser Pro Leu Ser Thr Leu Val Gly Ser Glu
                485                 490                 495

Thr Lys Pro Gly Leu Glu Thr Leu Ser Ala Asn Ala Thr Glu Ala Glu
            500                 505                 510

Trp Ser Glu Trp Ile Lys Ala Gly Tyr Arg Pro Asn Phe His Pro Val
        515                 520                 525

Ser Thr Ala Ala Met Met Pro Arg Glu Val Gly Gly Val Val Asp Ser
    530                 535                 540

Arg Leu Lys Val Tyr Gly Thr Ser Asn Val Arg Val Val Asp Ala Ser
545                 550                 555                 560

Val Leu Pro Met Gln Val Ser Gly His Leu Val Ser Thr Leu Tyr Ala
                565                 570                 575

Val Ala Glu Arg Ala Ala Asp Leu Ile Lys Glu Asp Ile
            580                 585


<210> SEQ ID NO 3
<211> LENGTH: 1773
<212> TYPE: DNA
<213> ORGANISM: Botrytis tulipae
<220> FEATURE:
<221> NAME/KEY: CDS
<222> LOCATION: (1)..(1773)
<220> FEATURE:
<221> NAME/KEY: sig_peptide
<222> LOCATION: (1)..(57)

<400> SEQUENCE: 3

atg tat cgt tta ctc tct aca ttt gct cta gcc tct ttg gct gca gct       48
Met Tyr Arg Leu Leu Ser Thr Phe Ala Leu Ala Ser Leu Ala Ala Ala
1               5                   10                  15

agc acc gac tct act tta act tat gat tat att gtt att ggt gct gga       96
Ser Thr Asp Ser Thr Leu Thr Tyr Asp Tyr Ile Val Ile Gly Ala Gly
            20                  25                  30

acc agt ggt cta gtc atc gca aac cgt tta tcc gag tta aat gtc act      144
Thr Ser Gly Leu Val Ile Ala Asn Arg Leu Ser Glu Leu Asn Val Thr
        35                  40                  45

gtg gct gtc att gag gca ggt gat tcg ggt tac aac aat ccc aat gtg      192
Val Ala Val Ile Glu Ala Gly Asp Ser Gly Tyr Asn Asn Pro Asn Val
```

-continued

```
    50                  55                  60

aca aac cca tcc ggt tat gga tta tct ttt gga aca gac atc gat tgg      240
Thr Asn Pro Ser Gly Tyr Gly Leu Ser Phe Gly Thr Asp Ile Asp Trp
65                  70                  75                  80

gcg tat caa tcg acc aac cag aag tat gca gga aac acg agc caa gtc      288
Ala Tyr Gln Ser Thr Asn Gln Lys Tyr Ala Gly Asn Thr Ser Gln Val
                85                  90                  95

tta cga gct ggc aaa atc atc gga ggg act agt act atc aat gga atg      336
Leu Arg Ala Gly Lys Ile Ile Gly Gly Thr Ser Thr Ile Asn Gly Met
            100                 105                 110

gca tac acg cga gcg gaa gat gtt caa att gat gct tgg gca gcc att      384
Ala Tyr Thr Arg Ala Glu Asp Val Gln Ile Asp Ala Trp Ala Ala Ile
        115                 120                 125

gga aat gat gga tgg aac tgg gca aat ctt ttc cca tac tac aaa aag      432
Gly Asn Asp Gly Trp Asn Trp Ala Asn Leu Phe Pro Tyr Tyr Lys Lys
    130                 135                 140

tct cag aca ctc gaa atc cct acc act gct caa gtt gaa gct ggt gca      480
Ser Gln Thr Leu Glu Ile Pro Thr Thr Ala Gln Val Glu Ala Gly Ala
145                 150                 155                 160

gca tat gac gcc tca gcg aat gga ttc gat gga cca ctg aag gtt ggc      528
Ala Tyr Asp Ala Ser Ala Asn Gly Phe Asp Gly Pro Leu Lys Val Gly
                165                 170                 175

tgg ctc aac agc ttg gaa gat act agc aac ttc cat aca acc ttg aat      576
Trp Leu Asn Ser Leu Glu Asp Thr Ser Asn Phe His Thr Thr Leu Asn
            180                 185                 190

gat aca ttt gca ggt ctt ggt gtt cct tca aat gat gat gtc aat act      624
Asp Thr Phe Ala Gly Leu Gly Val Pro Ser Asn Asp Asp Val Asn Thr
        195                 200                 205

ggt aga atg gtt ggt tac agt cga tac cca gct act tac gac aga aca      672
Gly Arg Met Val Gly Tyr Ser Arg Tyr Pro Ala Thr Tyr Asp Arg Thr
    210                 215                 220

ttg aac gtt cgt cat gac gct gga cga gca tat tat tat cca att gcc      720
Leu Asn Val Arg His Asp Ala Gly Arg Ala Tyr Tyr Tyr Pro Ile Ala
225                 230                 235                 240

aac cgc acc aat ctt cat ctt tac cca aat act atg gct caa cga ctc      768
Asn Arg Thr Asn Leu His Leu Tyr Pro Asn Thr Met Ala Gln Arg Leu
                245                 250                 255

aca tgg aca tcc gac gct aat acc cct acc gca aat gga gtc gaa gtt      816
Thr Trp Thr Ser Asp Ala Asn Thr Pro Thr Ala Asn Gly Val Glu Val
            260                 265                 270

ctt tcc aac aac tca agc att cca tac act att cat gca aac tcc gaa      864
Leu Ser Asn Asn Ser Ser Ile Pro Tyr Thr Ile His Ala Asn Ser Glu
        275                 280                 285

gtc att ctt tca gct gga gct cta gca tct cct ctt ctt ctc gaa ctt      912
Val Ile Leu Ser Ala Gly Ala Leu Ala Ser Pro Leu Leu Leu Glu Leu
    290                 295                 300

tcc ggt att gga aac cct tcc atc ttg agc aag cac aat atc tca gtt      960
Ser Gly Ile Gly Asn Pro Ser Ile Leu Ser Lys His Asn Ile Ser Val
305                 310                 315                 320

gta gtt gat ctc cca act gta gga gaa aat ctt caa gat caa acg aat     1008
Val Val Asp Leu Pro Thr Val Gly Glu Asn Leu Gln Asp Gln Thr Asn
                325                 330                 335

act ggc ctt gca tac aac agt tca ggc aac acc tct ttc tct gga gct     1056
Thr Gly Leu Ala Tyr Asn Ser Ser Gly Asn Thr Ser Phe Ser Gly Ala
            340                 345                 350

gga acc ttg gta gct tat cct tcc gca gcc caa tta ttt ggt tct gaa     1104
Gly Thr Leu Val Ala Tyr Pro Ser Ala Ala Gln Leu Phe Gly Ser Glu
        355                 360                 365

gtt caa aaa atc tct gct cat gtt ctt caa tct ctt cct tca tat gct     1152
```

-continued

```
Val Gln Lys Ile Ser Ala His Val Leu Gln Ser Leu Pro Ser Tyr Ala
    370                 375                 380

gca caa gta tca gct gca tca ggt aac atc acc aaa gct gca gat ttg     1200
Ala Gln Val Ser Ala Ala Ser Gly Asn Ile Thr Lys Ala Ala Asp Leu
385                 390                 395                 400

ttg aaa ttc ttc aaa att caa cat gat ctg atc ttc tca act acc cac     1248
Leu Lys Phe Phe Lys Ile Gln His Asp Leu Ile Phe Ser Thr Thr His
                405                 410                 415

cca gtt cca atg gct gaa ata ctc atc tca cca tct gca aca gct ttc     1296
Pro Val Pro Met Ala Glu Ile Leu Ile Ser Pro Ser Ala Thr Ala Phe
            420                 425                 430

agc tcg gaa tat tgg gcc ttg tta cca ttt gca aga gga agt att cac     1344
Ser Ser Glu Tyr Trp Ala Leu Leu Pro Phe Ala Arg Gly Ser Ile His
        435                 440                 445

atc aca tct tcc gta gct ggc aca ccc gca gct atc aat cca aat tat     1392
Ile Thr Ser Ser Val Ala Gly Thr Pro Ala Ala Ile Asn Pro Asn Tyr
    450                 455                 460

ttc atg ttt gat tgg gat gtc aca tct caa atc gct acg gcc aag ttt     1440
Phe Met Phe Asp Trp Asp Val Thr Ser Gln Ile Ala Thr Ala Lys Phe
465                 470                 475                 480

att cgc tcc att tat gcg gct tct cca ctg tcc tct ttc gtc gga tca     1488
Ile Arg Ser Ile Tyr Ala Ala Ser Pro Leu Ser Ser Phe Val Gly Ser
                485                 490                 495

gag acc aag cct gga ttg aac aaa gta tca gct aat gct acg gag gct     1536
Glu Thr Lys Pro Gly Leu Asn Lys Val Ser Ala Asn Ala Thr Glu Ala
            500                 505                 510

gaa tgg ttt gat tgg gtt aaa act gct tat cgc tca aac ttc cat cca     1584
Glu Trp Phe Asp Trp Val Lys Thr Ala Tyr Arg Ser Asn Phe His Pro
        515                 520                 525

gta tca acg gct gca atg atg cca aga gag atc ggt gga gtg gta gac     1632
Val Ser Thr Ala Ala Met Met Pro Arg Glu Ile Gly Gly Val Val Asp
    530                 535                 540

tca agg ttg aag gta tat gga aca gca aat gtg aga gtt gtg gat gct     1680
Ser Arg Leu Lys Val Tyr Gly Thr Ala Asn Val Arg Val Val Asp Ala
545                 550                 555                 560

agt ata tta cct atg cag gtt tct gga cat tta gtt agt act ttg tat     1728
Ser Ile Leu Pro Met Gln Val Ser Gly His Leu Val Ser Thr Leu Tyr
                565                 570                 575

gct gtg gca gag aga gca gca gat ttg atc aag gag gac att tag         1773
Ala Val Ala Glu Arg Ala Ala Asp Leu Ile Lys Glu Asp Ile
            580                 585                 590


<210> SEQ ID NO 4
<211> LENGTH: 590
<212> TYPE: PRT
<213> ORGANISM: Botrytis tulipae

<400> SEQUENCE: 4

Met Tyr Arg Leu Leu Ser Thr Phe Ala Leu Ala Ser Leu Ala Ala Ala
1               5                   10                  15

Ser Thr Asp Ser Thr Leu Thr Tyr Asp Tyr Ile Val Ile Gly Ala Gly
            20                  25                  30

Thr Ser Gly Leu Val Ile Ala Asn Arg Leu Ser Glu Leu Asn Val Thr
        35                  40                  45

Val Ala Val Ile Glu Ala Gly Asp Ser Gly Tyr Asn Asn Pro Asn Val
    50                  55                  60

Thr Asn Pro Ser Gly Tyr Gly Leu Ser Phe Gly Thr Asp Ile Asp Trp
65                  70                  75                  80

Ala Tyr Gln Ser Thr Asn Gln Lys Tyr Ala Gly Asn Thr Ser Gln Val
```

-continued

```
                85                  90                  95

Leu Arg Ala Gly Lys Ile Ile Gly Gly Thr Ser Thr Ile Asn Gly Met
            100                 105                 110

Ala Tyr Thr Arg Ala Glu Asp Val Gln Ile Asp Ala Trp Ala Ala Ile
        115                 120                 125

Gly Asn Asp Gly Trp Asn Trp Ala Asn Leu Phe Pro Tyr Tyr Lys Lys
    130                 135                 140

Ser Gln Thr Leu Glu Ile Pro Thr Thr Ala Gln Val Glu Ala Gly Ala
145                 150                 155                 160

Ala Tyr Asp Ala Ser Ala Asn Gly Phe Asp Gly Pro Leu Lys Val Gly
                165                 170                 175

Trp Leu Asn Ser Leu Glu Asp Thr Ser Asn Phe His Thr Thr Leu Asn
            180                 185                 190

Asp Thr Phe Ala Gly Leu Gly Val Pro Ser Asn Asp Asp Val Asn Thr
        195                 200                 205

Gly Arg Met Val Gly Tyr Ser Arg Tyr Pro Ala Thr Tyr Asp Arg Thr
    210                 215                 220

Leu Asn Val Arg His Asp Ala Gly Arg Ala Tyr Tyr Tyr Pro Ile Ala
225                 230                 235                 240

Asn Arg Thr Asn Leu His Leu Tyr Pro Asn Thr Met Ala Gln Arg Leu
                245                 250                 255

Thr Trp Thr Ser Asp Ala Asn Thr Pro Thr Ala Asn Gly Val Glu Val
            260                 265                 270

Leu Ser Asn Asn Ser Ser Ile Pro Tyr Thr Ile His Ala Asn Ser Glu
        275                 280                 285

Val Ile Leu Ser Ala Gly Ala Leu Ala Ser Pro Leu Leu Leu Glu Leu
    290                 295                 300

Ser Gly Ile Gly Asn Pro Ser Ile Leu Ser Lys His Asn Ile Ser Val
305                 310                 315                 320

Val Val Asp Leu Pro Thr Val Gly Glu Asn Leu Gln Asp Gln Thr Asn
                325                 330                 335

Thr Gly Leu Ala Tyr Asn Ser Ser Gly Asn Thr Ser Phe Ser Gly Ala
            340                 345                 350

Gly Thr Leu Val Ala Tyr Pro Ser Ala Ala Gln Leu Phe Gly Ser Glu
        355                 360                 365

Val Gln Lys Ile Ser Ala His Val Leu Gln Ser Leu Pro Ser Tyr Ala
    370                 375                 380

Ala Gln Val Ser Ala Ala Ser Gly Asn Ile Thr Lys Ala Ala Asp Leu
385                 390                 395                 400

Leu Lys Phe Phe Lys Ile Gln His Asp Leu Ile Phe Ser Thr Thr His
                405                 410                 415

Pro Val Pro Met Ala Glu Ile Leu Ile Ser Pro Ser Ala Thr Ala Phe
            420                 425                 430

Ser Ser Glu Tyr Trp Ala Leu Leu Pro Phe Ala Arg Gly Ser Ile His
        435                 440                 445

Ile Thr Ser Ser Val Ala Gly Thr Pro Ala Ala Ile Asn Pro Asn Tyr
    450                 455                 460

Phe Met Phe Asp Trp Asp Val Thr Ser Gln Ile Ala Thr Ala Lys Phe
465                 470                 475                 480

Ile Arg Ser Ile Tyr Ala Ala Ser Pro Leu Ser Ser Phe Val Gly Ser
                485                 490                 495

Glu Thr Lys Pro Gly Leu Asn Lys Val Ser Ala Asn Ala Thr Glu Ala
            500                 505                 510
```

```
Glu Trp Phe Asp Trp Val Lys Thr Ala Tyr Arg Ser Asn Phe His Pro
        515                 520                 525

Val Ser Thr Ala Ala Met Met Pro Arg Glu Ile Gly Gly Val Val Asp
    530                 535                 540

Ser Arg Leu Lys Val Tyr Gly Thr Ala Asn Val Arg Val Val Asp Ala
545                 550                 555                 560

Ser Ile Leu Pro Met Gln Val Ser Gly His Leu Val Ser Thr Leu Tyr
                565                 570                 575

Ala Val Ala Glu Arg Ala Ala Asp Leu Ile Lys Glu Asp Ile
            580                 585                 590


<210> SEQ ID NO 5
<211> LENGTH: 1773
<212> TYPE: DNA
<213> ORGANISM: Ovulinia azaleae
<220> FEATURE:
<221> NAME/KEY: CDS
<222> LOCATION: (1)..(1773)
<220> FEATURE:
<221> NAME/KEY: sig_peptide
<222> LOCATION: (1)..(57)

<400> SEQUENCE: 5

atg tat cgt tta ctc tct aca ttt gct cta gcc tct ttg gct gca gct       48
Met Tyr Arg Leu Leu Ser Thr Phe Ala Leu Ala Ser Leu Ala Ala Ala
1               5                   10                  15

agc acc gac tct act tta act tat gat tat att gtt att ggt gct gga       96
Ser Thr Asp Ser Thr Leu Thr Tyr Asp Tyr Ile Val Ile Gly Ala Gly
            20                  25                  30

acc agt ggt cta gtc atc gca aac cgt tta tcc gag tta aat gtc act      144
Thr Ser Gly Leu Val Ile Ala Asn Arg Leu Ser Glu Leu Asn Val Thr
        35                  40                  45

gtg gct gtc att gag gca ggt gat tcg ggt tac aac aat ccc aat gtg      192
Val Ala Val Ile Glu Ala Gly Asp Ser Gly Tyr Asn Asn Pro Asn Val
    50                  55                  60

aca aac cca tcc ggt tat gga cta tct ttt gga aca gac atc gat tgg      240
Thr Asn Pro Ser Gly Tyr Gly Leu Ser Phe Gly Thr Asp Ile Asp Trp
65                  70                  75                  80

gcg tat caa tcg acc aac cag aag tat gca gga aac acg agc caa gtc      288
Ala Tyr Gln Ser Thr Asn Gln Lys Tyr Ala Gly Asn Thr Ser Gln Val
                85                  90                  95

tta cga gct ggc aaa atc atc gga ggg act agt act atc aat gga atg      336
Leu Arg Ala Gly Lys Ile Ile Gly Gly Thr Ser Thr Ile Asn Gly Met
            100                 105                 110

gca tac acg cga gcg gaa gat gtt caa att gat gct tgg gcg gcc att      384
Ala Tyr Thr Arg Ala Glu Asp Val Gln Ile Asp Ala Trp Ala Ala Ile
        115                 120                 125

gga aat gat gga tgg aac tgg gca aat ctt ttc cca tac tac aaa aag      432
Gly Asn Asp Gly Trp Asn Trp Ala Asn Leu Phe Pro Tyr Tyr Lys Lys
    130                 135                 140

tct cag aca ctc gaa atc cct acc act gct caa gtt gaa gct ggt gca      480
Ser Gln Thr Leu Glu Ile Pro Thr Thr Ala Gln Val Glu Ala Gly Ala
145                 150                 155                 160

gca tat gac gcc tca gcg aat gga ttc gat gga cca ctg aag gtt ggc      528
Ala Tyr Asp Ala Ser Ala Asn Gly Phe Asp Gly Pro Leu Lys Val Gly
                165                 170                 175

tgg ctc aac agc ttg gaa gat act agc aac ttc cat aca acc ttg aat      576
Trp Leu Asn Ser Leu Glu Asp Thr Ser Asn Phe His Thr Thr Leu Asn
            180                 185                 190

gat aca ttt gca ggt ctt ggt gtt cct tca aat gat gat gtc aat act      624
```

-continued

```
Asp Thr Phe Ala Gly Leu Gly Val Pro Ser Asn Asp Asp Val Asn Thr
        195                 200                 205

ggt aga atg gtt ggt tac agt cga tac cca gct act tac gac aga aca      672
Gly Arg Met Val Gly Tyr Ser Arg Tyr Pro Ala Thr Tyr Asp Arg Thr
    210                 215                 220

ttg aac gtt cgt cat gac gct gga cga gca tat tat tat cca att gcc      720
Leu Asn Val Arg His Asp Ala Gly Arg Ala Tyr Tyr Tyr Pro Ile Ala
225                 230                 235                 240

aac cgc acc aat ctt cat ctt tac cca aat act atg gct caa cga ctc      768
Asn Arg Thr Asn Leu His Leu Tyr Pro Asn Thr Met Ala Gln Arg Leu
                245                 250                 255

aca tgg aca tcc gac gct aat acc cct acc gca aat gga gtc gaa gtt      816
Thr Trp Thr Ser Asp Ala Asn Thr Pro Thr Ala Asn Gly Val Glu Val
            260                 265                 270

ctt tcc aac aac tca agc att cca tac act att cat gca aac tcc gaa      864
Leu Ser Asn Asn Ser Ser Ile Pro Tyr Thr Ile His Ala Asn Ser Glu
        275                 280                 285

gtc att ctt tca gct gga gct cta gca tct cct ctt ctt ctc gaa ctt      912
Val Ile Leu Ser Ala Gly Ala Leu Ala Ser Pro Leu Leu Leu Glu Leu
    290                 295                 300

tcc ggt att gga aac cct tcc atc ttg agc agg cac aat atc tca gtt      960
Ser Gly Ile Gly Asn Pro Ser Ile Leu Ser Arg His Asn Ile Ser Val
305                 310                 315                 320

gta gtt gat ctc cca gct gta gga gaa aat ctt caa gat caa acg aat     1008
Val Val Asp Leu Pro Ala Val Gly Glu Asn Leu Gln Asp Gln Thr Asn
                325                 330                 335

acc ggc ctt gca tac aac agt tca ggc aac acc tct ttc tct gga gct     1056
Thr Gly Leu Ala Tyr Asn Ser Ser Gly Asn Thr Ser Phe Ser Gly Ala
            340                 345                 350

gga acc ttg gta gct tat cct tcc gca gcc caa tta ttt ggt tct gaa     1104
Gly Thr Leu Val Ala Tyr Pro Ser Ala Ala Gln Leu Phe Gly Ser Glu
        355                 360                 365

gtt caa aaa atc tct gct cat gtt ctt caa tct ctt cct tca tat gct     1152
Val Gln Lys Ile Ser Ala His Val Leu Gln Ser Leu Pro Ser Tyr Ala
    370                 375                 380

gca caa gta tca gct gca tca ggt aac atc acc aaa gct gca gat ttg     1200
Ala Gln Val Ser Ala Ala Ser Gly Asn Ile Thr Lys Ala Ala Asp Leu
385                 390                 395                 400

ttg aaa ttc ttc aaa att caa cat gat ctg atc ttc tca act acc cac     1248
Leu Lys Phe Phe Lys Ile Gln His Asp Leu Ile Phe Ser Thr Thr His
                405                 410                 415

cca gtt cca atg gct gaa ata ctc atc tca cca tct gca aca gct ttc     1296
Pro Val Pro Met Ala Glu Ile Leu Ile Ser Pro Ser Ala Thr Ala Phe
            420                 425                 430

agc tcg gaa tat tgg gcc ttg tta cca ttt gca aga gga agt att cac     1344
Ser Ser Glu Tyr Trp Ala Leu Leu Pro Phe Ala Arg Gly Ser Ile His
        435                 440                 445

atc aca tct tcc gta gct ggc aca ccc gca gct atc aat cca aat tat     1392
Ile Thr Ser Ser Val Ala Gly Thr Pro Ala Ala Ile Asn Pro Asn Tyr
    450                 455                 460

ttc atg ttt gat tgg gat gtc aca tct caa atc gct acg gcc aag ttt     1440
Phe Met Phe Asp Trp Asp Val Thr Ser Gln Ile Ala Thr Ala Lys Phe
465                 470                 475                 480

att cgc tcc att tat gcg gct tct cca ctg tcc tct ttc gtc gga tca     1488
Ile Arg Ser Ile Tyr Ala Ala Ser Pro Leu Ser Ser Phe Val Gly Ser
                485                 490                 495

gag acc aag cct gga ttg aac aaa gta tca gct aat gct acg gag gct     1536
Glu Thr Lys Pro Gly Leu Asn Lys Val Ser Ala Asn Ala Thr Glu Ala
            500                 505                 510
```

-continued

```
gaa tgg ttt gat tgg gtt aaa act gct tat cgc tca aac ttc cat cca      1584
Glu Trp Phe Asp Trp Val Lys Thr Ala Tyr Arg Ser Asn Phe His Pro
        515                 520                 525

gta tca acg gct gca atg atg cca aga gag atc ggt gga gtg gta gac      1632
Val Ser Thr Ala Ala Met Met Pro Arg Glu Ile Gly Gly Val Val Asp
    530                 535                 540

tca agg ttg aag gta tat gga aca gca aat gtg aga gtt gtg gat gct      1680
Ser Arg Leu Lys Val Tyr Gly Thr Ala Asn Val Arg Val Val Asp Ala
545                 550                 555                 560

agt ata tta cct atg cag gtt tct gga cat tta gtt agt act ttg tat      1728
Ser Ile Leu Pro Met Gln Val Ser Gly His Leu Val Ser Thr Leu Tyr
                565                 570                 575

gct gtg gca gag aga gca gca gat ttg atc aag gaa gac atg tag          1773
Ala Val Ala Glu Arg Ala Ala Asp Leu Ile Lys Glu Asp Met
            580                 585                 590


<210> SEQ ID NO 6
<211> LENGTH: 590
<212> TYPE: PRT
<213> ORGANISM: Ovulinia azaleae

<400> SEQUENCE: 6

Met Tyr Arg Leu Leu Ser Thr Phe Ala Leu Ala Ser Leu Ala Ala Ala
1               5                   10                  15

Ser Thr Asp Ser Thr Leu Thr Tyr Asp Tyr Ile Val Ile Gly Ala Gly
            20                  25                  30

Thr Ser Gly Leu Val Ile Ala Asn Arg Leu Ser Glu Leu Asn Val Thr
        35                  40                  45

Val Ala Val Ile Glu Ala Gly Asp Ser Gly Tyr Asn Asn Pro Asn Val
    50                  55                  60

Thr Asn Pro Ser Gly Tyr Gly Leu Ser Phe Gly Thr Asp Ile Asp Trp
65                  70                  75                  80

Ala Tyr Gln Ser Thr Asn Gln Lys Tyr Ala Gly Asn Thr Ser Gln Val
                85                  90                  95

Leu Arg Ala Gly Lys Ile Ile Gly Gly Thr Ser Thr Ile Asn Gly Met
            100                 105                 110

Ala Tyr Thr Arg Ala Glu Asp Val Gln Ile Asp Ala Trp Ala Ala Ile
        115                 120                 125

Gly Asn Asp Gly Trp Asn Trp Ala Asn Leu Phe Pro Tyr Tyr Lys Lys
    130                 135                 140

Ser Gln Thr Leu Glu Ile Pro Thr Thr Ala Gln Val Glu Ala Gly Ala
145                 150                 155                 160

Ala Tyr Asp Ala Ser Ala Asn Gly Phe Asp Gly Pro Leu Lys Val Gly
                165                 170                 175

Trp Leu Asn Ser Leu Glu Asp Thr Ser Asn Phe His Thr Thr Leu Asn
            180                 185                 190

Asp Thr Phe Ala Gly Leu Gly Val Pro Ser Asn Asp Asp Val Asn Thr
        195                 200                 205

Gly Arg Met Val Gly Tyr Ser Arg Tyr Pro Ala Thr Tyr Asp Arg Thr
    210                 215                 220

Leu Asn Val Arg His Asp Ala Gly Arg Ala Tyr Tyr Tyr Pro Ile Ala
225                 230                 235                 240

Asn Arg Thr Asn Leu His Leu Tyr Pro Asn Thr Met Ala Gln Arg Leu
                245                 250                 255

Thr Trp Thr Ser Asp Ala Asn Thr Pro Thr Ala Asn Gly Val Glu Val
            260                 265                 270
```

```
Leu Ser Asn Asn Ser Ser Ile Pro Tyr Thr Ile His Ala Asn Ser Glu
        275                 280                 285

Val Ile Leu Ser Ala Gly Ala Leu Ala Ser Pro Leu Leu Leu Glu Leu
    290                 295                 300

Ser Gly Ile Gly Asn Pro Ser Ile Leu Ser Arg His Asn Ile Ser Val
305                 310                 315                 320

Val Val Asp Leu Pro Ala Val Gly Glu Asn Leu Gln Asp Gln Thr Asn
                325                 330                 335

Thr Gly Leu Ala Tyr Asn Ser Ser Gly Asn Thr Ser Phe Ser Gly Ala
            340                 345                 350

Gly Thr Leu Val Ala Tyr Pro Ser Ala Ala Gln Leu Phe Gly Ser Glu
        355                 360                 365

Val Gln Lys Ile Ser Ala His Val Leu Gln Ser Leu Pro Ser Tyr Ala
    370                 375                 380

Ala Gln Val Ser Ala Ala Ser Gly Asn Ile Thr Lys Ala Ala Asp Leu
385                 390                 395                 400

Leu Lys Phe Phe Lys Ile Gln His Asp Leu Ile Phe Ser Thr Thr His
                405                 410                 415

Pro Val Pro Met Ala Glu Ile Leu Ile Ser Pro Ser Ala Thr Ala Phe
            420                 425                 430

Ser Ser Glu Tyr Trp Ala Leu Leu Pro Phe Ala Arg Gly Ser Ile His
        435                 440                 445

Ile Thr Ser Ser Val Ala Gly Thr Pro Ala Ala Ile Asn Pro Asn Tyr
    450                 455                 460

Phe Met Phe Asp Trp Asp Val Thr Ser Gln Ile Ala Thr Ala Lys Phe
465                 470                 475                 480

Ile Arg Ser Ile Tyr Ala Ala Ser Pro Leu Ser Ser Phe Val Gly Ser
                485                 490                 495

Glu Thr Lys Pro Gly Leu Asn Lys Val Ser Ala Asn Ala Thr Glu Ala
            500                 505                 510

Glu Trp Phe Asp Trp Val Lys Thr Ala Tyr Arg Ser Asn Phe His Pro
        515                 520                 525

Val Ser Thr Ala Ala Met Met Pro Arg Glu Ile Gly Gly Val Val Asp
    530                 535                 540

Ser Arg Leu Lys Val Tyr Gly Thr Ala Asn Val Arg Val Val Asp Ala
545                 550                 555                 560

Ser Ile Leu Pro Met Gln Val Ser Gly His Leu Val Ser Thr Leu Tyr
                565                 570                 575

Ala Val Ala Glu Arg Ala Ala Asp Leu Ile Lys Glu Asp Met
            580                 585                 590


<210> SEQ ID NO 7
<211> LENGTH: 1776
<212> TYPE: DNA
<213> ORGANISM: Ciborinia camelliae
<220> FEATURE:
<221> NAME/KEY: CDS
<222> LOCATION: (1)..(1776)
<220> FEATURE:
<221> NAME/KEY: sig_peptide
<222> LOCATION: (1)..(57)

<400> SEQUENCE: 7

atg cat cgc ttc ctt cct gcc ttt gtt ctt gcc tcc ttg gct gcc gcg       48
Met His Arg Phe Leu Pro Ala Phe Val Leu Ala Ser Leu Ala Ala Ala
1               5                   10                  15

tct caa gac gtt gcc tta acc tac gat tat gtt atc gtt ggt gct gga       96
```

-continued

```
Ser Gln Asp Val Ala Leu Thr Tyr Asp Tyr Val Ile Val Gly Ala Gly
            20                  25                  30

aca agt ggt ctc gtc act gca cac cgt ctg tcc gag ttg gct gat gtc      144
Thr Ser Gly Leu Val Thr Ala His Arg Leu Ser Glu Leu Ala Asp Val
        35                  40                  45

act gtc gcc gtg att gaa gct ggt gaa tcg aac tac aac aac gcc aat      192
Thr Val Ala Val Ile Glu Ala Gly Glu Ser Asn Tyr Asn Asn Ala Asn
    50                  55                  60

gtc acc aac cct gca ggc tat gga ttg gct ttt ggt acc caa att gat      240
Val Thr Asn Pro Ala Gly Tyr Gly Leu Ala Phe Gly Thr Gln Ile Asp
65                  70                  75                  80

tgg caa tac caa aca acc gtc caa gag tac gga gga gac gtc acc aag      288
Trp Gln Tyr Gln Thr Thr Val Gln Glu Tyr Gly Gly Asp Val Thr Lys
                85                  90                  95

gtt atc cga gct ggt aaa tcc atc gga gga act agc aca atc aac gga      336
Val Ile Arg Ala Gly Lys Ser Ile Gly Gly Thr Ser Thr Ile Asn Gly
            100                 105                 110

atg gct tac acc cga gct gag gat gtt cag gtt gat gca tgg gaa gcc      384
Met Ala Tyr Thr Arg Ala Glu Asp Val Gln Val Asp Ala Trp Glu Ala
        115                 120                 125

ctt gga aat gag gga tgg aac tgg gca aac atg ctc cca tac tac aag      432
Leu Gly Asn Glu Gly Trp Asn Trp Ala Asn Met Leu Pro Tyr Tyr Lys
    130                 135                 140

aag tct caa aca ctt cag gtt cca act gag gcc caa gct gca cta gga      480
Lys Ser Gln Thr Leu Gln Val Pro Thr Glu Ala Gln Ala Ala Leu Gly
145                 150                 155                 160

gca cat tac gac cct gcg tca aac gga tat gaa gga cca ttg aag gtt      528
Ala His Tyr Asp Pro Ala Ser Asn Gly Tyr Glu Gly Pro Leu Lys Val
                165                 170                 175

ggt tgg gtc aac gcc atg gcc acc gat gac ttc cac aca att ttg aac      576
Gly Trp Val Asn Ala Met Ala Thr Asp Asp Phe His Thr Ile Leu Asn
            180                 185                 190

gag acc tac gct gct ctc gac gtt ccc gcc aac aac gat gtc aac act      624
Glu Thr Tyr Ala Ala Leu Asp Val Pro Ala Asn Asn Asp Val Asn Thr
        195                 200                 205

ggt aag atg atc ggt tac acc aga tac cca gct acc tac gac aga acc      672
Gly Lys Met Ile Gly Tyr Thr Arg Tyr Pro Ala Thr Tyr Asp Arg Thr
    210                 215                 220

ttg aac atg cgt tgt gat gcc gga aga gcc tac tac tac cca atc cag      720
Leu Asn Met Arg Cys Asp Ala Gly Arg Ala Tyr Tyr Tyr Pro Ile Gln
225                 230                 235                 240

aac cgt acc aac ctt cat ctt tac cca aac acc atg gcc cag cgt ctt      768
Asn Arg Thr Asn Leu His Leu Tyr Pro Asn Thr Met Ala Gln Arg Leu
                245                 250                 255

aca tgg aaa tcc ggt gcc tcc acc ccc act gca gag gga gtt gag gtt      816
Thr Trp Lys Ser Gly Ala Ser Thr Pro Thr Ala Glu Gly Val Glu Val
            260                 265                 270

ctt gcc gac ggc gag acc acc cca tac acc att cac gca agc tcc gaa      864
Leu Ala Asp Gly Glu Thr Thr Pro Tyr Thr Ile His Ala Ser Ser Glu
        275                 280                 285

gtc atc atc tcc gcc ggt gct ctt ggt tcc cct ctt gtt ctc gag cac      912
Val Ile Ile Ser Ala Gly Ala Leu Gly Ser Pro Leu Val Leu Glu His
    290                 295                 300

tct ggt att ggt aac cct gct atc ctt gag aag tac aac att tcc gtc      960
Ser Gly Ile Gly Asn Pro Ala Ile Leu Glu Lys Tyr Asn Ile Ser Val
305                 310                 315                 320

gtc gtt gat ctc cca acc gtc gga gag aat ctt cag gat caa aca aac     1008
Val Val Asp Leu Pro Thr Val Gly Glu Asn Leu Gln Asp Gln Thr Asn
                325                 330                 335
```

-continued

```
acc gct ctt ggt ttc gac acc tca agc gac aat gtc act tac tca gcc      1056
Thr Ala Leu Gly Phe Asp Thr Ser Ser Asp Asn Val Thr Tyr Ser Ala
            340                 345                 350

gtt tct acc tac ctc ggt tac cca tct gct gct cag atg ttc ggt tcc      1104
Val Ser Thr Tyr Leu Gly Tyr Pro Ser Ala Ala Gln Met Phe Gly Ser
        355                 360                 365

gat ttc aag acc gtc gcc gct gaa att ctc gct gct ctt cct tcc tat      1152
Asp Phe Lys Thr Val Ala Ala Glu Ile Leu Ala Ala Leu Pro Ser Tyr
    370                 375                 380

gcc gac aag gtc gcc att gca tca ggc aat gtt acc aag gcc gct gat      1200
Ala Asp Lys Val Ala Ile Ala Ser Gly Asn Val Thr Lys Ala Ala Asp
385                 390                 395                 400

ttg ttg aag ttc ttc aag att caa tac gag ctc atc ttc agc gcc acc      1248
Leu Leu Lys Phe Phe Lys Ile Gln Tyr Glu Leu Ile Phe Ser Ala Thr
                405                 410                 415

agc cct gtc cct gtc gcc gag ctt ctc gtt acc cca gtt gga acc acc      1296
Ser Pro Val Pro Val Ala Glu Leu Leu Val Thr Pro Val Gly Thr Thr
            420                 425                 430

tac agt gcc gag ttc tgg tcc ttg ttg cca ttc tcc cgt gga aac atc      1344
Tyr Ser Ala Glu Phe Trp Ser Leu Leu Pro Phe Ser Arg Gly Asn Ile
        435                 440                 445

cac atc tca tct gcc acc cca ggt gtc gcc gca acc atc aac cca aac      1392
His Ile Ser Ser Ala Thr Pro Gly Val Ala Ala Thr Ile Asn Pro Asn
    450                 455                 460

tac ttc atg ctt gat tat gat atg atc tcg caa gtc cgc tcc gcc aag      1440
Tyr Phe Met Leu Asp Tyr Asp Met Ile Ser Gln Val Arg Ser Ala Lys
465                 470                 475                 480

tac att cgt gag atc ttt gcc acc act cca ttg tcc cct ctc gtt ggc      1488
Tyr Ile Arg Glu Ile Phe Ala Thr Thr Pro Leu Ser Pro Leu Val Gly
                485                 490                 495

agc gaa acc acc cct ggt ttg gac tct att gcc tca gct gcc acc gag      1536
Ser Glu Thr Thr Pro Gly Leu Asp Ser Ile Ala Ser Ala Ala Thr Glu
            500                 505                 510

gcc gaa tgg gcc gct tgg gtc aag acc gcc tac cga tcc aac ttc cac      1584
Ala Glu Trp Ala Ala Trp Val Lys Thr Ala Tyr Arg Ser Asn Phe His
        515                 520                 525

ccc gtc gcc acc gct gcc atg atg cca cgc gag atc gga gga gtc gtc      1632
Pro Val Ala Thr Ala Ala Met Met Pro Arg Glu Ile Gly Gly Val Val
    530                 535                 540

gac tcc cgc ttg aag gtc tac gga acc acc aac gtc aga gtc gtc gat      1680
Asp Ser Arg Leu Lys Val Tyr Gly Thr Thr Asn Val Arg Val Val Asp
545                 550                 555                 560

gcc agt atc ttg ccc atg caa gtt tgc gga cat ttg acc agt act ttg      1728
Ala Ser Ile Leu Pro Met Gln Val Cys Gly His Leu Thr Ser Thr Leu
                565                 570                 575

tac gcc atg tcc gag aga gcc gct gac ttg atc aag gaa gat atg taa      1776
Tyr Ala Met Ser Glu Arg Ala Ala Asp Leu Ile Lys Glu Asp Met
            580                 585                 590


<210> SEQ ID NO 8
<211> LENGTH: 591
<212> TYPE: PRT
<213> ORGANISM: Ciborinia camelliae

<400> SEQUENCE: 8

Met His Arg Phe Leu Pro Ala Phe Val Leu Ala Ser Leu Ala Ala Ala
1               5                   10                  15

Ser Gln Asp Val Ala Leu Thr Tyr Asp Tyr Val Ile Val Gly Ala Gly
            20                  25                  30

Thr Ser Gly Leu Val Thr Ala His Arg Leu Ser Glu Leu Ala Asp Val
```

-continued

```
        35                  40                  45

Thr Val Ala Val Ile Glu Ala Gly Glu Ser Asn Tyr Asn Asn Ala Asn
    50                  55                  60

Val Thr Asn Pro Ala Gly Tyr Gly Leu Ala Phe Gly Thr Gln Ile Asp
65                  70                  75                  80

Trp Gln Tyr Gln Thr Thr Val Gln Glu Tyr Gly Gly Asp Val Thr Lys
                85                  90                  95

Val Ile Arg Ala Gly Lys Ser Ile Gly Gly Thr Ser Thr Ile Asn Gly
            100                 105                 110

Met Ala Tyr Thr Arg Ala Glu Asp Val Gln Val Asp Ala Trp Glu Ala
        115                 120                 125

Leu Gly Asn Glu Gly Trp Asn Trp Ala Asn Met Leu Pro Tyr Tyr Lys
    130                 135                 140

Lys Ser Gln Thr Leu Gln Val Pro Thr Glu Ala Gln Ala Ala Leu Gly
145                 150                 155                 160

Ala His Tyr Asp Pro Ala Ser Asn Gly Tyr Glu Gly Pro Leu Lys Val
                165                 170                 175

Gly Trp Val Asn Ala Met Ala Thr Asp Asp Phe His Thr Ile Leu Asn
            180                 185                 190

Glu Thr Tyr Ala Ala Leu Asp Val Pro Ala Asn Asn Asp Val Asn Thr
        195                 200                 205

Gly Lys Met Ile Gly Tyr Thr Arg Tyr Pro Ala Thr Tyr Asp Arg Thr
    210                 215                 220

Leu Asn Met Arg Cys Asp Ala Gly Arg Ala Tyr Tyr Tyr Pro Ile Gln
225                 230                 235                 240

Asn Arg Thr Asn Leu His Leu Tyr Pro Asn Thr Met Ala Gln Arg Leu
                245                 250                 255

Thr Trp Lys Ser Gly Ala Ser Thr Pro Thr Ala Glu Gly Val Glu Val
            260                 265                 270

Leu Ala Asp Gly Glu Thr Thr Pro Tyr Thr Ile His Ala Ser Ser Glu
        275                 280                 285

Val Ile Ile Ser Ala Gly Ala Leu Gly Ser Pro Leu Val Leu Glu His
    290                 295                 300

Ser Gly Ile Gly Asn Pro Ala Ile Leu Glu Lys Tyr Asn Ile Ser Val
305                 310                 315                 320

Val Val Asp Leu Pro Thr Val Gly Glu Asn Leu Gln Asp Gln Thr Asn
                325                 330                 335

Thr Ala Leu Gly Phe Asp Thr Ser Ser Asp Asn Val Thr Tyr Ser Ala
            340                 345                 350

Val Ser Thr Tyr Leu Gly Tyr Pro Ser Ala Ala Gln Met Phe Gly Ser
        355                 360                 365

Asp Phe Lys Thr Val Ala Ala Glu Ile Leu Ala Ala Leu Pro Ser Tyr
    370                 375                 380

Ala Asp Lys Val Ala Ile Ala Ser Gly Asn Val Thr Lys Ala Ala Asp
385                 390                 395                 400

Leu Leu Lys Phe Phe Lys Ile Gln Tyr Glu Leu Ile Phe Ser Ala Thr
                405                 410                 415

Ser Pro Val Pro Val Ala Glu Leu Leu Val Thr Pro Val Gly Thr Thr
            420                 425                 430

Tyr Ser Ala Glu Phe Trp Ser Leu Leu Pro Phe Ser Arg Gly Asn Ile
        435                 440                 445

His Ile Ser Ser Ala Thr Pro Gly Val Ala Ala Thr Ile Asn Pro Asn
    450                 455                 460
```

```
Tyr Phe Met Leu Asp Tyr Asp Met Ile Ser Gln Val Arg Ser Ala Lys
465                 470                 475                 480

Tyr Ile Arg Glu Ile Phe Ala Thr Thr Pro Leu Ser Pro Leu Val Gly
                485                 490                 495

Ser Glu Thr Thr Pro Gly Leu Asp Ser Ile Ala Ser Ala Ala Thr Glu
            500                 505                 510

Ala Glu Trp Ala Ala Trp Val Lys Thr Ala Tyr Arg Ser Asn Phe His
        515                 520                 525

Pro Val Ala Thr Ala Ala Met Met Pro Arg Glu Ile Gly Gly Val Val
    530                 535                 540

Asp Ser Arg Leu Lys Val Tyr Gly Thr Thr Asn Val Arg Val Val Asp
545                 550                 555                 560

Ala Ser Ile Leu Pro Met Gln Val Cys Gly His Leu Thr Ser Thr Leu
                565                 570                 575

Tyr Ala Met Ser Glu Arg Ala Ala Asp Leu Ile Lys Glu Asp Met
            580                 585                 590


<210> SEQ ID NO 9
<211> LENGTH: 1713
<212> TYPE: DNA
<213> ORGANISM: Dumontinia tuberosa
<220> FEATURE:
<221> NAME/KEY: CDS
<222> LOCATION: (1)..(1713)

<400> SEQUENCE: 9

ctt agt cta act tat gac tat gtt att gtt ggt gct gga aca agt ggt       48
Leu Ser Leu Thr Tyr Asp Tyr Val Ile Val Gly Ala Gly Thr Ser Gly
1               5                   10                  15

tta gtc att gca aac cgt cta tcc gag ttg aat gtc act gtg gcc gtg       96
Leu Val Ile Ala Asn Arg Leu Ser Glu Leu Asn Val Thr Val Ala Val
            20                  25                  30

att gaa gca ggt gat tca ggc tac aac aat gtc aat gtg act aac ccg      144
Ile Glu Ala Gly Asp Ser Gly Tyr Asn Asn Val Asn Val Thr Asn Pro
        35                  40                  45

gcc ggt tat gga ttg gct ttt gga acc gac atc gat tgg gca tac caa      192
Ala Gly Tyr Gly Leu Ala Phe Gly Thr Asp Ile Asp Trp Ala Tyr Gln
    50                  55                  60

tca acc aat cag aag tat gca ggg aac gct acg cag act tta cga gct      240
Ser Thr Asn Gln Lys Tyr Ala Gly Asn Ala Thr Gln Thr Leu Arg Ala
65                  70                  75                  80

ggg aaa gtc ata gga ggt act agc acg atc aat ggg atg gca tac acc      288
Gly Lys Val Ile Gly Gly Thr Ser Thr Ile Asn Gly Met Ala Tyr Thr
                85                  90                  95

cga gct gaa gat gtt cag att gat gct tgg gca gcc ctt gga aat gat      336
Arg Ala Glu Asp Val Gln Ile Asp Ala Trp Ala Ala Leu Gly Asn Asp
            100                 105                 110

gga tgg aat tgg gag aat tta ttc cca tac tac aag aag tct cag aca      384
Gly Trp Asn Trp Glu Asn Leu Phe Pro Tyr Tyr Lys Lys Ser Gln Thr
        115                 120                 125

ctt caa gct cct acc gct gct caa gct gaa gcc ggt gct aca tac gat      432
Leu Gln Ala Pro Thr Ala Ala Gln Ala Glu Ala Gly Ala Thr Tyr Asp
    130                 135                 140

cct tcg gca aat gga ttc gat ggg cca ttg aag gtt ggc tgg ctc aaa      480
Pro Ser Ala Asn Gly Phe Asp Gly Pro Leu Lys Val Gly Trp Leu Lys
145                 150                 155                 160

agc ttg gcc aat gat gac ttt cac ata att ctg aac gat acc tac gct      528
Ser Leu Ala Asn Asp Asp Phe His Ile Ile Leu Asn Asp Thr Tyr Ala
                165                 170                 175
```

-continued

```
tct ctc ggc att ttt gcg aat gag gat gtc aac act ggt aga atg gtt      576
Ser Leu Gly Ile Phe Ala Asn Glu Asp Val Asn Thr Gly Arg Met Val
            180                 185                 190

ggt tat aat cgc tac cca gtt acc tac gac gaa acc ttg aac gtt cgt      624
Gly Tyr Asn Arg Tyr Pro Val Thr Tyr Asp Glu Thr Leu Asn Val Arg
        195                 200                 205

cat gat gcc ggg cga gca tac tat tat cca att gca aac cgc acc aac      672
His Asp Ala Gly Arg Ala Tyr Tyr Tyr Pro Ile Ala Asn Arg Thr Asn
    210                 215                 220

ctt cat ctt tac cca aat acc atg gct caa cgg ctt act tgg aaa tct      720
Leu His Leu Tyr Pro Asn Thr Met Ala Gln Arg Leu Thr Trp Lys Ser
225                 230                 235                 240

ggt gcc gat gtc cct act gca aat gga gtt gag gta ctt acc aac aat      768
Gly Ala Asp Val Pro Thr Ala Asn Gly Val Glu Val Leu Thr Asn Asn
                245                 250                 255

tca agc atc cca tac acc att tct gca aat tca gaa gtc att ctt tca      816
Ser Ser Ile Pro Tyr Thr Ile Ser Ala Asn Ser Glu Val Ile Leu Ser
            260                 265                 270

gct gga gct ctg gcg tcc cct cta ctt ctc gaa ctt tct ggc atc gga      864
Ala Gly Ala Leu Ala Ser Pro Leu Leu Leu Glu Leu Ser Gly Ile Gly
        275                 280                 285

aat cct tcc ctt tta aac aag tac aac att ccg gtc gtg gtt gat ctt      912
Asn Pro Ser Leu Leu Asn Lys Tyr Asn Ile Pro Val Val Val Asp Leu
    290                 295                 300

cca acc gtc gga gaa aat ctt cag gat caa acg aac aat ggt ctt gca      960
Pro Thr Val Gly Glu Asn Leu Gln Asp Gln Thr Asn Asn Gly Leu Ala
305                 310                 315                 320

tac aca gtt tca aag gac gcc tcc ttc tct ggg gtc ggt acc ttg gtc     1008
Tyr Thr Val Ser Lys Asp Ala Ser Phe Ser Gly Val Gly Thr Leu Val
                325                 330                 335

act tat cct tca gcg gct caa gtt ttt ggt tct gaa atc caa aac atc     1056
Thr Tyr Pro Ser Ala Ala Gln Val Phe Gly Ser Glu Ile Gln Asn Ile
            340                 345                 350

tcc gct cat gtt ctt gat tct ctt cct tca tat gct gca caa gtc tcg     1104
Ser Ala His Val Leu Asp Ser Leu Pro Ser Tyr Ala Ala Gln Val Ser
        355                 360                 365

gct gcg tct ggt aat gtt aca aaa gcc gct gat ttg tta gaa ttc ttc     1152
Ala Ala Ser Gly Asn Val Thr Lys Ala Ala Asp Leu Leu Glu Phe Phe
    370                 375                 380

aaa att caa cat gac ctt att ttt tca acc acc cac ccg gtt ccc atg     1200
Lys Ile Gln His Asp Leu Ile Phe Ser Thr Thr His Pro Val Pro Met
385                 390                 395                 400

gct gag atc ctc gtc ata cca tcc gca aca ggt ttc aag tca gag tac     1248
Ala Glu Ile Leu Val Ile Pro Ser Ala Thr Gly Phe Lys Ser Glu Tyr
                405                 410                 415

tgg gct cta ttg cca ttt gca aga gga aac ata cac atc act tct tcg     1296
Trp Ala Leu Leu Pro Phe Ala Arg Gly Asn Ile His Ile Thr Ser Ser
            420                 425                 430

ata cca ggc acc cct gcg gcg atc aat cca aat tat tac atg ctt gac     1344
Ile Pro Gly Thr Pro Ala Ala Ile Asn Pro Asn Tyr Tyr Met Leu Asp
        435                 440                 445

tgg gat atc aca tcg caa atc act act gca aag ttc atc cgt tcc gtc     1392
Trp Asp Ile Thr Ser Gln Ile Thr Thr Ala Lys Phe Ile Arg Ser Val
    450                 455                 460

tac gct acc tct cca ttg tcc act ctg gtt ggc tca gaa act aaa cca     1440
Tyr Ala Thr Ser Pro Leu Ser Thr Leu Val Gly Ser Glu Thr Lys Pro
465                 470                 475                 480

ggt ttg gag aca tta tca gca aat gct acc gag gcg gaa tgg tct gaa     1488
Gly Leu Glu Thr Leu Ser Ala Asn Ala Thr Glu Ala Glu Trp Ser Glu
```

-continued

```
                485                 490                 495

tgg att aaa gct ggc tat cgt ccc aac ttt cac cca gta tca acc gct      1536
Trp Ile Lys Ala Gly Tyr Arg Pro Asn Phe His Pro Val Ser Thr Ala
            500                 505                 510

gct atg atg cca aga gag gtt ggt gga gta gta gat tca aga ttg aag      1584
Ala Met Met Pro Arg Glu Val Gly Gly Val Val Asp Ser Arg Leu Lys
        515                 520                 525

gtc tat ggg aca tca aat gtg aga gtt gtg gat gcc agt gta ctg cct      1632
Val Tyr Gly Thr Ser Asn Val Arg Val Val Asp Ala Ser Val Leu Pro
    530                 535                 540

atg cag gtt agt gga cat ttg gtc agt act tta tac gct gta gcg gag      1680
Met Gln Val Ser Gly His Leu Val Ser Thr Leu Tyr Ala Val Ala Glu
545                 550                 555                 560

aga gcg gca gat ttg atc aag gag gat att taa                          1713
Arg Ala Ala Asp Leu Ile Lys Glu Asp Ile
                565                 570


<210> SEQ ID NO 10
<211> LENGTH: 570
<212> TYPE: PRT
<213> ORGANISM: Dumontinia tuberosa

<400> SEQUENCE: 10

Leu Ser Leu Thr Tyr Asp Tyr Val Ile Val Gly Ala Gly Thr Ser Gly
1               5                   10                  15

Leu Val Ile Ala Asn Arg Leu Ser Glu Leu Asn Val Thr Val Ala Val
            20                  25                  30

Ile Glu Ala Gly Asp Ser Gly Tyr Asn Asn Val Asn Val Thr Asn Pro
        35                  40                  45

Ala Gly Tyr Gly Leu Ala Phe Gly Thr Asp Ile Asp Trp Ala Tyr Gln
    50                  55                  60

Ser Thr Asn Gln Lys Tyr Ala Gly Asn Ala Thr Gln Thr Leu Arg Ala
65                  70                  75                  80

Gly Lys Val Ile Gly Gly Thr Ser Thr Ile Asn Gly Met Ala Tyr Thr
                85                  90                  95

Arg Ala Glu Asp Val Gln Ile Asp Ala Trp Ala Ala Leu Gly Asn Asp
            100                 105                 110

Gly Trp Asn Trp Glu Asn Leu Phe Pro Tyr Tyr Lys Lys Ser Gln Thr
        115                 120                 125

Leu Gln Ala Pro Thr Ala Ala Gln Ala Glu Ala Gly Ala Thr Tyr Asp
    130                 135                 140

Pro Ser Ala Asn Gly Phe Asp Gly Pro Leu Lys Val Gly Trp Leu Lys
145                 150                 155                 160

Ser Leu Ala Asn Asp Asp Phe His Ile Ile Leu Asn Asp Thr Tyr Ala
                165                 170                 175

Ser Leu Gly Ile Phe Ala Asn Glu Asp Val Asn Thr Gly Arg Met Val
            180                 185                 190

Gly Tyr Asn Arg Tyr Pro Val Thr Tyr Asp Glu Thr Leu Asn Val Arg
        195                 200                 205

His Asp Ala Gly Arg Ala Tyr Tyr Tyr Pro Ile Ala Asn Arg Thr Asn
    210                 215                 220

Leu His Leu Tyr Pro Asn Thr Met Ala Gln Arg Leu Thr Trp Lys Ser
225                 230                 235                 240

Gly Ala Asp Val Pro Thr Ala Asn Gly Val Glu Val Leu Thr Asn Asn
                245                 250                 255

Ser Ser Ile Pro Tyr Thr Ile Ser Ala Asn Ser Glu Val Ile Leu Ser
```

```
            260                 265                 270

Ala Gly Ala Leu Ala Ser Pro Leu Leu Leu Glu Leu Ser Gly Ile Gly
        275                 280                 285

Asn Pro Ser Leu Leu Asn Lys Tyr Asn Ile Pro Val Val Val Asp Leu
    290                 295                 300

Pro Thr Val Gly Glu Asn Leu Gln Asp Gln Thr Asn Asn Gly Leu Ala
305                 310                 315                 320

Tyr Thr Val Ser Lys Asp Ala Ser Phe Ser Gly Val Gly Thr Leu Val
                325                 330                 335

Thr Tyr Pro Ser Ala Ala Gln Val Phe Gly Ser Glu Ile Gln Asn Ile
            340                 345                 350

Ser Ala His Val Leu Asp Ser Leu Pro Ser Tyr Ala Ala Gln Val Ser
        355                 360                 365

Ala Ala Ser Gly Asn Val Thr Lys Ala Ala Asp Leu Leu Glu Phe Phe
    370                 375                 380

Lys Ile Gln His Asp Leu Ile Phe Ser Thr Thr His Pro Val Pro Met
385                 390                 395                 400

Ala Glu Ile Leu Val Ile Pro Ser Ala Thr Gly Phe Lys Ser Glu Tyr
                405                 410                 415

Trp Ala Leu Leu Pro Phe Ala Arg Gly Asn Ile His Ile Thr Ser Ser
            420                 425                 430

Ile Pro Gly Thr Pro Ala Ala Ile Asn Pro Asn Tyr Tyr Met Leu Asp
        435                 440                 445

Trp Asp Ile Thr Ser Gln Ile Thr Thr Ala Lys Phe Ile Arg Ser Val
    450                 455                 460

Tyr Ala Thr Ser Pro Leu Ser Thr Leu Val Gly Ser Glu Thr Lys Pro
465                 470                 475                 480

Gly Leu Glu Thr Leu Ser Ala Asn Ala Thr Glu Ala Glu Trp Ser Glu
                485                 490                 495

Trp Ile Lys Ala Gly Tyr Arg Pro Asn Phe His Pro Val Ser Thr Ala
            500                 505                 510

Ala Met Met Pro Arg Glu Val Gly Gly Val Val Asp Ser Arg Leu Lys
        515                 520                 525

Val Tyr Gly Thr Ser Asn Val Arg Val Val Asp Ala Ser Val Leu Pro
    530                 535                 540

Met Gln Val Ser Gly His Leu Val Ser Thr Leu Tyr Ala Val Ala Glu
545                 550                 555                 560

Arg Ala Ala Asp Leu Ile Lys Glu Asp Ile
                565                 570


<210> SEQ ID NO 11
<211> LENGTH: 1716
<212> TYPE: DNA
<213> ORGANISM: Botrytis tulipae
<220> FEATURE:
<221> NAME/KEY: CDS
<222> LOCATION: (1)..(1716)

<400> SEQUENCE: 11

tct act tta act tat gat tat att gtt att ggt gct gga acc agt ggt       48
Ser Thr Leu Thr Tyr Asp Tyr Ile Val Ile Gly Ala Gly Thr Ser Gly
1               5                   10                  15

cta gtc atc gca aac cgt tta tcc gag tta aat gtc act gtg gct gtc       96
Leu Val Ile Ala Asn Arg Leu Ser Glu Leu Asn Val Thr Val Ala Val
            20                  25                  30

att gag gca ggt gat tcg ggt tac aac aat ccc aat gtg aca aac cca      144
```

-continued

```
Ile Glu Ala Gly Asp Ser Gly Tyr Asn Asn Pro Asn Val Thr Asn Pro
        35                  40                  45

tcc ggt tat gga tta tct ttt gga aca gac atc gat tgg gcg tat caa      192
Ser Gly Tyr Gly Leu Ser Phe Gly Thr Asp Ile Asp Trp Ala Tyr Gln
    50                  55                  60

tcg acc aac cag aag tat gca gga aac acg agc caa gtc tta cga gct      240
Ser Thr Asn Gln Lys Tyr Ala Gly Asn Thr Ser Gln Val Leu Arg Ala
65                  70                  75                  80

ggc aaa atc atc gga ggg act agt act atc aat gga atg gca tac acg      288
Gly Lys Ile Ile Gly Gly Thr Ser Thr Ile Asn Gly Met Ala Tyr Thr
                85                  90                  95

cga gcg gaa gat gtt caa att gat gct tgg gca gcc att gga aat gat      336
Arg Ala Glu Asp Val Gln Ile Asp Ala Trp Ala Ala Ile Gly Asn Asp
            100                 105                 110

gga tgg aac tgg gca aat ctt ttc cca tac tac aaa aag tct cag aca      384
Gly Trp Asn Trp Ala Asn Leu Phe Pro Tyr Tyr Lys Lys Ser Gln Thr
        115                 120                 125

ctc gaa atc cct acc act gct caa gtt gaa gct ggt gca gca tat gac      432
Leu Glu Ile Pro Thr Thr Ala Gln Val Glu Ala Gly Ala Ala Tyr Asp
    130                 135                 140

gcc tca gcg aat gga ttc gat gga cca ctg aag gtt ggc tgg ctc aac      480
Ala Ser Ala Asn Gly Phe Asp Gly Pro Leu Lys Val Gly Trp Leu Asn
145                 150                 155                 160

agc ttg gaa gat act agc aac ttc cat aca acc ttg aat gat aca ttt      528
Ser Leu Glu Asp Thr Ser Asn Phe His Thr Thr Leu Asn Asp Thr Phe
                165                 170                 175

gca ggt ctt ggt gtt cct tca aat gat gat gtc aat act ggt aga atg      576
Ala Gly Leu Gly Val Pro Ser Asn Asp Asp Val Asn Thr Gly Arg Met
            180                 185                 190

gtt ggt tac agt cga tac cca gct act tac gac aga aca ttg aac gtt      624
Val Gly Tyr Ser Arg Tyr Pro Ala Thr Tyr Asp Arg Thr Leu Asn Val
        195                 200                 205

cgt cat gac gct gga cga gca tat tat tat cca att gcc aac cgc acc      672
Arg His Asp Ala Gly Arg Ala Tyr Tyr Tyr Pro Ile Ala Asn Arg Thr
    210                 215                 220

aat ctt cat ctt tac cca aat act atg gct caa cga ctc aca tgg aca      720
Asn Leu His Leu Tyr Pro Asn Thr Met Ala Gln Arg Leu Thr Trp Thr
225                 230                 235                 240

tcc gac gct aat acc cct acc gca aat gga gtc gaa gtt ctt tcc aac      768
Ser Asp Ala Asn Thr Pro Thr Ala Asn Gly Val Glu Val Leu Ser Asn
                245                 250                 255

aac tca agc att cca tac act att cat gca aac tcc gaa gtc att ctt      816
Asn Ser Ser Ile Pro Tyr Thr Ile His Ala Asn Ser Glu Val Ile Leu
            260                 265                 270

tca gct gga gct cta gca tct cct ctt ctt ctc gaa ctt tcc ggt att      864
Ser Ala Gly Ala Leu Ala Ser Pro Leu Leu Leu Glu Leu Ser Gly Ile
        275                 280                 285

gga aac cct tcc atc ttg agc aag cac aat atc tca gtt gta gtt gat      912
Gly Asn Pro Ser Ile Leu Ser Lys His Asn Ile Ser Val Val Val Asp
    290                 295                 300

ctc cca act gta gga gaa aat ctt caa gat caa acg aat act ggc ctt      960
Leu Pro Thr Val Gly Glu Asn Leu Gln Asp Gln Thr Asn Thr Gly Leu
305                 310                 315                 320

gca tac aac agt tca ggc aac acc tct ttc tct gga gct gga acc ttg     1008
Ala Tyr Asn Ser Ser Gly Asn Thr Ser Phe Ser Gly Ala Gly Thr Leu
                325                 330                 335

gta gct tat cct tcc gca gcc caa tta ttt ggt tct gaa gtt caa aaa     1056
Val Ala Tyr Pro Ser Ala Ala Gln Leu Phe Gly Ser Glu Val Gln Lys
            340                 345                 350
```

-continued

```
atc tct gct cat gtt ctt caa tct ctt cct tca tat gct gca caa gta     1104
Ile Ser Ala His Val Leu Gln Ser Leu Pro Ser Tyr Ala Ala Gln Val
        355                 360                 365

tca gct gca tca ggt aac atc acc aaa gct gca gat ttg ttg aaa ttc     1152
Ser Ala Ala Ser Gly Asn Ile Thr Lys Ala Ala Asp Leu Leu Lys Phe
    370                 375                 380

ttc aaa att caa cat gat ctg atc ttc tca act acc cac cca gtt cca     1200
Phe Lys Ile Gln His Asp Leu Ile Phe Ser Thr Thr His Pro Val Pro
385                 390                 395                 400

atg gct gaa ata ctc atc tca cca tct gca aca gct ttc agc tcg gaa     1248
Met Ala Glu Ile Leu Ile Ser Pro Ser Ala Thr Ala Phe Ser Ser Glu
                405                 410                 415

tat tgg gcc ttg tta cca ttt gca aga gga agt att cac atc aca tct     1296
Tyr Trp Ala Leu Leu Pro Phe Ala Arg Gly Ser Ile His Ile Thr Ser
            420                 425                 430

tcc gta gct ggc aca ccc gca gct atc aat cca aat tat ttc atg ttt     1344
Ser Val Ala Gly Thr Pro Ala Ala Ile Asn Pro Asn Tyr Phe Met Phe
        435                 440                 445

gat tgg gat gtc aca tct caa atc gct acg gcc aag ttt att cgc tcc     1392
Asp Trp Asp Val Thr Ser Gln Ile Ala Thr Ala Lys Phe Ile Arg Ser
    450                 455                 460

att tat gcg gct tct cca ctg tcc tct ttc gtc gga tca gag acc aag     1440
Ile Tyr Ala Ala Ser Pro Leu Ser Ser Phe Val Gly Ser Glu Thr Lys
465                 470                 475                 480

cct gga ttg aac aaa gta tca gct aat gct acg gag gct gaa tgg ttt     1488
Pro Gly Leu Asn Lys Val Ser Ala Asn Ala Thr Glu Ala Glu Trp Phe
                485                 490                 495

gat tgg gtt aaa act gct tat cgc tca aac ttc cat cca gta tca acg     1536
Asp Trp Val Lys Thr Ala Tyr Arg Ser Asn Phe His Pro Val Ser Thr
            500                 505                 510

gct gca atg atg cca aga gag atc ggt gga gtg gta gac tca agg ttg     1584
Ala Ala Met Met Pro Arg Glu Ile Gly Gly Val Val Asp Ser Arg Leu
        515                 520                 525

aag gta tat gga aca gca aat gtg aga gtt gtg gat gct agt ata tta     1632
Lys Val Tyr Gly Thr Ala Asn Val Arg Val Val Asp Ala Ser Ile Leu
    530                 535                 540

cct atg cag gtt tct gga cat tta gtt agt act ttg tat gct gtg gca     1680
Pro Met Gln Val Ser Gly His Leu Val Ser Thr Leu Tyr Ala Val Ala
545                 550                 555                 560

gag aga gca gca gat ttg atc aag gag gac att tag                     1716
Glu Arg Ala Ala Asp Leu Ile Lys Glu Asp Ile
                565                 570


<210> SEQ ID NO 12
<211> LENGTH: 571
<212> TYPE: PRT
<213> ORGANISM: Botrytis tulipae

<400> SEQUENCE: 12

Ser Thr Leu Thr Tyr Asp Tyr Ile Val Ile Gly Ala Gly Thr Ser Gly
1               5                   10                  15

Leu Val Ile Ala Asn Arg Leu Ser Glu Leu Asn Val Thr Val Ala Val
            20                  25                  30

Ile Glu Ala Gly Asp Ser Gly Tyr Asn Asn Pro Asn Val Thr Asn Pro
        35                  40                  45

Ser Gly Tyr Gly Leu Ser Phe Gly Thr Asp Ile Asp Trp Ala Tyr Gln
    50                  55                  60

Ser Thr Asn Gln Lys Tyr Ala Gly Asn Thr Ser Gln Val Leu Arg Ala
65                  70                  75                  80
```

-continued

```
Gly Lys Ile Ile Gly Gly Thr Ser Thr Ile Asn Gly Met Ala Tyr Thr
                85                  90                  95

Arg Ala Glu Asp Val Gln Ile Asp Ala Trp Ala Ala Ile Gly Asn Asp
            100                 105                 110

Gly Trp Asn Trp Ala Asn Leu Phe Pro Tyr Tyr Lys Lys Ser Gln Thr
        115                 120                 125

Leu Glu Ile Pro Thr Thr Ala Gln Val Glu Ala Gly Ala Ala Tyr Asp
    130                 135                 140

Ala Ser Ala Asn Gly Phe Asp Gly Pro Leu Lys Val Gly Trp Leu Asn
145                 150                 155                 160

Ser Leu Glu Asp Thr Ser Asn Phe His Thr Thr Leu Asn Asp Thr Phe
                165                 170                 175

Ala Gly Leu Gly Val Pro Ser Asn Asp Asp Val Asn Thr Gly Arg Met
            180                 185                 190

Val Gly Tyr Ser Arg Tyr Pro Ala Thr Tyr Asp Arg Thr Leu Asn Val
        195                 200                 205

Arg His Asp Ala Gly Arg Ala Tyr Tyr Tyr Pro Ile Ala Asn Arg Thr
    210                 215                 220

Asn Leu His Leu Tyr Pro Asn Thr Met Ala Gln Arg Leu Thr Trp Thr
225                 230                 235                 240

Ser Asp Ala Asn Thr Pro Thr Ala Asn Gly Val Glu Val Leu Ser Asn
                245                 250                 255

Asn Ser Ser Ile Pro Tyr Thr Ile His Ala Asn Ser Glu Val Ile Leu
            260                 265                 270

Ser Ala Gly Ala Leu Ala Ser Pro Leu Leu Leu Glu Leu Ser Gly Ile
        275                 280                 285

Gly Asn Pro Ser Ile Leu Ser Lys His Asn Ile Ser Val Val Val Asp
    290                 295                 300

Leu Pro Thr Val Gly Glu Asn Leu Gln Asp Gln Thr Asn Thr Gly Leu
305                 310                 315                 320

Ala Tyr Asn Ser Ser Gly Asn Thr Ser Phe Ser Gly Ala Gly Thr Leu
                325                 330                 335

Val Ala Tyr Pro Ser Ala Ala Gln Leu Phe Gly Ser Glu Val Gln Lys
            340                 345                 350

Ile Ser Ala His Val Leu Gln Ser Leu Pro Ser Tyr Ala Ala Gln Val
        355                 360                 365

Ser Ala Ala Ser Gly Asn Ile Thr Lys Ala Ala Asp Leu Leu Lys Phe
    370                 375                 380

Phe Lys Ile Gln His Asp Leu Ile Phe Ser Thr Thr His Pro Val Pro
385                 390                 395                 400

Met Ala Glu Ile Leu Ile Ser Pro Ser Ala Thr Ala Phe Ser Ser Glu
                405                 410                 415

Tyr Trp Ala Leu Leu Pro Phe Ala Arg Gly Ser Ile His Ile Thr Ser
            420                 425                 430

Ser Val Ala Gly Thr Pro Ala Ala Ile Asn Pro Asn Tyr Phe Met Phe
        435                 440                 445

Asp Trp Asp Val Thr Ser Gln Ile Ala Thr Ala Lys Phe Ile Arg Ser
    450                 455                 460

Ile Tyr Ala Ala Ser Pro Leu Ser Ser Phe Val Gly Ser Glu Thr Lys
465                 470                 475                 480

Pro Gly Leu Asn Lys Val Ser Ala Asn Ala Thr Glu Ala Glu Trp Phe
                485                 490                 495

Asp Trp Val Lys Thr Ala Tyr Arg Ser Asn Phe His Pro Val Ser Thr
```

```
            500                 505                 510

Ala Ala Met Met Pro Arg Glu Ile Gly Gly Val Val Asp Ser Arg Leu
        515                 520                 525

Lys Val Tyr Gly Thr Ala Asn Val Arg Val Val Asp Ala Ser Ile Leu
    530                 535                 540

Pro Met Gln Val Ser Gly His Leu Val Ser Thr Leu Tyr Ala Val Ala
545                 550                 555                 560

Glu Arg Ala Ala Asp Leu Ile Lys Glu Asp Ile
                565                 570


<210> SEQ ID NO 13
<211> LENGTH: 1716
<212> TYPE: DNA
<213> ORGANISM: Ovulinia azaleae
<220> FEATURE:
<221> NAME/KEY: CDS
<222> LOCATION: (1)..(1716)

<400> SEQUENCE: 13

tct act tta act tat gat tat att gtt att ggt gct gga acc agt ggt       48
Ser Thr Leu Thr Tyr Asp Tyr Ile Val Ile Gly Ala Gly Thr Ser Gly
1               5                   10                  15

cta gtc atc gca aac cgt tta tcc gag tta aat gtc act gtg gct gtc       96
Leu Val Ile Ala Asn Arg Leu Ser Glu Leu Asn Val Thr Val Ala Val
            20                  25                  30

att gag gca ggt gat tcg ggt tac aac aat ccc aat gtg aca aac cca      144
Ile Glu Ala Gly Asp Ser Gly Tyr Asn Asn Pro Asn Val Thr Asn Pro
        35                  40                  45

tcc ggt tat gga cta tct ttt gga aca gac atc gat tgg gcg tat caa      192
Ser Gly Tyr Gly Leu Ser Phe Gly Thr Asp Ile Asp Trp Ala Tyr Gln
    50                  55                  60

tcg acc aac cag aag tat gca gga aac acg agc caa gtc tta cga gct      240
Ser Thr Asn Gln Lys Tyr Ala Gly Asn Thr Ser Gln Val Leu Arg Ala
65                  70                  75                  80

ggc aaa atc atc gga ggg act agt act atc aat gga atg gca tac acg      288
Gly Lys Ile Ile Gly Gly Thr Ser Thr Ile Asn Gly Met Ala Tyr Thr
                85                  90                  95

cga gcg gaa gat gtt caa att gat gct tgg gcg gcc att gga aat gat      336
Arg Ala Glu Asp Val Gln Ile Asp Ala Trp Ala Ala Ile Gly Asn Asp
            100                 105                 110

gga tgg aac tgg gca aat ctt ttc cca tac tac aaa aag tct cag aca      384
Gly Trp Asn Trp Ala Asn Leu Phe Pro Tyr Tyr Lys Lys Ser Gln Thr
        115                 120                 125

ctc gaa atc cct acc act gct caa gtt gaa gct ggt gca gca tat gac      432
Leu Glu Ile Pro Thr Thr Ala Gln Val Glu Ala Gly Ala Ala Tyr Asp
    130                 135                 140

gcc tca gcg aat gga ttc gat gga cca ctg aag gtt ggc tgg ctc aac      480
Ala Ser Ala Asn Gly Phe Asp Gly Pro Leu Lys Val Gly Trp Leu Asn
145                 150                 155                 160

agc ttg gaa gat act agc aac ttc cat aca acc ttg aat gat aca ttt      528
Ser Leu Glu Asp Thr Ser Asn Phe His Thr Thr Leu Asn Asp Thr Phe
                165                 170                 175

gca ggt ctt ggt gtt cct tca aat gat gat gtc aat act ggt aga atg      576
Ala Gly Leu Gly Val Pro Ser Asn Asp Asp Val Asn Thr Gly Arg Met
            180                 185                 190

gtt ggt tac agt cga tac cca gct act tac gac aga aca ttg aac gtt      624
Val Gly Tyr Ser Arg Tyr Pro Ala Thr Tyr Asp Arg Thr Leu Asn Val
        195                 200                 205

cgt cat gac gct gga cga gca tat tat tat cca att gcc aac cgc acc      672
Arg His Asp Ala Gly Arg Ala Tyr Tyr Tyr Pro Ile Ala Asn Arg Thr
```

-continued

```
    210                 215                 220

aat ctt cat ctt tac cca aat act atg gct caa cga ctc aca tgg aca      720
Asn Leu His Leu Tyr Pro Asn Thr Met Ala Gln Arg Leu Thr Trp Thr
225                 230                 235                 240

tcc gac gct aat acc cct acc gca aat gga gtc gaa gtt ctt tcc aac      768
Ser Asp Ala Asn Thr Pro Thr Ala Asn Gly Val Glu Val Leu Ser Asn
                245                 250                 255

aac tca agc att cca tac act att cat gca aac tcc gaa gtc att ctt      816
Asn Ser Ser Ile Pro Tyr Thr Ile His Ala Asn Ser Glu Val Ile Leu
            260                 265                 270

tca gct gga gct cta gca tct cct ctt ctt ctc gaa ctt tcc ggt att      864
Ser Ala Gly Ala Leu Ala Ser Pro Leu Leu Leu Glu Leu Ser Gly Ile
        275                 280                 285

gga aac cct tcc atc ttg agc agg cac aat atc tca gtt gta gtt gat      912
Gly Asn Pro Ser Ile Leu Ser Arg His Asn Ile Ser Val Val Val Asp
    290                 295                 300

ctc cca gct gta gga gaa aat ctt caa gat caa acg aat acc ggc ctt      960
Leu Pro Ala Val Gly Glu Asn Leu Gln Asp Gln Thr Asn Thr Gly Leu
305                 310                 315                 320

gca tac aac agt tca ggc aac acc tct ttc tct gga gct gga acc ttg     1008
Ala Tyr Asn Ser Ser Gly Asn Thr Ser Phe Ser Gly Ala Gly Thr Leu
                325                 330                 335

gta gct tat cct tcc gca gcc caa tta ttt ggt tct gaa gtt caa aaa     1056
Val Ala Tyr Pro Ser Ala Ala Gln Leu Phe Gly Ser Glu Val Gln Lys
            340                 345                 350

atc tct gct cat gtt ctt caa tct ctt cct tca tat gct gca caa gta     1104
Ile Ser Ala His Val Leu Gln Ser Leu Pro Ser Tyr Ala Ala Gln Val
        355                 360                 365

tca gct gca tca ggt aac atc acc aaa gct gca gat ttg ttg aaa ttc     1152
Ser Ala Ala Ser Gly Asn Ile Thr Lys Ala Ala Asp Leu Leu Lys Phe
    370                 375                 380

ttc aaa att caa cat gat ctg atc ttc tca act acc cac cca gtt cca     1200
Phe Lys Ile Gln His Asp Leu Ile Phe Ser Thr Thr His Pro Val Pro
385                 390                 395                 400

atg gct gaa ata ctc atc tca cca tct gca aca gct ttc agc tcg gaa     1248
Met Ala Glu Ile Leu Ile Ser Pro Ser Ala Thr Ala Phe Ser Ser Glu
                405                 410                 415

tat tgg gcc ttg tta cca ttt gca aga gga agt att cac atc aca tct     1296
Tyr Trp Ala Leu Leu Pro Phe Ala Arg Gly Ser Ile His Ile Thr Ser
            420                 425                 430

tcc gta gct ggc aca ccc gca gct atc aat cca aat tat ttc atg ttt     1344
Ser Val Ala Gly Thr Pro Ala Ala Ile Asn Pro Asn Tyr Phe Met Phe
        435                 440                 445

gat tgg gat gtc aca tct caa atc gct acg gcc aag ttt att cgc tcc     1392
Asp Trp Asp Val Thr Ser Gln Ile Ala Thr Ala Lys Phe Ile Arg Ser
    450                 455                 460

att tat gcg gct tct cca ctg tcc tct ttc gtc gga tca gag acc aag     1440
Ile Tyr Ala Ala Ser Pro Leu Ser Ser Phe Val Gly Ser Glu Thr Lys
465                 470                 475                 480

cct gga ttg aac aaa gta tca gct aat gct acg gag gct gaa tgg ttt     1488
Pro Gly Leu Asn Lys Val Ser Ala Asn Ala Thr Glu Ala Glu Trp Phe
                485                 490                 495

gat tgg gtt aaa act gct tat cgc tca aac ttc cat cca gta tca acg     1536
Asp Trp Val Lys Thr Ala Tyr Arg Ser Asn Phe His Pro Val Ser Thr
            500                 505                 510

gct gca atg atg cca aga gag atc ggt gga gtg gta gac tca agg ttg     1584
Ala Ala Met Met Pro Arg Glu Ile Gly Gly Val Val Asp Ser Arg Leu
        515                 520                 525

aag gta tat gga aca gca aat gtg aga gtt gtg gat gct agt ata tta     1632
```

```
Lys Val Tyr Gly Thr Ala Asn Val Arg Val Val Asp Ala Ser Ile Leu
    530                 535                 540

cct atg cag gtt tct gga cat tta gtt agt act ttg tat gct gtg gca     1680
Pro Met Gln Val Ser Gly His Leu Val Ser Thr Leu Tyr Ala Val Ala
545                 550                 555                 560

gag aga gca gca gat ttg atc aag gaa gac atg tag                     1716
Glu Arg Ala Ala Asp Leu Ile Lys Glu Asp Met
                565                 570


<210> SEQ ID NO 14
<211> LENGTH: 571
<212> TYPE: PRT
<213> ORGANISM: Ovulinia azaleae

<400> SEQUENCE: 14

Ser Thr Leu Thr Tyr Asp Tyr Ile Val Ile Gly Ala Gly Thr Ser Gly
1               5                   10                  15

Leu Val Ile Ala Asn Arg Leu Ser Glu Leu Asn Val Thr Val Ala Val
            20                  25                  30

Ile Glu Ala Gly Asp Ser Gly Tyr Asn Asn Pro Asn Val Thr Asn Pro
        35                  40                  45

Ser Gly Tyr Gly Leu Ser Phe Gly Thr Asp Ile Asp Trp Ala Tyr Gln
    50                  55                  60

Ser Thr Asn Gln Lys Tyr Ala Gly Asn Thr Ser Gln Val Leu Arg Ala
65                  70                  75                  80

Gly Lys Ile Ile Gly Gly Thr Ser Thr Ile Asn Gly Met Ala Tyr Thr
                85                  90                  95

Arg Ala Glu Asp Val Gln Ile Asp Ala Trp Ala Ala Ile Gly Asn Asp
            100                 105                 110

Gly Trp Asn Trp Ala Asn Leu Phe Pro Tyr Tyr Lys Lys Ser Gln Thr
        115                 120                 125

Leu Glu Ile Pro Thr Thr Ala Gln Val Glu Ala Gly Ala Ala Tyr Asp
    130                 135                 140

Ala Ser Ala Asn Gly Phe Asp Gly Pro Leu Lys Val Gly Trp Leu Asn
145                 150                 155                 160

Ser Leu Glu Asp Thr Ser Asn Phe His Thr Thr Leu Asn Asp Thr Phe
                165                 170                 175

Ala Gly Leu Gly Val Pro Ser Asn Asp Asp Val Asn Thr Gly Arg Met
            180                 185                 190

Val Gly Tyr Ser Arg Tyr Pro Ala Thr Tyr Asp Arg Thr Leu Asn Val
        195                 200                 205

Arg His Asp Ala Gly Arg Ala Tyr Tyr Tyr Pro Ile Ala Asn Arg Thr
    210                 215                 220

Asn Leu His Leu Tyr Pro Asn Thr Met Ala Gln Arg Leu Thr Trp Thr
225                 230                 235                 240

Ser Asp Ala Asn Thr Pro Thr Ala Asn Gly Val Glu Val Leu Ser Asn
                245                 250                 255

Asn Ser Ser Ile Pro Tyr Thr Ile His Ala Asn Ser Glu Val Ile Leu
            260                 265                 270

Ser Ala Gly Ala Leu Ala Ser Pro Leu Leu Leu Glu Leu Ser Gly Ile
        275                 280                 285

Gly Asn Pro Ser Ile Leu Ser Arg His Asn Ile Ser Val Val Val Asp
    290                 295                 300

Leu Pro Ala Val Gly Glu Asn Leu Gln Asp Gln Thr Asn Thr Gly Leu
305                 310                 315                 320
```

-continued

```
Ala Tyr Asn Ser Ser Gly Asn Thr Ser Phe Ser Gly Ala Gly Thr Leu
                325                 330                 335

Val Ala Tyr Pro Ser Ala Ala Gln Leu Phe Gly Ser Glu Val Gln Lys
            340                 345                 350

Ile Ser Ala His Val Leu Gln Ser Leu Pro Ser Tyr Ala Ala Gln Val
        355                 360                 365

Ser Ala Ala Ser Gly Asn Ile Thr Lys Ala Ala Asp Leu Leu Lys Phe
    370                 375                 380

Phe Lys Ile Gln His Asp Leu Ile Phe Ser Thr Thr His Pro Val Pro
385                 390                 395                 400

Met Ala Glu Ile Leu Ile Ser Pro Ser Ala Thr Ala Phe Ser Ser Glu
                405                 410                 415

Tyr Trp Ala Leu Leu Pro Phe Ala Arg Gly Ser Ile His Ile Thr Ser
            420                 425                 430

Ser Val Ala Gly Thr Pro Ala Ala Ile Asn Pro Asn Tyr Phe Met Phe
        435                 440                 445

Asp Trp Asp Val Thr Ser Gln Ile Ala Thr Ala Lys Phe Ile Arg Ser
    450                 455                 460

Ile Tyr Ala Ala Ser Pro Leu Ser Ser Phe Val Gly Ser Glu Thr Lys
465                 470                 475                 480

Pro Gly Leu Asn Lys Val Ser Ala Asn Ala Thr Glu Ala Glu Trp Phe
                485                 490                 495

Asp Trp Val Lys Thr Ala Tyr Arg Ser Asn Phe His Pro Val Ser Thr
            500                 505                 510

Ala Ala Met Met Pro Arg Glu Ile Gly Gly Val Val Asp Ser Arg Leu
        515                 520                 525

Lys Val Tyr Gly Thr Ala Asn Val Arg Val Val Asp Ala Ser Ile Leu
    530                 535                 540

Pro Met Gln Val Ser Gly His Leu Val Ser Thr Leu Tyr Ala Val Ala
545                 550                 555                 560

Glu Arg Ala Ala Asp Leu Ile Lys Glu Asp Met
                565                 570


<210> SEQ ID NO 15
<211> LENGTH: 1719
<212> TYPE: DNA
<213> ORGANISM: Ciborinia camelliae
<220> FEATURE:
<221> NAME/KEY: CDS
<222> LOCATION: (1)..(1719)

<400> SEQUENCE: 15

gtt gcc tta acc tac gat tat gtt atc gtt ggt gct gga aca agt ggt        48
Val Ala Leu Thr Tyr Asp Tyr Val Ile Val Gly Ala Gly Thr Ser Gly
1               5                   10                  15

ctc gtc act gca cac cgt ctg tcc gag ttg gct gat gtc act gtc gcc        96
Leu Val Thr Ala His Arg Leu Ser Glu Leu Ala Asp Val Thr Val Ala
            20                  25                  30

gtg att gaa gct ggt gaa tcg aac tac aac aac gcc aat gtc acc aac       144
Val Ile Glu Ala Gly Glu Ser Asn Tyr Asn Asn Ala Asn Val Thr Asn
        35                  40                  45

cct gca ggc tat gga ttg gct ttt ggt acc caa att gat tgg caa tac       192
Pro Ala Gly Tyr Gly Leu Ala Phe Gly Thr Gln Ile Asp Trp Gln Tyr
    50                  55                  60

caa aca acc gtc caa gag tac gga gga gac gtc acc aag gtt atc cga       240
Gln Thr Thr Val Gln Glu Tyr Gly Gly Asp Val Thr Lys Val Ile Arg
65                  70                  75                  80
```

```
gct ggt aaa tcc atc gga gga act agc aca atc aac gga atg gct tac      288
Ala Gly Lys Ser Ile Gly Gly Thr Ser Thr Ile Asn Gly Met Ala Tyr
                85                  90                  95

acc cga gct gag gat gtt cag gtt gat gca tgg gaa gcc ctt gga aat      336
Thr Arg Ala Glu Asp Val Gln Val Asp Ala Trp Glu Ala Leu Gly Asn
            100                 105                 110

gag gga tgg aac tgg gca aac atg ctc cca tac tac aag aag tct caa      384
Glu Gly Trp Asn Trp Ala Asn Met Leu Pro Tyr Tyr Lys Lys Ser Gln
        115                 120                 125

aca ctt cag gtt cca act gag gcc caa gct gca cta gga gca cat tac      432
Thr Leu Gln Val Pro Thr Glu Ala Gln Ala Ala Leu Gly Ala His Tyr
    130                 135                 140

gac cct gcg tca aac gga tat gaa gga cca ttg aag gtt ggt tgg gtc      480
Asp Pro Ala Ser Asn Gly Tyr Glu Gly Pro Leu Lys Val Gly Trp Val
145                 150                 155                 160

aac gcc atg gcc acc gat gac ttc cac aca att ttg aac gag acc tac      528
Asn Ala Met Ala Thr Asp Asp Phe His Thr Ile Leu Asn Glu Thr Tyr
                165                 170                 175

gct gct ctc gac gtt ccc gcc aac aac gat gtc aac act ggt aag atg      576
Ala Ala Leu Asp Val Pro Ala Asn Asn Asp Val Asn Thr Gly Lys Met
            180                 185                 190

atc ggt tac acc aga tac cca gct acc tac gac aga acc ttg aac atg      624
Ile Gly Tyr Thr Arg Tyr Pro Ala Thr Tyr Asp Arg Thr Leu Asn Met
        195                 200                 205

cgt tgt gat gcc gga aga gcc tac tac tac cca atc cag aac cgt acc      672
Arg Cys Asp Ala Gly Arg Ala Tyr Tyr Tyr Pro Ile Gln Asn Arg Thr
    210                 215                 220

aac ctt cat ctt tac cca aac acc atg gcc cag cgt ctt aca tgg aaa      720
Asn Leu His Leu Tyr Pro Asn Thr Met Ala Gln Arg Leu Thr Trp Lys
225                 230                 235                 240

tcc ggt gcc tcc acc ccc act gca gag gga gtt gag gtt ctt gcc gac      768
Ser Gly Ala Ser Thr Pro Thr Ala Glu Gly Val Glu Val Leu Ala Asp
                245                 250                 255

ggc gag acc acc cca tac acc att cac gca agc tcc gaa gtc atc atc      816
Gly Glu Thr Thr Pro Tyr Thr Ile His Ala Ser Ser Glu Val Ile Ile
            260                 265                 270

tcc gcc ggt gct ctt ggt tcc cct ctt gtt ctc gag cac tct ggt att      864
Ser Ala Gly Ala Leu Gly Ser Pro Leu Val Leu Glu His Ser Gly Ile
        275                 280                 285

ggt aac cct gct atc ctt gag aag tac aac att tcc gtc gtc gtt gat      912
Gly Asn Pro Ala Ile Leu Glu Lys Tyr Asn Ile Ser Val Val Val Asp
    290                 295                 300

ctc cca acc gtc gga gag aat ctt cag gat caa aca aac acc gct ctt      960
Leu Pro Thr Val Gly Glu Asn Leu Gln Asp Gln Thr Asn Thr Ala Leu
305                 310                 315                 320

ggt ttc gac acc tca agc gac aat gtc act tac tca gcc gtt tct acc     1008
Gly Phe Asp Thr Ser Ser Asp Asn Val Thr Tyr Ser Ala Val Ser Thr
                325                 330                 335

tac ctc ggt tac cca tct gct gct cag atg ttc ggt tcc gat ttc aag     1056
Tyr Leu Gly Tyr Pro Ser Ala Ala Gln Met Phe Gly Ser Asp Phe Lys
            340                 345                 350

acc gtc gcc gct gaa att ctc gct gct ctt cct tcc tat gcc gac aag     1104
Thr Val Ala Ala Glu Ile Leu Ala Ala Leu Pro Ser Tyr Ala Asp Lys
        355                 360                 365

gtc gcc att gca tca ggc aat gtt acc aag gcc gct gat ttg ttg aag     1152
Val Ala Ile Ala Ser Gly Asn Val Thr Lys Ala Ala Asp Leu Leu Lys
    370                 375                 380

ttc ttc aag att caa tac gag ctc atc ttc agc gcc acc agc cct gtc     1200
Phe Phe Lys Ile Gln Tyr Glu Leu Ile Phe Ser Ala Thr Ser Pro Val
385                 390                 395                 400
```

```
cct gtc gcc gag ctt ctc gtt acc cca gtt gga acc acc tac agt gcc      1248
Pro Val Ala Glu Leu Leu Val Thr Pro Val Gly Thr Thr Tyr Ser Ala
                405                 410                 415

gag ttc tgg tcc ttg ttg cca ttc tcc cgt gga aac atc cac atc tca      1296
Glu Phe Trp Ser Leu Leu Pro Phe Ser Arg Gly Asn Ile His Ile Ser
            420                 425                 430

tct gcc acc cca ggt gtc gcc gca acc atc aac cca aac tac ttc atg      1344
Ser Ala Thr Pro Gly Val Ala Ala Thr Ile Asn Pro Asn Tyr Phe Met
        435                 440                 445

ctt gat tat gat atg atc tcg caa gtc cgc tcc gcc aag tac att cgt      1392
Leu Asp Tyr Asp Met Ile Ser Gln Val Arg Ser Ala Lys Tyr Ile Arg
    450                 455                 460

gag atc ttt gcc acc act cca ttg tcc cct ctc gtt ggc agc gaa acc      1440
Glu Ile Phe Ala Thr Thr Pro Leu Ser Pro Leu Val Gly Ser Glu Thr
465                 470                 475                 480

acc cct ggt ttg gac tct att gcc tca gct gcc acc gag gcc gaa tgg      1488
Thr Pro Gly Leu Asp Ser Ile Ala Ser Ala Ala Thr Glu Ala Glu Trp
                485                 490                 495

gcc gct tgg gtc aag acc gcc tac cga tcc aac ttc cac ccc gtc gcc      1536
Ala Ala Trp Val Lys Thr Ala Tyr Arg Ser Asn Phe His Pro Val Ala
            500                 505                 510

acc gct gcc atg atg cca cgc gag atc gga gga gtc gtc gac tcc cgc      1584
Thr Ala Ala Met Met Pro Arg Glu Ile Gly Gly Val Val Asp Ser Arg
        515                 520                 525

ttg aag gtc tac gga acc acc aac gtc aga gtc gtc gat gcc agt atc      1632
Leu Lys Val Tyr Gly Thr Thr Asn Val Arg Val Val Asp Ala Ser Ile
    530                 535                 540

ttg ccc atg caa gtt tgc gga cat ttg acc agt act ttg tac gcc atg      1680
Leu Pro Met Gln Val Cys Gly His Leu Thr Ser Thr Leu Tyr Ala Met
545                 550                 555                 560

tcc gag aga gcc gct gac ttg atc aag gaa gat atg taa                  1719
Ser Glu Arg Ala Ala Asp Leu Ile Lys Glu Asp Met
                565                 570


<210> SEQ ID NO 16
<211> LENGTH: 572
<212> TYPE: PRT
<213> ORGANISM: Ciborinia camelliae

<400> SEQUENCE: 16

Val Ala Leu Thr Tyr Asp Tyr Val Ile Val Gly Ala Gly Thr Ser Gly
1               5                   10                  15

Leu Val Thr Ala His Arg Leu Ser Glu Leu Ala Asp Val Thr Val Ala
            20                  25                  30

Val Ile Glu Ala Gly Glu Ser Asn Tyr Asn Asn Ala Asn Val Thr Asn
        35                  40                  45

Pro Ala Gly Tyr Gly Leu Ala Phe Gly Thr Gln Ile Asp Trp Gln Tyr
    50                  55                  60

Gln Thr Thr Val Gln Glu Tyr Gly Gly Asp Val Thr Lys Val Ile Arg
65                  70                  75                  80

Ala Gly Lys Ser Ile Gly Gly Thr Ser Thr Ile Asn Gly Met Ala Tyr
                85                  90                  95

Thr Arg Ala Glu Asp Val Gln Val Asp Ala Trp Glu Ala Leu Gly Asn
            100                 105                 110

Glu Gly Trp Asn Trp Ala Asn Met Leu Pro Tyr Tyr Lys Lys Ser Gln
        115                 120                 125

Thr Leu Gln Val Pro Thr Glu Ala Gln Ala Ala Leu Gly Ala His Tyr
    130                 135                 140
```

-continued

```
Asp Pro Ala Ser Asn Gly Tyr Glu Gly Pro Leu Lys Val Gly Trp Val
145                 150                 155                 160

Asn Ala Met Ala Thr Asp Asp Phe His Thr Ile Leu Asn Glu Thr Tyr
                165                 170                 175

Ala Ala Leu Asp Val Pro Ala Asn Asn Asp Val Asn Thr Gly Lys Met
            180                 185                 190

Ile Gly Tyr Thr Arg Tyr Pro Ala Thr Tyr Asp Arg Thr Leu Asn Met
        195                 200                 205

Arg Cys Asp Ala Gly Arg Ala Tyr Tyr Tyr Pro Ile Gln Asn Arg Thr
    210                 215                 220

Asn Leu His Leu Tyr Pro Asn Thr Met Ala Gln Arg Leu Thr Trp Lys
225                 230                 235                 240

Ser Gly Ala Ser Thr Pro Thr Ala Glu Gly Val Glu Val Leu Ala Asp
                245                 250                 255

Gly Glu Thr Thr Pro Tyr Thr Ile His Ala Ser Ser Glu Val Ile Ile
            260                 265                 270

Ser Ala Gly Ala Leu Gly Ser Pro Leu Val Leu Glu His Ser Gly Ile
        275                 280                 285

Gly Asn Pro Ala Ile Leu Glu Lys Tyr Asn Ile Ser Val Val Val Asp
    290                 295                 300

Leu Pro Thr Val Gly Glu Asn Leu Gln Asp Gln Thr Asn Thr Ala Leu
305                 310                 315                 320

Gly Phe Asp Thr Ser Ser Asp Asn Val Thr Tyr Ser Ala Val Ser Thr
                325                 330                 335

Tyr Leu Gly Tyr Pro Ser Ala Ala Gln Met Phe Gly Ser Asp Phe Lys
            340                 345                 350

Thr Val Ala Ala Glu Ile Leu Ala Ala Leu Pro Ser Tyr Ala Asp Lys
        355                 360                 365

Val Ala Ile Ala Ser Gly Asn Val Thr Lys Ala Ala Asp Leu Leu Lys
    370                 375                 380

Phe Phe Lys Ile Gln Tyr Glu Leu Ile Phe Ser Ala Thr Ser Pro Val
385                 390                 395                 400

Pro Val Ala Glu Leu Leu Val Thr Pro Val Gly Thr Thr Tyr Ser Ala
                405                 410                 415

Glu Phe Trp Ser Leu Leu Pro Phe Ser Arg Gly Asn Ile His Ile Ser
            420                 425                 430

Ser Ala Thr Pro Gly Val Ala Ala Thr Ile Asn Pro Asn Tyr Phe Met
        435                 440                 445

Leu Asp Tyr Asp Met Ile Ser Gln Val Arg Ser Ala Lys Tyr Ile Arg
    450                 455                 460

Glu Ile Phe Ala Thr Thr Pro Leu Ser Pro Leu Val Gly Ser Glu Thr
465                 470                 475                 480

Thr Pro Gly Leu Asp Ser Ile Ala Ser Ala Ala Thr Glu Ala Glu Trp
                485                 490                 495

Ala Ala Trp Val Lys Thr Ala Tyr Arg Ser Asn Phe His Pro Val Ala
            500                 505                 510

Thr Ala Ala Met Met Pro Arg Glu Ile Gly Gly Val Val Asp Ser Arg
        515                 520                 525

Leu Lys Val Tyr Gly Thr Thr Asn Val Arg Val Val Asp Ala Ser Ile
    530                 535                 540

Leu Pro Met Gln Val Cys Gly His Leu Thr Ser Thr Leu Tyr Ala Met
545                 550                 555                 560
```

Ser Glu Arg Ala Ala Asp Leu Ile Lys Glu Asp Met
565 570

<210> SEQ ID NO 17
<211> LENGTH: 38
<212> TYPE: DNA
<213> ORGANISM: Artificial Sequence
<220> FEATURE:
<223> OTHER INFORMATION: Synthetic primer

<400> SEQUENCE: 17
ggaaccagtg gtctagtcat cgcaaaycgk ytatcyga 38

<210> SEQ ID NO 18
<211> LENGTH: 38
<212> TYPE: DNA
<213> ORGANISM: Artificial Sequence
<220> FEATURE:
<223> OTHER INFORMATION: Synthetic primer

<400> SEQUENCE: 18
tggatacttc ctcttgcaaa tggtaryarr gcccaata 38

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
gatcgccgca ggggtgcctg gtatcg 26

<210> SEQ ID NO 20
<211> LENGTH: 28
<212> TYPE: DNA
<213> ORGANISM: Artificial Sequence
<220> FEATURE:
<223> OTHER INFORMATION: Synthetic primer

<400> SEQUENCE: 20
ggtgccgatg tccctactgc aaatggag 28

<210> SEQ ID NO 21
<211> LENGTH: 39
<212> TYPE: DNA
<213> ORGANISM: Artificial Sequence
<220> FEATURE:
<223> OTHER INFORMATION: Synthetic primer

<400> SEQUENCE: 21
ggcagatcta gtcctgacct tagtctaact tatgactat 39

<210> SEQ ID NO 22
<211> LENGTH: 48
<212> TYPE: DNA
<213> ORGANISM: Artificial Sequence
<220> FEATURE:
<223> OTHER INFORMATION: Synthetic primer

<400> SEQUENCE: 22
ctgcaggtcg acgcatgctt aaatatcctc cttgatcaaa tctgccgc 48

<210> SEQ ID NO 23
<211> LENGTH: 46
<212> TYPE: DNA

<213> ORGANISM: Artificial Sequence
<220> FEATURE:
<223> OTHER INFORMATION: Synthetic primer

<400> SEQUENCE: 23
acatgcatgc tctagattaa atatcctcct tgatcaaatc tgccgc 46

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
cgttcgtcat gacgctggac gagc 24

<210> SEQ ID NO 25
<211> LENGTH: 34
<212> TYPE: DNA
<213> ORGANISM: Artificial Sequence
<220> FEATURE:
<223> OTHER INFORMATION: Synthetic primer

<400> SEQUENCE: 25
gaagatctat gtatcgttta ctctctacat ttgc 34

<210> SEQ ID NO 26
<211> LENGTH: 34
<212> TYPE: DNA
<213> ORGANISM: Artificial Sequence
<220> FEATURE:
<223> OTHER INFORMATION: Synthetic primer

<400> SEQUENCE: 26
gctctagact aaatgtcctc cttgatcaaa tctg 34

<210> SEQ ID NO 27
<211> LENGTH: 33
<212> TYPE: DNA
<213> ORGANISM: Artificial Sequence
<220> FEATURE:
<223> OTHER INFORMATION: Synthetic primer

<400> SEQUENCE: 27
gaagatctag caccgactct actttaactt atg 33

<210> SEQ ID NO 28
<211> LENGTH: 35
<212> TYPE: DNA
<213> ORGANISM: Artificial Sequence
<220> FEATURE:
<223> OTHER INFORMATION: Synthetic primer

<400> SEQUENCE: 28
gctctagact acatgtcttc cttgatcaaa tctgc 35

<210> SEQ ID NO 29
<211> LENGTH: 27
<212> TYPE: DNA
<213> ORGANISM: Artificial Sequence
<220> FEATURE:
<223> OTHER INFORMATION: Synthetic primer

<400> SEQUENCE: 29
cacatggaca tccgacgcta atacccc 27

<210> SEQ ID NO 30
<211> LENGTH: 26
<212> TYPE: DNA
<213> ORGANISM: Artificial Sequence
<220> FEATURE:
<223> OTHER INFORMATION: Synthetic primer

<400> SEQUENCE: 30
atgtatcgtt tactctctac atttgc 26

<210> SEQ ID NO 31
<211> LENGTH: 26
<212> TYPE: DNA
<213> ORGANISM: Artificial Sequence
<220> FEATURE:
<223> OTHER INFORMATION: Synthetic primer

<400> SEQUENCE: 31
ctacatgtct tccttgatca aatctg 26

<210> SEQ ID NO 32
<211> LENGTH: 33
<212> TYPE: DNA
<213> ORGANISM: Artificial Sequence
<220> FEATURE:
<223> OTHER INFORMATION: Synthetic primer

<400> SEQUENCE: 32
gaagatctag caccgactct actttaactt atg 33

<210> SEQ ID NO 33
<211> LENGTH: 34
<212> TYPE: DNA
<213> ORGANISM: Artificial Sequence
<220> FEATURE:
<223> OTHER INFORMATION: Synthetic primer

<400> SEQUENCE: 33
gctctagact acatgtcttc cttgatcaaa tctg 34

<210> SEQ ID NO 34
<211> LENGTH: 50
<212> TYPE: DNA
<213> ORGANISM: Artificial Sequence
<220> FEATURE:
<223> OTHER INFORMATION: Synthetic primer

<400> SEQUENCE: 34
tgaccaattc cgcagctcgt caaaatgaat catttacttc ctgcttttgc 50

<210> SEQ ID NO 35
<211> LENGTH: 44
<212> TYPE: DNA
<213> ORGANISM: Artificial Sequence
<220> FEATURE:
<223> OTHER INFORMATION: Synthetic primer

<400> SEQUENCE: 35
cgcttctaga gcatgcttaa atatcctcct tgatcaaatc tgcc 44

<210> SEQ ID NO 36
<211> LENGTH: 54
<212> TYPE: DNA
<213> ORGANISM: Artificial Sequence
<220> FEATURE:

<223> OTHER INFORMATION: Synthetic primer

<400> SEQUENCE: 36
ccctgtccct ggcagtggcg gcacctttga gtcctgacct tagtctaact tatg 54

<210> SEQ ID NO 37
<211> LENGTH: 57
<212> TYPE: DNA
<213> ORGANISM: Artificial Sequence
<220> FEATURE:
<223> OTHER INFORMATION: Synthetic primer

<400> SEQUENCE: 37
atgttgggaa agctctcctt cctcagtgcc ctgtccctgg cagtggcggc acctttg 57

<210> SEQ ID NO 38
<211> LENGTH: 49
<212> TYPE: DNA
<213> ORGANISM: Artificial Sequence
<220> FEATURE:
<223> OTHER INFORMATION: Synthetic primer

<400> SEQUENCE: 38
tgaccaattc cgcagctcgt caaaatgttg ggaaagctct ccttcctca 49

<210> SEQ ID NO 39
<211> LENGTH: 45
<212> TYPE: DNA
<213> ORGANISM: Artificial Sequence
<220> FEATURE:
<223> OTHER INFORMATION: Synthetic primer

<400> SEQUENCE: 39
ccgtcctcca agttagtcga ctgaccaatt ccgcagctcg tcaaa 45

<210> SEQ ID NO 40
<211> LENGTH: 50
<212> TYPE: DNA
<213> ORGANISM: Artificial Sequence
<220> FEATURE:
<223> OTHER INFORMATION: Synthetic primer

<400> SEQUENCE: 40
tgaccaattc cgcagctcgt caaaatgtat cgtttactct ctacatttgc 50

<210> SEQ ID NO 41
<211> LENGTH: 43
<212> TYPE: DNA
<213> ORGANISM: Artificial Sequence
<220> FEATURE:
<223> OTHER INFORMATION: Synthetic primer

<400> SEQUENCE: 41
cgcttctaga gcatgcctaa atgtcctcct tgatcaaatc tgc 43

<210> SEQ ID NO 42
<211> LENGTH: 54
<212> TYPE: DNA
<213> ORGANISM: Artificial Sequence
<220> FEATURE:
<223> OTHER INFORMATION: Synthetic primer

<400> SEQUENCE: 42
ccctgtccct ggcagtggcg gcacctttga gcaccgactc tactttaact tatg 54

<210> SEQ ID NO 43
<211> LENGTH: 30
<212> TYPE: DNA
<213> ORGANISM: Artificial Sequence
<220> FEATURE:
<223> OTHER INFORMATION: Synthetic primer

<400> SEQUENCE: 43
acggaaatgt tgtacttctc aaggatagca 30

<210> SEQ ID NO 44
<211> LENGTH: 30
<212> TYPE: DNA
<213> ORGANISM: Artificial Sequence
<220> FEATURE:
<223> OTHER INFORMATION: Synthetic primer

<400> SEQUENCE: 44
cgtcgttgat ctcccaaccg tcggagagaa 30

<210> SEQ ID NO 45
<211> LENGTH: 36
<212> TYPE: DNA
<213> ORGANISM: Artificial Sequence
<220> FEATURE:
<223> OTHER INFORMATION: Synthetic primer

<400> SEQUENCE: 45
ccgcagctcg tcaaaatgca tcgcttcctt cctgcc 36

<210> SEQ ID NO 46
<211> LENGTH: 45
<212> TYPE: DNA
<213> ORGANISM: Artificial Sequence
<220> FEATURE:
<223> OTHER INFORMATION: Synthetic primer

<400> SEQUENCE: 46
gttacgcttc tagagcatgc gttcatttac atatcttcct tgatc 45

<210> SEQ ID NO 47
<211> LENGTH: 36
<212> TYPE: DNA
<213> ORGANISM: Artificial Sequence
<220> FEATURE:
<223> OTHER INFORMATION: Synthetic primer

<400> SEQUENCE: 47
gtggcggcac ctttggttgc cttaacctac gattat 36

<210> SEQ ID NO 48
<211> LENGTH: 1779
<212> TYPE: DNA
<213> ORGANISM: Artificial Sequence
<220> FEATURE:
<223> OTHER INFORMATION: DuGLD-Atsig gene
<220> FEATURE:
<221> NAME/KEY: sig_peptide
<222> LOCATION: (1)..(66)
<220> FEATURE:
<221> NAME/KEY: sig_peptide
<222> LOCATION: (1)..(57)
<223> OTHER INFORMATION: A_terreus_signal_peptide
<220> FEATURE:
<221> NAME/KEY: CDS
<222> LOCATION: (1)..(1779)
<220> FEATURE:
<221> NAME/KEY: sig_peptide
<222> LOCATION: (58)..(66)

```
<223> OTHER INFORMATION: D_tuberosa_signal_peptide

<400> SEQUENCE: 48

atg ttg gga aag ctc tcc ttc ctc agt gcc ctg tcc ctg gca gtg gcg       48
Met Leu Gly Lys Leu Ser Phe Leu Ser Ala Leu Ser Leu Ala Val Ala
1               5                   10                  15

gca cct ttg agt cct gac ctt agt cta act tat gac tat gtt att gtt       96
Ala Pro Leu Ser Pro Asp Leu Ser Leu Thr Tyr Asp Tyr Val Ile Val
            20                  25                  30

ggt gct gga aca agt ggt tta gtc att gca aac cgt cta tcc gag ttg      144
Gly Ala Gly Thr Ser Gly Leu Val Ile Ala Asn Arg Leu Ser Glu Leu
        35                  40                  45

aat gtc act gtg gcc gtg att gaa gca ggt gat tca ggc tac aac aat      192
Asn Val Thr Val Ala Val Ile Glu Ala Gly Asp Ser Gly Tyr Asn Asn
    50                  55                  60

gtc aat gtg act aac ccg gcc ggt tat gga ttg gct ttt gga acc gac      240
Val Asn Val Thr Asn Pro Ala Gly Tyr Gly Leu Ala Phe Gly Thr Asp
65                  70                  75                  80

atc gat tgg gca tac caa tca acc aat cag aag tat gca ggg aac gct      288
Ile Asp Trp Ala Tyr Gln Ser Thr Asn Gln Lys Tyr Ala Gly Asn Ala
                85                  90                  95

acg cag act tta cga gct ggg aaa gtc ata gga ggt act agc acg atc      336
Thr Gln Thr Leu Arg Ala Gly Lys Val Ile Gly Gly Thr Ser Thr Ile
            100                 105                 110

aat ggg atg gca tac acc cga gct gaa gat gtt cag att gat gct tgg      384
Asn Gly Met Ala Tyr Thr Arg Ala Glu Asp Val Gln Ile Asp Ala Trp
        115                 120                 125

gca gcc ctt gga aat gat gga tgg aat tgg gag aat tta ttc cca tac      432
Ala Ala Leu Gly Asn Asp Gly Trp Asn Trp Glu Asn Leu Phe Pro Tyr
    130                 135                 140

tac aag aag tct cag aca ctt caa gct cct acc gct gct caa gct gaa      480
Tyr Lys Lys Ser Gln Thr Leu Gln Ala Pro Thr Ala Ala Gln Ala Glu
145                 150                 155                 160

gcc ggt gct aca tac gat cct tcg gca aat gga ttc gat ggg cca ttg      528
Ala Gly Ala Thr Tyr Asp Pro Ser Ala Asn Gly Phe Asp Gly Pro Leu
                165                 170                 175

aag gtt ggc tgg ctc aaa agc ttg gcc aat gat gac ttt cac ata att      576
Lys Val Gly Trp Leu Lys Ser Leu Ala Asn Asp Asp Phe His Ile Ile
            180                 185                 190

ctg aac gat acc tac gct tct ctc ggc att ttt gcg aat gag gat gtc      624
Leu Asn Asp Thr Tyr Ala Ser Leu Gly Ile Phe Ala Asn Glu Asp Val
        195                 200                 205

aac act ggt aga atg gtt ggt tat aat cgc tac cca gtt acc tac gac      672
Asn Thr Gly Arg Met Val Gly Tyr Asn Arg Tyr Pro Val Thr Tyr Asp
    210                 215                 220

gaa acc ttg aac gtt cgt cat gat gcc ggg cga gca tac tat tat cca      720
Glu Thr Leu Asn Val Arg His Asp Ala Gly Arg Ala Tyr Tyr Tyr Pro
225                 230                 235                 240

att gca aac cgc acc aac ctt cat ctt tac cca aat acc atg gct caa      768
Ile Ala Asn Arg Thr Asn Leu His Leu Tyr Pro Asn Thr Met Ala Gln
                245                 250                 255

cgg ctt act tgg aaa tct ggt gcc gat gtc cct act gca aat gga gtt      816
Arg Leu Thr Trp Lys Ser Gly Ala Asp Val Pro Thr Ala Asn Gly Val
            260                 265                 270

gag gta ctt acc aac aat tca agc atc cca tac acc att tct gca aat      864
Glu Val Leu Thr Asn Asn Ser Ser Ile Pro Tyr Thr Ile Ser Ala Asn
        275                 280                 285

tca gaa gtc att ctt tca gct gga gct ctg gcg tcc cct cta ctt ctc      912
Ser Glu Val Ile Leu Ser Ala Gly Ala Leu Ala Ser Pro Leu Leu Leu
    290                 295                 300
```

```
gaa ctt tct ggc atc gga aat cct tcc ctt tta aac aag tac aac att      960
Glu Leu Ser Gly Ile Gly Asn Pro Ser Leu Leu Asn Lys Tyr Asn Ile
305                 310                 315                 320

ccg gtc gtg gtt gat ctt cca acc gtc gga gaa aat ctt cag gat caa     1008
Pro Val Val Val Asp Leu Pro Thr Val Gly Glu Asn Leu Gln Asp Gln
                325                 330                 335

acg aac aat ggt ctt gca tac aca gtt tca aag gac gcc tcc ttc tct     1056
Thr Asn Asn Gly Leu Ala Tyr Thr Val Ser Lys Asp Ala Ser Phe Ser
            340                 345                 350

ggg gtc ggt acc ttg gtc act tat cct tca gcg gct caa gtt ttt ggt     1104
Gly Val Gly Thr Leu Val Thr Tyr Pro Ser Ala Ala Gln Val Phe Gly
        355                 360                 365

tct gaa atc caa aac atc tcc gct cat gtt ctt gat tct ctt cct tca     1152
Ser Glu Ile Gln Asn Ile Ser Ala His Val Leu Asp Ser Leu Pro Ser
    370                 375                 380

tat gct gca caa gtc tcg gct gcg tct ggt aat gtt aca aaa gcc gct     1200
Tyr Ala Ala Gln Val Ser Ala Ala Ser Gly Asn Val Thr Lys Ala Ala
385                 390                 395                 400

gat ttg tta gaa ttc ttc aaa att caa cat gac ctt att ttt tca acc     1248
Asp Leu Leu Glu Phe Phe Lys Ile Gln His Asp Leu Ile Phe Ser Thr
                405                 410                 415

acc cac ccg gtt ccc atg gct gag atc ctc gtc ata cca tcc gca aca     1296
Thr His Pro Val Pro Met Ala Glu Ile Leu Val Ile Pro Ser Ala Thr
            420                 425                 430

ggt ttc aag tca gag tac tgg gct cta ttg cca ttt gca aga gga aac     1344
Gly Phe Lys Ser Glu Tyr Trp Ala Leu Leu Pro Phe Ala Arg Gly Asn
        435                 440                 445

ata cac atc act tct tcg ata cca ggc acc cct gcg gcg atc aat cca     1392
Ile His Ile Thr Ser Ser Ile Pro Gly Thr Pro Ala Ala Ile Asn Pro
    450                 455                 460

aat tat tac atg ctt gac tgg gat atc aca tcg caa atc act act gca     1440
Asn Tyr Tyr Met Leu Asp Trp Asp Ile Thr Ser Gln Ile Thr Thr Ala
465                 470                 475                 480

aag ttc atc cgt tcc gtc tac gct acc tct cca ttg tcc act ctg gtt     1488
Lys Phe Ile Arg Ser Val Tyr Ala Thr Ser Pro Leu Ser Thr Leu Val
                485                 490                 495

ggc tca gaa act aaa cca ggt ttg gag aca tta tca gca aat gct acc     1536
Gly Ser Glu Thr Lys Pro Gly Leu Glu Thr Leu Ser Ala Asn Ala Thr
            500                 505                 510

gag gcg gaa tgg tct gaa tgg att aaa gct ggc tat cgt ccc aac ttt     1584
Glu Ala Glu Trp Ser Glu Trp Ile Lys Ala Gly Tyr Arg Pro Asn Phe
        515                 520                 525

cac cca gta tca acc gct gct atg atg cca aga gag gtt ggt gga gta     1632
His Pro Val Ser Thr Ala Ala Met Met Pro Arg Glu Val Gly Gly Val
    530                 535                 540

gta gat tca aga ttg aag gtc tat ggg aca tca aat gtg aga gtt gtg     1680
Val Asp Ser Arg Leu Lys Val Tyr Gly Thr Ser Asn Val Arg Val Val
545                 550                 555                 560

gat gcc agt gta ctg cct atg cag gtt agt gga cat ttg gtc agt act     1728
Asp Ala Ser Val Leu Pro Met Gln Val Ser Gly His Leu Val Ser Thr
                565                 570                 575

tta tac gct gta gcg gag aga gcg gca gat ttg atc aag gag gat att     1776
Leu Tyr Ala Val Ala Glu Arg Ala Ala Asp Leu Ile Lys Glu Asp Ile
            580                 585                 590

taa                                                                 1779
```

<210> SEQ ID NO 49
<211> LENGTH: 592
<212> TYPE: PRT

<213> ORGANISM: Artificial Sequence
<220> FEATURE:
<223> OTHER INFORMATION: Synthetic Construct

<400> SEQUENCE: 49

```
Met Leu Gly Lys Leu Ser Phe Leu Ser Ala Leu Ser Leu Ala Val Ala
1               5                   10                  15

Ala Pro Leu Ser Pro Asp Leu Ser Leu Thr Tyr Asp Tyr Val Ile Val
            20                  25                  30

Gly Ala Gly Thr Ser Gly Leu Val Ile Ala Asn Arg Leu Ser Glu Leu
        35                  40                  45

Asn Val Thr Val Ala Val Ile Glu Ala Gly Asp Ser Gly Tyr Asn Asn
    50                  55                  60

Val Asn Val Thr Asn Pro Ala Gly Tyr Gly Leu Ala Phe Gly Thr Asp
65                  70                  75                  80

Ile Asp Trp Ala Tyr Gln Ser Thr Asn Gln Lys Tyr Ala Gly Asn Ala
                85                  90                  95

Thr Gln Thr Leu Arg Ala Gly Lys Val Ile Gly Gly Thr Ser Thr Ile
            100                 105                 110

Asn Gly Met Ala Tyr Thr Arg Ala Glu Asp Val Gln Ile Asp Ala Trp
        115                 120                 125

Ala Ala Leu Gly Asn Asp Gly Trp Asn Trp Glu Asn Leu Phe Pro Tyr
    130                 135                 140

Tyr Lys Lys Ser Gln Thr Leu Gln Ala Pro Thr Ala Ala Gln Ala Glu
145                 150                 155                 160

Ala Gly Ala Thr Tyr Asp Pro Ser Ala Asn Gly Phe Asp Gly Pro Leu
                165                 170                 175

Lys Val Gly Trp Leu Lys Ser Leu Ala Asn Asp Asp Phe His Ile Ile
            180                 185                 190

Leu Asn Asp Thr Tyr Ala Ser Leu Gly Ile Phe Ala Asn Glu Asp Val
        195                 200                 205

Asn Thr Gly Arg Met Val Gly Tyr Asn Arg Tyr Pro Val Thr Tyr Asp
    210                 215                 220

Glu Thr Leu Asn Val Arg His Asp Ala Gly Arg Ala Tyr Tyr Tyr Pro
225                 230                 235                 240

Ile Ala Asn Arg Thr Asn Leu His Leu Tyr Pro Asn Thr Met Ala Gln
                245                 250                 255

Arg Leu Thr Trp Lys Ser Gly Ala Asp Val Pro Thr Ala Asn Gly Val
            260                 265                 270

Glu Val Leu Thr Asn Asn Ser Ser Ile Pro Tyr Thr Ile Ser Ala Asn
        275                 280                 285

Ser Glu Val Ile Leu Ser Ala Gly Ala Leu Ala Ser Pro Leu Leu Leu
    290                 295                 300

Glu Leu Ser Gly Ile Gly Asn Pro Ser Leu Leu Asn Lys Tyr Asn Ile
305                 310                 315                 320

Pro Val Val Val Asp Leu Pro Thr Val Gly Glu Asn Leu Gln Asp Gln
                325                 330                 335

Thr Asn Asn Gly Leu Ala Tyr Thr Val Ser Lys Asp Ala Ser Phe Ser
            340                 345                 350

Gly Val Gly Thr Leu Val Thr Tyr Pro Ser Ala Ala Gln Val Phe Gly
        355                 360                 365

Ser Glu Ile Gln Asn Ile Ser Ala His Val Leu Asp Ser Leu Pro Ser
    370                 375                 380

Tyr Ala Ala Gln Val Ser Ala Ala Ser Gly Asn Val Thr Lys Ala Ala
```

```
385                 390                 395                 400

Asp Leu Leu Glu Phe Phe Lys Ile Gln His Asp Leu Ile Phe Ser Thr
                405                 410                 415

Thr His Pro Val Pro Met Ala Glu Ile Leu Val Ile Pro Ser Ala Thr
            420                 425                 430

Gly Phe Lys Ser Glu Tyr Trp Ala Leu Leu Pro Phe Ala Arg Gly Asn
        435                 440                 445

Ile His Ile Thr Ser Ser Ile Pro Gly Thr Pro Ala Ala Ile Asn Pro
    450                 455                 460

Asn Tyr Tyr Met Leu Asp Trp Asp Ile Thr Ser Gln Ile Thr Thr Ala
465                 470                 475                 480

Lys Phe Ile Arg Ser Val Tyr Ala Thr Ser Pro Leu Ser Thr Leu Val
                485                 490                 495

Gly Ser Glu Thr Lys Pro Gly Leu Glu Thr Leu Ser Ala Asn Ala Thr
            500                 505                 510

Glu Ala Glu Trp Ser Glu Trp Ile Lys Ala Gly Tyr Arg Pro Asn Phe
        515                 520                 525

His Pro Val Ser Thr Ala Ala Met Met Pro Arg Glu Val Gly Gly Val
    530                 535                 540

Val Asp Ser Arg Leu Lys Val Tyr Gly Thr Ser Asn Val Arg Val Val
545                 550                 555                 560

Asp Ala Ser Val Leu Pro Met Gln Val Ser Gly His Leu Val Ser Thr
                565                 570                 575

Leu Tyr Ala Val Ala Glu Arg Ala Ala Asp Leu Ile Lys Glu Asp Ile
            580                 585                 590


<210> SEQ ID NO 50
<211> LENGTH: 1782
<212> TYPE: DNA
<213> ORGANISM: Artificial Sequence
<220> FEATURE:
<223> OTHER INFORMATION: BotGLD-Atsig gene
<220> FEATURE:
<221> NAME/KEY: sig_peptide
<222> LOCATION: (1)..(66)
<220> FEATURE:
<221> NAME/KEY: sig_peptide
<222> LOCATION: (1)..(57)
<223> OTHER INFORMATION: A_terreus_signal_peptide
<220> FEATURE:
<221> NAME/KEY: CDS
<222> LOCATION: (1)..(1782)
<220> FEATURE:
<221> NAME/KEY: sig_peptide
<222> LOCATION: (58)..(66)
<223> OTHER INFORMATION: B_tulipae_signal_peptide

<400> SEQUENCE: 50

atg ttg gga aag ctc tcc ttc ctc agt gcc ctg tcc ctg gca gtg gcg       48
Met Leu Gly Lys Leu Ser Phe Leu Ser Ala Leu Ser Leu Ala Val Ala
1               5                   10                  15

gca cct ttg agc acc gac tct act tta act tat gat tat att gtt att       96
Ala Pro Leu Ser Thr Asp Ser Thr Leu Thr Tyr Asp Tyr Ile Val Ile
            20                  25                  30

ggt gct gga acc agt ggt cta gtc atc gca aac cgt tta tcc gag tta      144
Gly Ala Gly Thr Ser Gly Leu Val Ile Ala Asn Arg Leu Ser Glu Leu
        35                  40                  45

aat gtc act gtg gct gtc att gag gca ggt gat tcg ggt tac aac aat      192
Asn Val Thr Val Ala Val Ile Glu Ala Gly Asp Ser Gly Tyr Asn Asn
    50                  55                  60

ccc aat gtg aca aac cca tcc ggt tat gga tta tct ttt gga aca gac      240
```

-continued

```
Pro Asn Val Thr Asn Pro Ser Gly Tyr Gly Leu Ser Phe Gly Thr Asp
65                  70                  75                  80

atc gat tgg gcg tat caa tcg acc aac cag aag tat gca gga aac acg      288
Ile Asp Trp Ala Tyr Gln Ser Thr Asn Gln Lys Tyr Ala Gly Asn Thr
                85                  90                  95

agc caa gtc tta cga gct ggc aaa atc atc gga ggg act agt act atc      336
Ser Gln Val Leu Arg Ala Gly Lys Ile Ile Gly Gly Thr Ser Thr Ile
            100                 105                 110

aat gga atg gca tac acg cga gcg gaa gat gtt caa att gat gct tgg      384
Asn Gly Met Ala Tyr Thr Arg Ala Glu Asp Val Gln Ile Asp Ala Trp
        115                 120                 125

gca gcc att gga aat gat gga tgg aac tgg gca aat ctt ttc cca tac      432
Ala Ala Ile Gly Asn Asp Gly Trp Asn Trp Ala Asn Leu Phe Pro Tyr
    130                 135                 140

tac aaa aag tct cag aca ctc gaa atc cct acc act gct caa gtt gaa      480
Tyr Lys Lys Ser Gln Thr Leu Glu Ile Pro Thr Thr Ala Gln Val Glu
145                 150                 155                 160

gct ggt gca gca tat gac gcc tca gcg aat gga ttc gat gga cca ctg      528
Ala Gly Ala Ala Tyr Asp Ala Ser Ala Asn Gly Phe Asp Gly Pro Leu
                165                 170                 175

aag gtt ggc tgg ctc aac agc ttg gaa gat act agc aac ttc cat aca      576
Lys Val Gly Trp Leu Asn Ser Leu Glu Asp Thr Ser Asn Phe His Thr
            180                 185                 190

acc ttg aat gat aca ttt gca ggt ctt ggt gtt cct tca aat gat gat      624
Thr Leu Asn Asp Thr Phe Ala Gly Leu Gly Val Pro Ser Asn Asp Asp
        195                 200                 205

gtc aat act ggt aga atg gtt ggt tac agt cga tac cca gct act tac      672
Val Asn Thr Gly Arg Met Val Gly Tyr Ser Arg Tyr Pro Ala Thr Tyr
    210                 215                 220

gac aga aca ttg aac gtt cgt cat gac gct gga cga gca tat tat tat      720
Asp Arg Thr Leu Asn Val Arg His Asp Ala Gly Arg Ala Tyr Tyr Tyr
225                 230                 235                 240

cca att gcc aac cgc acc aat ctt cat ctt tac cca aat act atg gct      768
Pro Ile Ala Asn Arg Thr Asn Leu His Leu Tyr Pro Asn Thr Met Ala
                245                 250                 255

caa cga ctc aca tgg aca tcc gac gct aat acc cct acc gca aat gga      816
Gln Arg Leu Thr Trp Thr Ser Asp Ala Asn Thr Pro Thr Ala Asn Gly
            260                 265                 270

gtc gaa gtt ctt tcc aac aac tca agc att cca tac act att cat gca      864
Val Glu Val Leu Ser Asn Asn Ser Ser Ile Pro Tyr Thr Ile His Ala
        275                 280                 285

aac tcc gaa gtc att ctt tca gct gga gct cta gca tct cct ctt ctt      912
Asn Ser Glu Val Ile Leu Ser Ala Gly Ala Leu Ala Ser Pro Leu Leu
    290                 295                 300

ctc gaa ctt tcc ggt att gga aac cct tcc atc ttg agc aag cac aat      960
Leu Glu Leu Ser Gly Ile Gly Asn Pro Ser Ile Leu Ser Lys His Asn
305                 310                 315                 320

atc tca gtt gta gtt gat ctc cca act gta gga gaa aat ctt caa gat     1008
Ile Ser Val Val Val Asp Leu Pro Thr Val Gly Glu Asn Leu Gln Asp
                325                 330                 335

caa acg aat act ggc ctt gca tac aac agt tca ggc aac acc tct ttc     1056
Gln Thr Asn Thr Gly Leu Ala Tyr Asn Ser Ser Gly Asn Thr Ser Phe
            340                 345                 350

tct gga gct gga acc ttg gta gct tat cct tcc gca gcc caa tta ttt     1104
Ser Gly Ala Gly Thr Leu Val Ala Tyr Pro Ser Ala Ala Gln Leu Phe
        355                 360                 365

ggt tct gaa gtt caa aaa atc tct gct cat gtt ctt caa tct ctt cct     1152
Gly Ser Glu Val Gln Lys Ile Ser Ala His Val Leu Gln Ser Leu Pro
    370                 375                 380
```

```
tca tat gct gca caa gta tca gct gca tca ggt aac atc acc aaa gct      1200
Ser Tyr Ala Ala Gln Val Ser Ala Ala Ser Gly Asn Ile Thr Lys Ala
385                 390                 395                 400

gca gat ttg ttg aaa ttc ttc aaa att caa cat gat ctg atc ttc tca      1248
Ala Asp Leu Leu Lys Phe Phe Lys Ile Gln His Asp Leu Ile Phe Ser
                405                 410                 415

act acc cac cca gtt cca atg gct gaa ata ctc atc tca cca tct gca      1296
Thr Thr His Pro Val Pro Met Ala Glu Ile Leu Ile Ser Pro Ser Ala
            420                 425                 430

aca gct ttc agc tcg gaa tat tgg gcc ttg tta cca ttt gca aga gga      1344
Thr Ala Phe Ser Ser Glu Tyr Trp Ala Leu Leu Pro Phe Ala Arg Gly
        435                 440                 445

agt att cac atc aca tct tcc gta gct ggc aca ccc gca gct atc aat      1392
Ser Ile His Ile Thr Ser Ser Val Ala Gly Thr Pro Ala Ala Ile Asn
    450                 455                 460

cca aat tat ttc atg ttt gat tgg gat gtc aca tct caa atc gct acg      1440
Pro Asn Tyr Phe Met Phe Asp Trp Asp Val Thr Ser Gln Ile Ala Thr
465                 470                 475                 480

gcc aag ttt att cgc tcc att tat gcg gct tct cca ctg tcc tct ttc      1488
Ala Lys Phe Ile Arg Ser Ile Tyr Ala Ala Ser Pro Leu Ser Ser Phe
                485                 490                 495

gtc gga tca gag acc aag cct gga ttg aac aaa gta tca gct aat gct      1536
Val Gly Ser Glu Thr Lys Pro Gly Leu Asn Lys Val Ser Ala Asn Ala
            500                 505                 510

acg gag gct gaa tgg ttt gat tgg gtt aaa act gct tat cgc tca aac      1584
Thr Glu Ala Glu Trp Phe Asp Trp Val Lys Thr Ala Tyr Arg Ser Asn
        515                 520                 525

ttc cat cca gta tca acg gct gca atg atg cca aga gag atc ggt gga      1632
Phe His Pro Val Ser Thr Ala Ala Met Met Pro Arg Glu Ile Gly Gly
    530                 535                 540

gtg gta gac tca agg ttg aag gta tat gga aca gca aat gtg aga gtt      1680
Val Val Asp Ser Arg Leu Lys Val Tyr Gly Thr Ala Asn Val Arg Val
545                 550                 555                 560

gtg gat gct agt ata tta cct atg cag gtt tct gga cat tta gtt agt      1728
Val Asp Ala Ser Ile Leu Pro Met Gln Val Ser Gly His Leu Val Ser
                565                 570                 575

act ttg tat gct gtg gca gag aga gca gca gat ttg atc aag gag gac      1776
Thr Leu Tyr Ala Val Ala Glu Arg Ala Ala Asp Leu Ile Lys Glu Asp
            580                 585                 590

att tag                                                              1782
Ile
```

<210> SEQ ID NO 51
<211> LENGTH: 593
<212> TYPE: PRT
<213> ORGANISM: Artificial Sequence
<220> FEATURE:
<223> OTHER INFORMATION: Synthetic Construct

<400> SEQUENCE: 51

```
Met Leu Gly Lys Leu Ser Phe Leu Ser Ala Leu Ser Leu Ala Val Ala
1               5                   10                  15

Ala Pro Leu Ser Thr Asp Ser Thr Leu Thr Tyr Asp Tyr Ile Val Ile
            20                  25                  30

Gly Ala Gly Thr Ser Gly Leu Val Ile Ala Asn Arg Leu Ser Glu Leu
        35                  40                  45

Asn Val Thr Val Ala Val Ile Glu Ala Gly Asp Ser Gly Tyr Asn Asn
    50                  55                  60

Pro Asn Val Thr Asn Pro Ser Gly Tyr Gly Leu Ser Phe Gly Thr Asp
65                  70                  75                  80
```

-continued

```
Ile Asp Trp Ala Tyr Gln Ser Thr Asn Gln Lys Tyr Ala Gly Asn Thr
                85                  90                  95

Ser Gln Val Leu Arg Ala Gly Lys Ile Ile Gly Gly Thr Ser Thr Ile
            100                 105                 110

Asn Gly Met Ala Tyr Thr Arg Ala Glu Asp Val Gln Ile Asp Ala Trp
        115                 120                 125

Ala Ala Ile Gly Asn Asp Gly Trp Asn Trp Ala Asn Leu Phe Pro Tyr
    130                 135                 140

Tyr Lys Lys Ser Gln Thr Leu Glu Ile Pro Thr Thr Ala Gln Val Glu
145                 150                 155                 160

Ala Gly Ala Ala Tyr Asp Ala Ser Ala Asn Gly Phe Asp Gly Pro Leu
                165                 170                 175

Lys Val Gly Trp Leu Asn Ser Leu Glu Asp Thr Ser Asn Phe His Thr
            180                 185                 190

Thr Leu Asn Asp Thr Phe Ala Gly Leu Gly Val Pro Ser Asn Asp Asp
        195                 200                 205

Val Asn Thr Gly Arg Met Val Gly Tyr Ser Arg Tyr Pro Ala Thr Tyr
    210                 215                 220

Asp Arg Thr Leu Asn Val Arg His Asp Ala Gly Arg Ala Tyr Tyr Tyr
225                 230                 235                 240

Pro Ile Ala Asn Arg Thr Asn Leu His Leu Tyr Pro Asn Thr Met Ala
                245                 250                 255

Gln Arg Leu Thr Trp Thr Ser Asp Ala Asn Thr Pro Thr Ala Asn Gly
            260                 265                 270

Val Glu Val Leu Ser Asn Asn Ser Ser Ile Pro Tyr Thr Ile His Ala
        275                 280                 285

Asn Ser Glu Val Ile Leu Ser Ala Gly Ala Leu Ala Ser Pro Leu Leu
    290                 295                 300

Leu Glu Leu Ser Gly Ile Gly Asn Pro Ser Ile Leu Ser Lys His Asn
305                 310                 315                 320

Ile Ser Val Val Val Asp Leu Pro Thr Val Gly Glu Asn Leu Gln Asp
                325                 330                 335

Gln Thr Asn Thr Gly Leu Ala Tyr Asn Ser Ser Gly Asn Thr Ser Phe
            340                 345                 350

Ser Gly Ala Gly Thr Leu Val Ala Tyr Pro Ser Ala Ala Gln Leu Phe
        355                 360                 365

Gly Ser Glu Val Gln Lys Ile Ser Ala His Val Leu Gln Ser Leu Pro
    370                 375                 380

Ser Tyr Ala Ala Gln Val Ser Ala Ala Ser Gly Asn Ile Thr Lys Ala
385                 390                 395                 400

Ala Asp Leu Leu Lys Phe Phe Lys Ile Gln His Asp Leu Ile Phe Ser
                405                 410                 415

Thr Thr His Pro Val Pro Met Ala Glu Ile Leu Ile Ser Pro Ser Ala
            420                 425                 430

Thr Ala Phe Ser Ser Glu Tyr Trp Ala Leu Leu Pro Phe Ala Arg Gly
        435                 440                 445

Ser Ile His Ile Thr Ser Ser Val Ala Gly Thr Pro Ala Ala Ile Asn
    450                 455                 460

Pro Asn Tyr Phe Met Phe Asp Trp Asp Val Thr Ser Gln Ile Ala Thr
465                 470                 475                 480

Ala Lys Phe Ile Arg Ser Ile Tyr Ala Ala Ser Pro Leu Ser Ser Phe
                485                 490                 495
```

```
Val Gly Ser Glu Thr Lys Pro Gly Leu Asn Lys Val Ser Ala Asn Ala
            500                 505                 510

Thr Glu Ala Glu Trp Phe Asp Trp Val Lys Thr Ala Tyr Arg Ser Asn
        515                 520                 525

Phe His Pro Val Ser Thr Ala Ala Met Met Pro Arg Glu Ile Gly Gly
    530                 535                 540

Val Val Asp Ser Arg Leu Lys Val Tyr Gly Thr Ala Asn Val Arg Val
545                 550                 555                 560

Val Asp Ala Ser Ile Leu Pro Met Gln Val Ser Gly His Leu Val Ser
                565                 570                 575

Thr Leu Tyr Ala Val Ala Glu Arg Ala Ala Asp Leu Ile Lys Glu Asp
            580                 585                 590

Ile


<210> SEQ ID NO 52
<211> LENGTH: 1776
<212> TYPE: DNA
<213> ORGANISM: Artificial Sequence
<220> FEATURE:
<223> OTHER INFORMATION: CiGLD-Atsig gene
<220> FEATURE:
<221> NAME/KEY: sig_peptide
<222> LOCATION: (1)..(57)
<223> OTHER INFORMATION: A_terreus_signal_peptide
<220> FEATURE:
<221> NAME/KEY: CDS
<222> LOCATION: (1)..(1776)

<400> SEQUENCE: 52

atg ttg gga aag ctc tcc ttc ctc agt gcc ctg tcc ctg gca gtg gcg       48
Met Leu Gly Lys Leu Ser Phe Leu Ser Ala Leu Ser Leu Ala Val Ala
1               5                   10                  15

gca cct ttg gtt gcc tta acc tac gat tat gtt atc gtt ggt gct gga       96
Ala Pro Leu Val Ala Leu Thr Tyr Asp Tyr Val Ile Val Gly Ala Gly
            20                  25                  30

aca agt ggt ctc gtc act gca cac cgt ctg tcc gag ttg gct gat gtc      144
Thr Ser Gly Leu Val Thr Ala His Arg Leu Ser Glu Leu Ala Asp Val
        35                  40                  45

act gtc gcc gtg att gaa gct ggt gaa tcg aac tac aac aac gcc aat      192
Thr Val Ala Val Ile Glu Ala Gly Glu Ser Asn Tyr Asn Asn Ala Asn
    50                  55                  60

gtc acc aac cct gca ggc tat gga ttg gct ttt ggt acc caa att gat      240
Val Thr Asn Pro Ala Gly Tyr Gly Leu Ala Phe Gly Thr Gln Ile Asp
65                  70                  75                  80

tgg caa tac caa aca acc gtc caa gag tac gga gga gac gtc acc aag      288
Trp Gln Tyr Gln Thr Thr Val Gln Glu Tyr Gly Gly Asp Val Thr Lys
                85                  90                  95

gtt atc cga gct ggt aaa tcc atc gga gga act agc aca atc aac gga      336
Val Ile Arg Ala Gly Lys Ser Ile Gly Gly Thr Ser Thr Ile Asn Gly
            100                 105                 110

atg gct tac acc cga gct gag gat gtt cag gtt gat gca tgg gaa gcc      384
Met Ala Tyr Thr Arg Ala Glu Asp Val Gln Val Asp Ala Trp Glu Ala
        115                 120                 125

ctt gga aat gag gga tgg aac tgg gca aac atg ctc cca tac tac aag      432
Leu Gly Asn Glu Gly Trp Asn Trp Ala Asn Met Leu Pro Tyr Tyr Lys
    130                 135                 140

aag tct caa aca ctt cag gtt cca act gag gcc caa gct gca cta gga      480
Lys Ser Gln Thr Leu Gln Val Pro Thr Glu Ala Gln Ala Ala Leu Gly
145                 150                 155                 160

gca cat tac gac cct gcg tca aac gga tat gaa gga cca ttg aag gtt      528
Ala His Tyr Asp Pro Ala Ser Asn Gly Tyr Glu Gly Pro Leu Lys Val
```

```
                165                 170                 175

ggt tgg gtc aac gcc atg gcc acc gat gac ttc cac aca att ttg aac      576
Gly Trp Val Asn Ala Met Ala Thr Asp Asp Phe His Thr Ile Leu Asn
            180                 185                 190

gag acc tac gct gct ctc gac gtt ccc gcc aac aac gat gtc aac act      624
Glu Thr Tyr Ala Ala Leu Asp Val Pro Ala Asn Asn Asp Val Asn Thr
        195                 200                 205

ggt aag atg atc ggt tac acc aga tac cca gct acc tac gac aga acc      672
Gly Lys Met Ile Gly Tyr Thr Arg Tyr Pro Ala Thr Tyr Asp Arg Thr
    210                 215                 220

ttg aac atg cgt tgt gat gcc gga aga gcc tac tac tac cca atc cag      720
Leu Asn Met Arg Cys Asp Ala Gly Arg Ala Tyr Tyr Tyr Pro Ile Gln
225                 230                 235                 240

aac cgt acc aac ctt cat ctt tac cca aac acc atg gcc cag cgt ctt      768
Asn Arg Thr Asn Leu His Leu Tyr Pro Asn Thr Met Ala Gln Arg Leu
                245                 250                 255

aca tgg aaa tcc ggt gcc tcc acc ccc act gca gag gga gtt gag gtt      816
Thr Trp Lys Ser Gly Ala Ser Thr Pro Thr Ala Glu Gly Val Glu Val
            260                 265                 270

ctt gcc gac ggc gag acc acc cca tac acc att cac gca agc tcc gaa      864
Leu Ala Asp Gly Glu Thr Thr Pro Tyr Thr Ile His Ala Ser Ser Glu
        275                 280                 285

gtc atc atc tcc gcc ggt gct ctt ggt tcc cct ctt gtt ctc gag cac      912
Val Ile Ile Ser Ala Gly Ala Leu Gly Ser Pro Leu Val Leu Glu His
    290                 295                 300

tct ggt att ggt aac cct gct atc ctt gag aag tac aac att tcc gtc      960
Ser Gly Ile Gly Asn Pro Ala Ile Leu Glu Lys Tyr Asn Ile Ser Val
305                 310                 315                 320

gtc gtt gat ctc cca acc gtc gga gag aat ctt cag gat caa aca aac     1008
Val Val Asp Leu Pro Thr Val Gly Glu Asn Leu Gln Asp Gln Thr Asn
                325                 330                 335

acc gct ctt ggt ttc gac acc tca agc gac aat gtc act tac tca gcc     1056
Thr Ala Leu Gly Phe Asp Thr Ser Ser Asp Asn Val Thr Tyr Ser Ala
            340                 345                 350

gtt tct acc tac ctc ggt tac cca tct gct gct cag atg ttc ggt tcc     1104
Val Ser Thr Tyr Leu Gly Tyr Pro Ser Ala Ala Gln Met Phe Gly Ser
        355                 360                 365

gat ttc aag acc gtc gcc gct gaa att ctc gct gct ctt cct tcc tat     1152
Asp Phe Lys Thr Val Ala Ala Glu Ile Leu Ala Ala Leu Pro Ser Tyr
    370                 375                 380

gcc gac aag gtc gcc att gca tca ggc aat gtt acc aag gcc gct gat     1200
Ala Asp Lys Val Ala Ile Ala Ser Gly Asn Val Thr Lys Ala Ala Asp
385                 390                 395                 400

ttg ttg aag ttc ttc aag att caa tac gag ctc atc ttc agc gcc acc     1248
Leu Leu Lys Phe Phe Lys Ile Gln Tyr Glu Leu Ile Phe Ser Ala Thr
                405                 410                 415

agc cct gtc cct gtc gcc gag ctt ctc gtt acc cca gtt gga acc acc     1296
Ser Pro Val Pro Val Ala Glu Leu Leu Val Thr Pro Val Gly Thr Thr
            420                 425                 430

tac agt gcc gag ttc tgg tcc ttg ttg cca ttc tcc cgt gga aac atc     1344
Tyr Ser Ala Glu Phe Trp Ser Leu Leu Pro Phe Ser Arg Gly Asn Ile
        435                 440                 445

cac atc tca tct gcc acc cca ggt gtc gcc gca acc atc aac cca aac     1392
His Ile Ser Ser Ala Thr Pro Gly Val Ala Ala Thr Ile Asn Pro Asn
    450                 455                 460

tac ttc atg ctt gat tat gat atg atc tcg caa gtc cgc tcc gcc aag     1440
Tyr Phe Met Leu Asp Tyr Asp Met Ile Ser Gln Val Arg Ser Ala Lys
465                 470                 475                 480

tac att cgt gag atc ttt gcc acc act cca ttg tcc cct ctc gtt ggc     1488
```

-continued

```
Tyr Ile Arg Glu Ile Phe Ala Thr Thr Pro Leu Ser Pro Leu Val Gly
            485                 490                 495

agc gaa acc acc cct ggt ttg gac tct att gcc tca gct gcc acc gag     1536
Ser Glu Thr Thr Pro Gly Leu Asp Ser Ile Ala Ser Ala Ala Thr Glu
            500                 505                 510

gcc gaa tgg gcc gct tgg gtc aag acc gcc tac cga tcc aac ttc cac     1584
Ala Glu Trp Ala Ala Trp Val Lys Thr Ala Tyr Arg Ser Asn Phe His
        515                 520                 525

ccc gtc gcc acc gct gcc atg atg cca cgc gag atc gga gga gtc gtc     1632
Pro Val Ala Thr Ala Ala Met Met Pro Arg Glu Ile Gly Gly Val Val
    530                 535                 540

gac tcc cgc ttg aag gtc tac gga acc acc aac gtc aga gtc gtc gat     1680
Asp Ser Arg Leu Lys Val Tyr Gly Thr Thr Asn Val Arg Val Val Asp
545                 550                 555                 560

gcc agt atc ttg ccc atg caa gtt tgc gga cat ttg acc agt act ttg     1728
Ala Ser Ile Leu Pro Met Gln Val Cys Gly His Leu Thr Ser Thr Leu
                565                 570                 575

tac gcc atg tcc gag aga gcc gct gac ttg atc aag gaa gat atg taa     1776
Tyr Ala Met Ser Glu Arg Ala Ala Asp Leu Ile Lys Glu Asp Met
            580                 585                 590


<210> SEQ ID NO 53
<211> LENGTH: 591
<212> TYPE: PRT
<213> ORGANISM: Artificial Sequence
<220> FEATURE:
<223> OTHER INFORMATION: Synthetic Construct

<400> SEQUENCE: 53

Met Leu Gly Lys Leu Ser Phe Leu Ser Ala Leu Ser Leu Ala Val Ala
1               5                   10                  15

Ala Pro Leu Val Ala Leu Thr Tyr Asp Tyr Val Ile Val Gly Ala Gly
            20                  25                  30

Thr Ser Gly Leu Val Thr Ala His Arg Leu Ser Glu Leu Ala Asp Val
        35                  40                  45

Thr Val Ala Val Ile Glu Ala Gly Glu Ser Asn Tyr Asn Asn Ala Asn
    50                  55                  60

Val Thr Asn Pro Ala Gly Tyr Gly Leu Ala Phe Gly Thr Gln Ile Asp
65                  70                  75                  80

Trp Gln Tyr Gln Thr Thr Val Gln Glu Tyr Gly Gly Asp Val Thr Lys
                85                  90                  95

Val Ile Arg Ala Gly Lys Ser Ile Gly Gly Thr Ser Thr Ile Asn Gly
            100                 105                 110

Met Ala Tyr Thr Arg Ala Glu Asp Val Gln Val Asp Ala Trp Glu Ala
        115                 120                 125

Leu Gly Asn Glu Gly Trp Asn Trp Ala Asn Met Leu Pro Tyr Tyr Lys
    130                 135                 140

Lys Ser Gln Thr Leu Gln Val Pro Thr Glu Ala Gln Ala Ala Leu Gly
145                 150                 155                 160

Ala His Tyr Asp Pro Ala Ser Asn Gly Tyr Glu Gly Pro Leu Lys Val
                165                 170                 175

Gly Trp Val Asn Ala Met Ala Thr Asp Asp Phe His Thr Ile Leu Asn
            180                 185                 190

Glu Thr Tyr Ala Ala Leu Asp Val Pro Ala Asn Asn Asp Val Asn Thr
        195                 200                 205

Gly Lys Met Ile Gly Tyr Thr Arg Tyr Pro Ala Thr Tyr Asp Arg Thr
    210                 215                 220
```

-continued

```
Leu Asn Met Arg Cys Asp Ala Gly Arg Ala Tyr Tyr Tyr Pro Ile Gln
225                 230                 235                 240

Asn Arg Thr Asn Leu His Leu Tyr Pro Asn Thr Met Ala Gln Arg Leu
                245                 250                 255

Thr Trp Lys Ser Gly Ala Ser Thr Pro Thr Ala Glu Gly Val Glu Val
            260                 265                 270

Leu Ala Asp Gly Glu Thr Thr Pro Tyr Thr Ile His Ala Ser Ser Glu
        275                 280                 285

Val Ile Ile Ser Ala Gly Ala Leu Gly Ser Pro Leu Val Leu Glu His
    290                 295                 300

Ser Gly Ile Gly Asn Pro Ala Ile Leu Glu Lys Tyr Asn Ile Ser Val
305                 310                 315                 320

Val Val Asp Leu Pro Thr Val Gly Glu Asn Leu Gln Asp Gln Thr Asn
                325                 330                 335

Thr Ala Leu Gly Phe Asp Thr Ser Ser Asp Asn Val Thr Tyr Ser Ala
            340                 345                 350

Val Ser Thr Tyr Leu Gly Tyr Pro Ser Ala Ala Gln Met Phe Gly Ser
        355                 360                 365

Asp Phe Lys Thr Val Ala Ala Glu Ile Leu Ala Ala Leu Pro Ser Tyr
    370                 375                 380

Ala Asp Lys Val Ala Ile Ala Ser Gly Asn Val Thr Lys Ala Ala Asp
385                 390                 395                 400

Leu Leu Lys Phe Phe Lys Ile Gln Tyr Glu Leu Ile Phe Ser Ala Thr
                405                 410                 415

Ser Pro Val Pro Val Ala Glu Leu Leu Val Thr Pro Val Gly Thr Thr
            420                 425                 430

Tyr Ser Ala Glu Phe Trp Ser Leu Leu Pro Phe Ser Arg Gly Asn Ile
        435                 440                 445

His Ile Ser Ser Ala Thr Pro Gly Val Ala Ala Thr Ile Asn Pro Asn
    450                 455                 460

Tyr Phe Met Leu Asp Tyr Asp Met Ile Ser Gln Val Arg Ser Ala Lys
465                 470                 475                 480

Tyr Ile Arg Glu Ile Phe Ala Thr Thr Pro Leu Ser Pro Leu Val Gly
                485                 490                 495

Ser Glu Thr Thr Pro Gly Leu Asp Ser Ile Ala Ser Ala Ala Thr Glu
            500                 505                 510

Ala Glu Trp Ala Ala Trp Val Lys Thr Ala Tyr Arg Ser Asn Phe His
        515                 520                 525

Pro Val Ala Thr Ala Ala Met Met Pro Arg Glu Ile Gly Gly Val Val
    530                 535                 540

Asp Ser Arg Leu Lys Val Tyr Gly Thr Thr Asn Val Arg Val Val Asp
545                 550                 555                 560

Ala Ser Ile Leu Pro Met Gln Val Cys Gly His Leu Thr Ser Thr Leu
                565                 570                 575

Tyr Ala Met Ser Glu Arg Ala Ala Asp Leu Ile Lys Glu Asp Met
            580                 585                 590
```